United States Patent
Taniguchi et al.

(10) Patent No.: US 7,195,587 B2
(45) Date of Patent: *Mar. 27, 2007

(54) APPARATUS AND METHOD USING IT FOR DETECTING AND DISPLAYING FORM OF INSERTION PART OF ENDOSCOPE INSERTED INTO BODY CAVITY

(75) Inventors: Akira Taniguchi, Hachioji (JP); Sumihiro Uchimura, Sagamihara (JP); Yasuhiro Yoshizawa, Hachioji (JP); Takeshi Kawabata, Sagamihara (JP); Masanao Hara, Hachioji (JP); Kazutaka Tsuji, Hachioji (JP); Chieko Aizawa, Hachioji (JP)

(73) Assignee: Olympus Corporation (JP)

(*) Notice: Subject to any disclaimer, the term of this patent is extended or adjusted under 35 U.S.C. 154(b) by 287 days.

This patent is subject to a terminal disclaimer.

(21) Appl. No.: 10/684,544

(22) Filed: Oct. 14, 2003

(65) Prior Publication Data

US 2004/0116775 A1    Jun. 17, 2004

Related U.S. Application Data

(62) Division of application No. 09/632,255, filed on Aug. 3, 2000, now Pat. No. 6,773,393.

(30) Foreign Application Priority Data

| Aug. 5, 1999 | (JP) | H11-222858 |
| Aug. 5, 1999 | (JP) | H11-222989 |
| Aug. 6, 1999 | (JP) | H11-224523 |
| Aug. 6, 1999 | (JP) | H11-224558 |

(51) Int. Cl.
*A61B 1/04* (2006.01)

(52) U.S. Cl. .................... 600/117; 600/424
(58) Field of Classification Search ............... 600/101, 600/117, 118, 424, 407; 606/130; 128/897, 128/898; 324/207.12, 207.22
See application file for complete search history.

(56) References Cited

U.S. PATENT DOCUMENTS

| 5,558,091 | A | * | 9/1996 | Acker et al. ............... 600/424 |
| 5,729,129 | A | * | 3/1998 | Acker ................... 324/207.12 |
| 5,928,248 | A | * | 7/1999 | Acker ....................... 623/1.11 |
| 6,059,718 | A | * | 5/2000 | Taniguchi et al. .......... 600/117 |
| 6,341,231 | B1 | * | 1/2002 | Ferre et al. ................. 600/424 |
| 6,773,393 | B1 | * | 8/2004 | Taniguchi et al. .......... 600/117 |

* cited by examiner

*Primary Examiner*—John P. Leubecker
(74) *Attorney, Agent, or Firm*—Ostrolenk, Faber, Gerb & Soffen, LLP

(57) ABSTRACT

A shape of endoscope detecting apparatus in accordance with the present invention consists mainly of a shape detection unit, a marker, a location information of marker acquisition unit, and a display control unit. The shape detection unit detects the shape of a portion of an insertion unit of an endoscope inserted into a subject, and produces graphic data expressing the shape thereof. The marker is placed near a position on the subject at which the endoscope is inserted. The location information of marker acquisition unit acquires the location information of the marker. The display control unit graphically indicates on a display device the shape of the portion inserted into a body cavity, which is detected by the shape detection unit, using as a reference the location information of the marker acquired by the location information of marker acquisition unit.

12 Claims, 56 Drawing Sheets

24a

INTRACORPOREAL PORTION

EXTRACORPOREAL PORTION

ANUS MARKER COIL

EXAMPLE OF GRAPHICAL INDICATION ON MONITOR ACCORDING TO RELATED ART

INTRACORPOREAL PORTION

EXTRACORPOREAL PORTION

ANUS MARKER COIL

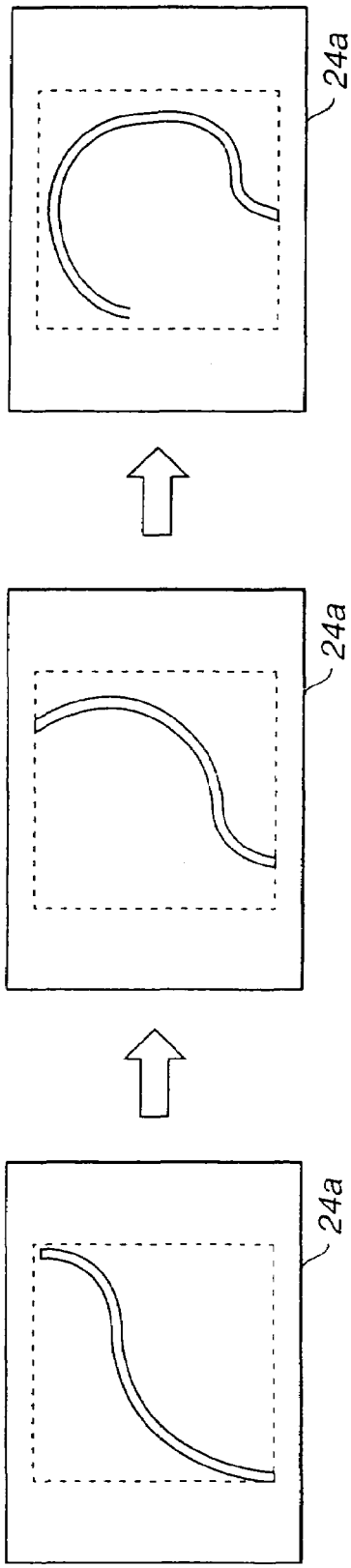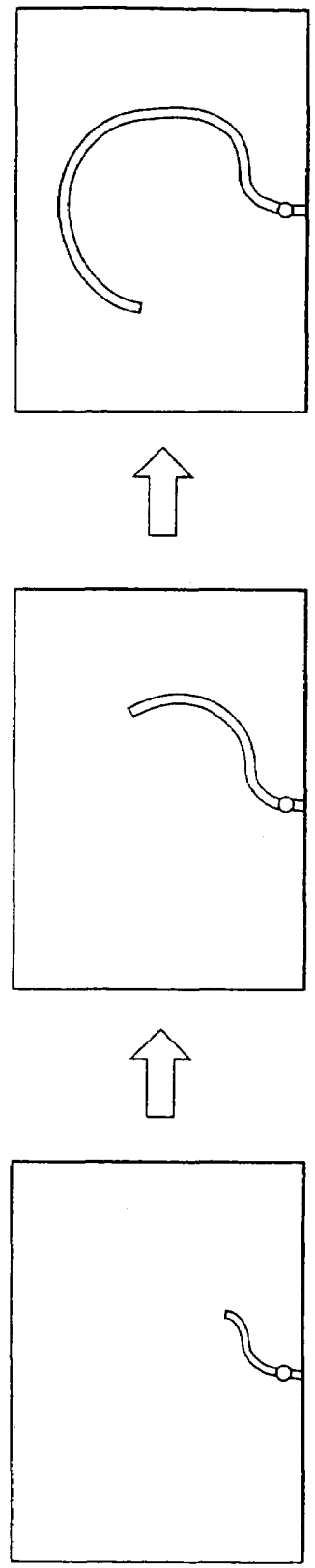
FIG.19A
FIG.19B
EXAMPLE OF GRAPHICAL INDICATION IN ACCORDANCE WITH RELATED ART

INITIAL DISPLAY SPACE

AUTOMATICALLY OPTIMIZED
DISPLAY SPACE

13 EXTRACORPOREAL COIL

13 EXTRACORPOREAL COIL
(REFERENCE POINT)

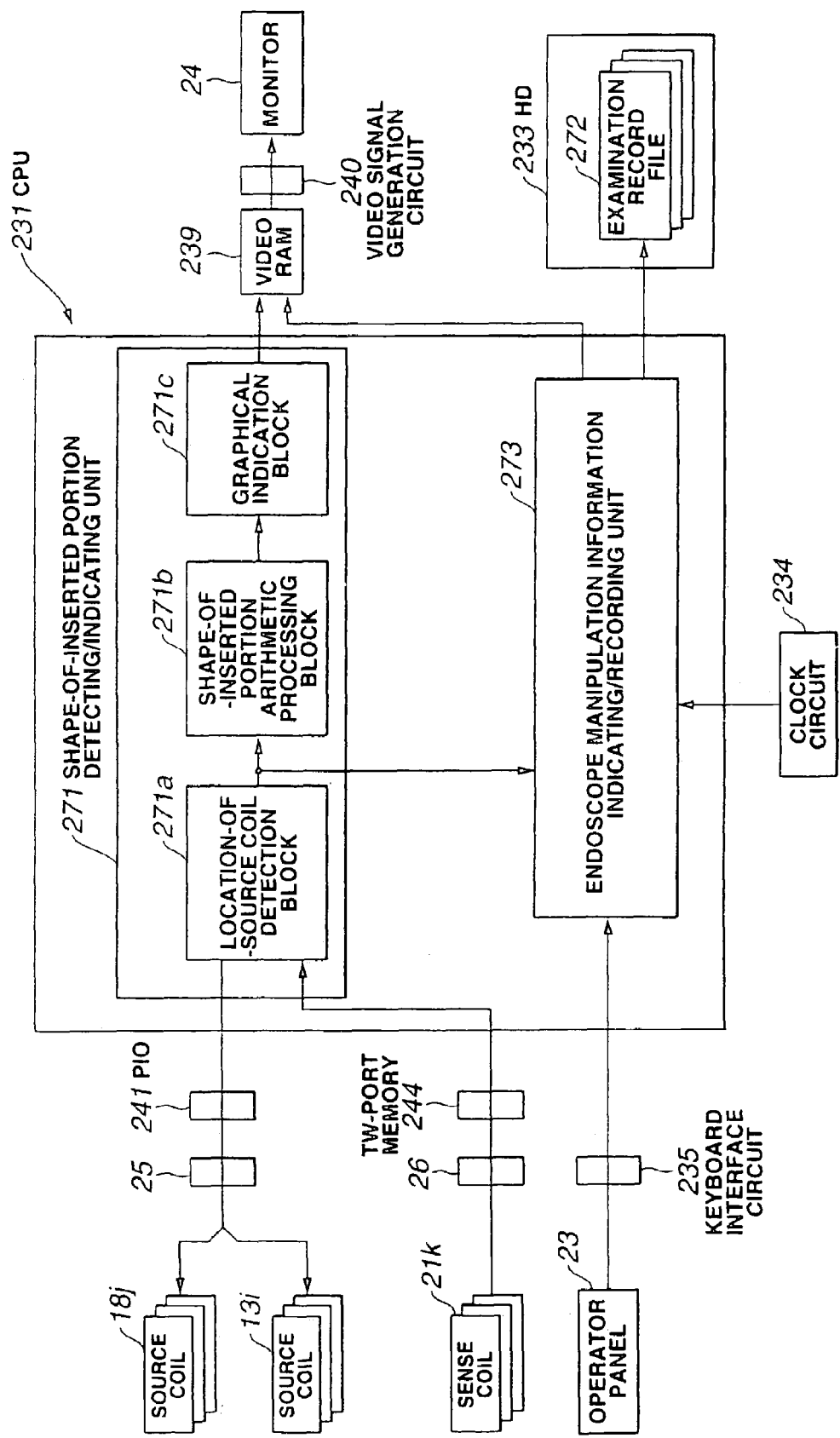

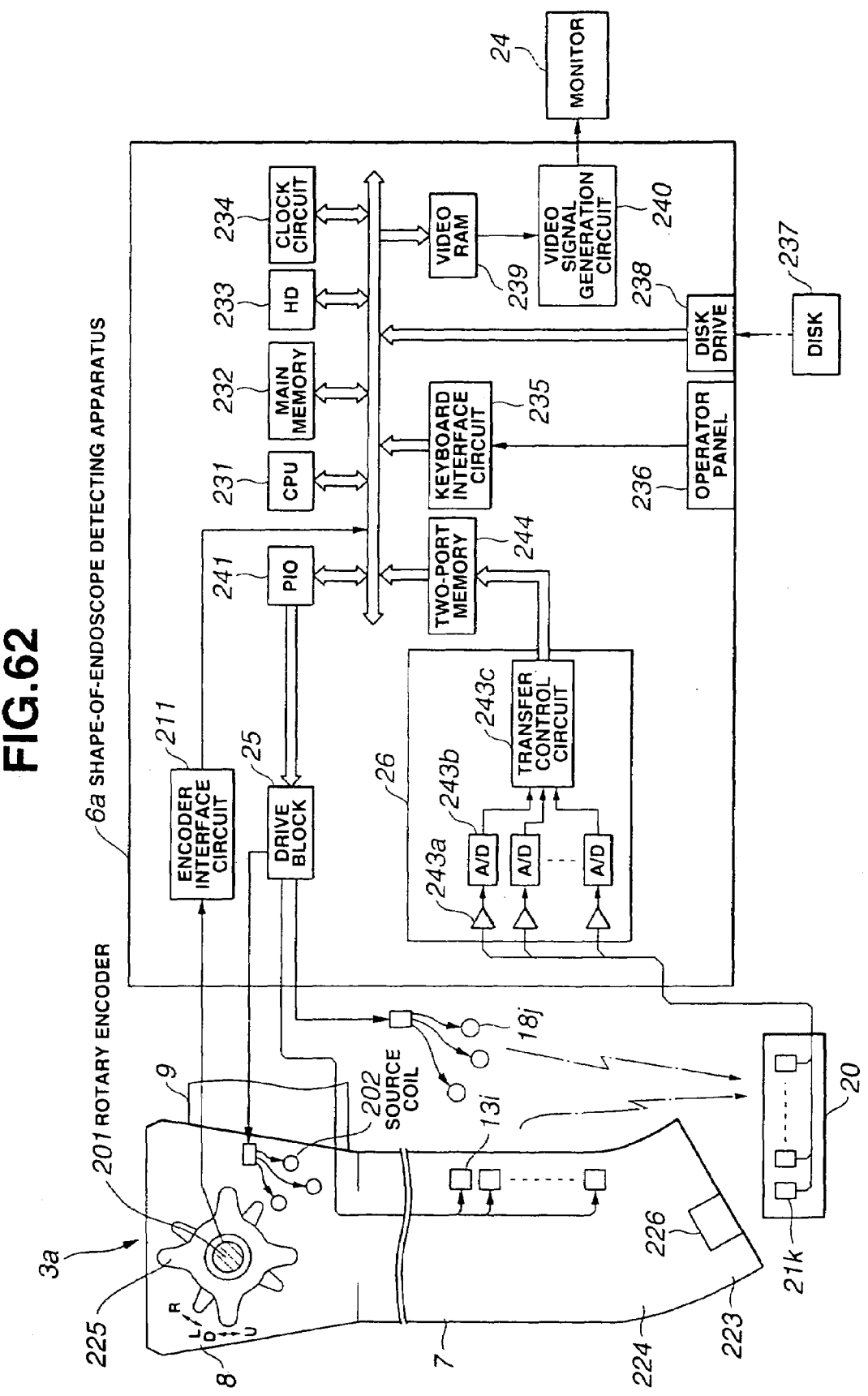

● DETECTED LOCATION OF COIL
○ INTERPOLATED POINT

411d

411e

FIG.71A      FIG.71B
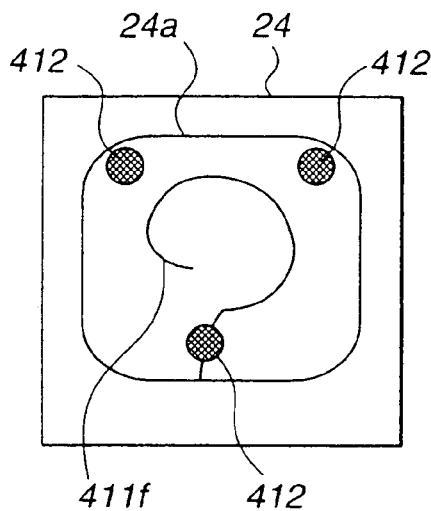 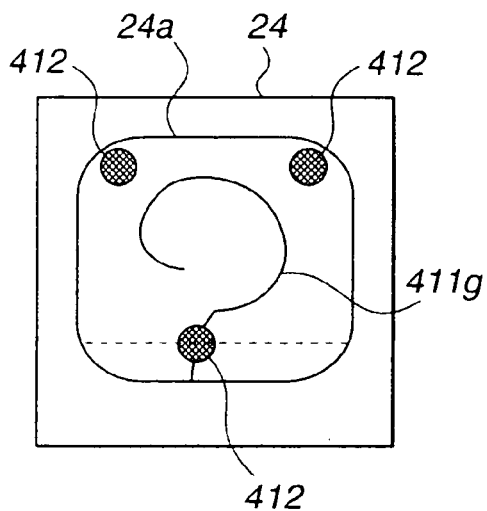
FIG.71C
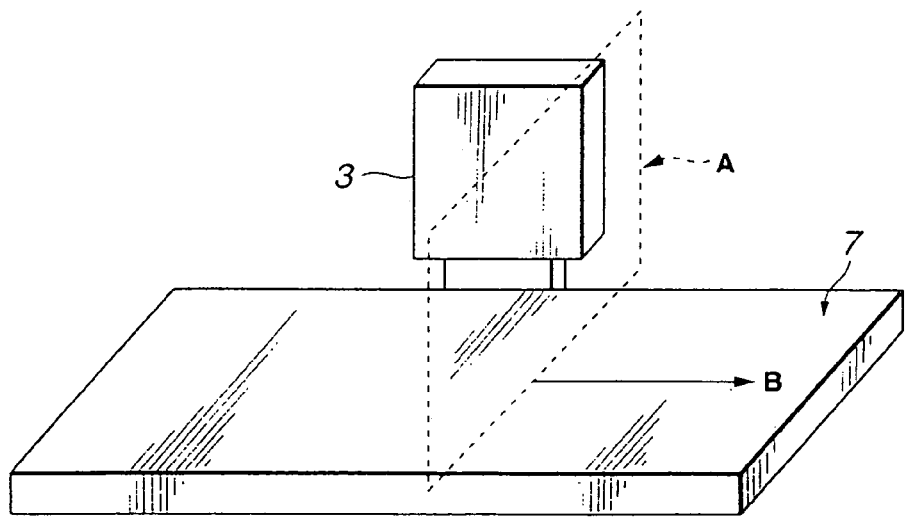

FIG.72
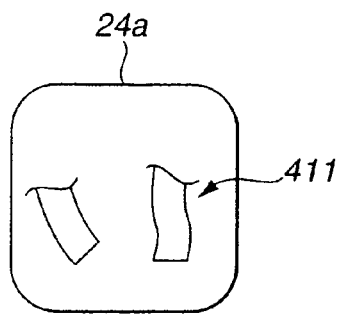
FIG.73A   FIG.73B
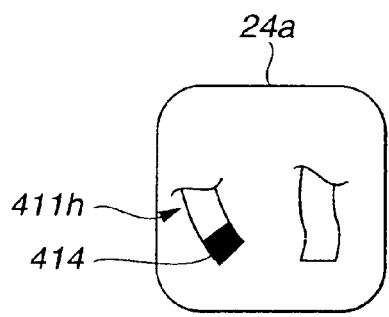 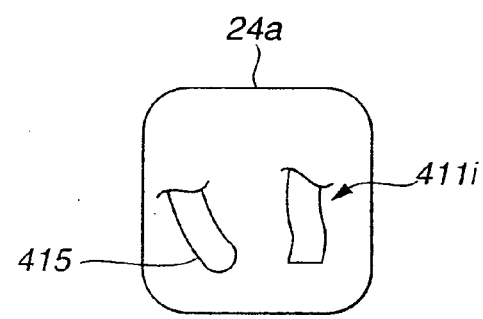
FIG.74
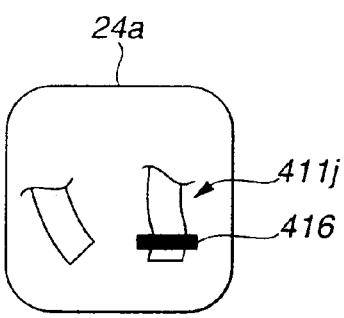
FIG.75
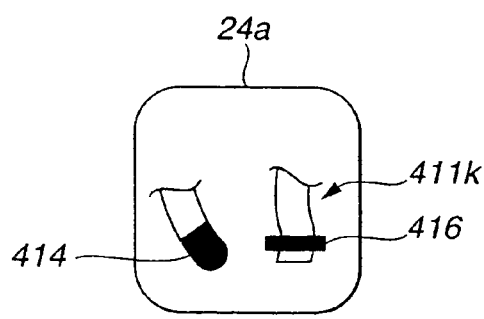

APPARATUS AND METHOD USING IT FOR DETECTING AND DISPLAYING FORM OF INSERTION PART OF ENDOSCOPE INSERTED INTO BODY CAVITY

This application is a divisional application of application Ser. No. 09/632,255, filed Aug. 3, 2000, now U.S. Pat. No. 6,773,393, which claims benefit of Japanese Application No. Hei 11-222858 filed in Japan on Aug. 5, 1999; Hei 11224523 filed in Japan on Aug. 6, 1999; Hei 11-222989 filed in Japan on Aug. 5, 1999; and Hei 11-224558 filed in Japan on Aug. 6, 1999, the contents of which are incorporated these references.

BACKGROUND OF THE INVENTION

1. Field of the Invention

The present invention relates to a shape-of-endoscope detecting apparatus for detecting the shape of a portion of an insertion unit of an endoscope inserted into a body cavity using magnetic fields, and for graphically indicating the shape in a characteristic manner, and to a shape-of-endoscope detecting method using the apparatus.

2. Related Art Statement

In general, endoscopes can be used to observe a lesion or perform required treatment on the lesion with an elongated and flexible insertion unit thereof inserted externally into a lumen in a human body.

Lumens including the large intestine and small intestine are tortuous. An operator of the endoscope is therefore unaware of to where the insertion unit of the endoscope has been inserted or what shape the insertion unit now assumes.

For inserting the insertion unit, the work of insertion, including angling of a bending portion of the insertion unit to follow the twists, bends, or turns of the lumen must be performed smoothly. From this viewpoint, if it can be learned where in a body cavity the distal part of the insertion unit is located or how the insertion unit is now bent, it would be convenient.

The present applicant has proposed in Japanese Patent Application No. 10-69075 an apparatus for detecting the inserted state of an endoscope or a catheter. The detecting apparatus can detect the inserted state of an insertion unit of the endoscope in a human body using magnetic fields without affecting the physiological condition of the human body. Using the apparatus, a user rotates the inserted portion of the endoscope so that he/she can easily observe the shape of the inserted portion.

However, according to the foregoing related art, the shape of the endoscope is not graphically indicated so that the user can clearly recognize the positional relationship among the endoscope, an intracorporeal region of a patient, and an extracorporeal region thereof. Consequently, the positional relationship between the endoscope and intracorporeal region is hard to ascertain. In other words, the position in a patient body to which the insertion unit of the endoscope has been inserted is hard to discern. Besides, if the insertion unit is located outside a detectable range, the position of the insertion unit may be detected incorrectly and the shape of the insertion unit may be graphically indicated to be at a set of coordinates defined on a monitor which is offset from the correct point.

Moreover, even if it can be discerned that the endoscope has been inserted into an intracorporeal region, the absolute length of the inserted portion of the endoscope is uncertain. This poses a problem in that it is hard to discern in what intracorporeal region in a patient, body the insertion unit of the endoscope lies. It is therefore desired to achieve an improved apparatus which helps to enable the insertion unit of the endoscope to be inserted smoothly.

Furthermore, according to the display method employed in the related art, even if a user sets a viewing point so that he/she can easily observe the shape of an inserted portion of an endoscope, once a patient changes his/her posture; there is no means enabling the user to determine the patient's posture. Since the position and angle of the graphically indicated shape of the insertion unit will vary with the patient's posture, the related art therefore has the drawback in that the user must re-set the viewing point. Incidentally, the viewing point is such that the shape of the inserted portion is graphically indicated while being depicted as if the inserted portion were viewed from the viewing point.

Moreover, the whole display screen is used to graphically indicate the shape of an endoscope. An area not of interest to the user, for example, an area outside the patient's body may also be graphically indicated. The user therefore has to identify on the screen the region he/she wants to observe carefully, for example, a patient's intracorporeal region.

Furthermore, the insertion unit of the endoscope to be inserted into a body cavity has a bending portion "made by concatenating a plurality of metallic bending pieces so that the pieces can freely rotate. Magnetic fields induced by source coils are affected by the pieces. When the bending portion is angled, the bending pieces move. Consequently, the shape of the bending portion changes. This disturbs the magnetic fields induced by the source coils, so that sets of coordinates specifying positions in the insertion unit cannot be defected accurately. This generates a concern that it may become impossible to graphically indicate on the screen the shape of the insertion unit with high precision.

Moreover, some source coils are incorporated in the bending portion: When the bending portion is angled, the source coils may hit the bending pieces or other structural elements of the insertion unit and thus interrupt bending. Moreover, there is a concern that those structural elements or the source coils themselves may be damaged.

In addition, for example, Japanese Unexamined Patent Application Publication No. 8-107875 has disclosed a shape-of-endoscope detecting apparatus including source coils that induce a magnetic field and are arranged at predetermined intervals, and sensing coils that sense a magnetic field and are located in the vicinity of the patient. Signals produced by the sensing coils are used to detect the location of the source coils. The location information of the source coils is used to calculate three-dimensional data representing the shape of the insertion unit. The three-dimensional data is transformed into two-dimensional data representing the shape of the insertion unit as if the insertion unit were viewed from a predetermined viewing point. The shape of the insertion unit is then graphically indicated on a monitor. The published patent application identified above has thus disclosed a technology for making it possible to determine the shape of an insertion unit that is not visible to the operator using the endoscope, and for improving the maneuverability of an endoscope.

The shape-of-endoscope detecting apparatus makes it possible to determine the shape of an inserted portion of the endoscope and thus contributes to improving the maneuverability of the endoscope. However, the insertion unit of the endoscope may be used for being inserted into a tortuous lumen. Therefore, when, for example, the bending portion is angled, it is not easy to determine, based on the shape of the insertion unit graphically indicated on the monitor, in which direction the distal part of the insertion unit will actually be moved. In other words, when the shape of the insertion portion is merely graphically indicated on the monitor, special expertise is needed to accurately determine the relationship between, the manipulation performed on the endoscope and the position of the inserted portion of the endoscope.

OBJECTS AND SUMMARY OF THE INVENTION

An object of the present invention is to provide a shape-of-endoscope detecting apparatus and method for graphically indicating the shape of an endoscope on a display screen so that a user can easily determine the inserted state of the endoscope when inserted into a lumen by viewing the shape of the endoscope graphically indicated on the display screen.

Another object of the present invention is to provide a shape-of-endoscope detecting apparatus enabling a user to observe the shape of a portion of an endoscope the user wants to observe carefully, and to provide a shape-of-endoscope detecting method using the apparatus. With the present invention, the shape of such portion is graphically indicated on a screen while being depicted as if the portion is being viewed from an easy-to-observe viewing point but is not affected by a change in the patient's posture.

Still another object of the present invention is to provide a shape-of-endoscope detecting apparatus with which it is possible to easily determine the relationship between the manipulation movements performed on an endoscope and the shape of the insertion unit of the endoscope by observing the shape of the insertion unit graphically indicated on a monitor without requiring special expertise, and a shape-of-endoscope detecting method using the apparatus.

Still another object of the present invention is to provide a shape-of-endoscope detecting apparatus for graphically indicating the shape of an insertion unit on a screen with high precision by accurately detecting sets of coordinates, which specify the locations of coils, without applying any stress to bending pieces or other structural elements of the endoscope.

Briefly, according to the present invention, a shape-of-endoscope detecting apparatus generally includes a shape detector, a marker, a marker locator, and a display controller. The shape detector detects the shape of a portion of an insertion unit of an endoscope inserted into a patient, and produces graphic data expressing the shape thereof. The marker is placed on the patient near a position on the patient at which the endoscope is inserted. The marker location acquires location information of the marker. The display controller graphically indicates the shape of the intracavitary portion of the insertion unit, which is detected by the shape detector, on a display using as a reference the location information of the marker acquired by the marker locator. A shape-of-endoscope detecting method generally includes a marker placing step, a marker location information acquiring step, a shape-of-inserted portion detecting step, and a display control step. At the marker placing step, a predetermined marker is placed on a patient near a region of the patient through which an endoscope is inserted. At the marker location information acquiring step, location information of the marker is acquired. At the shape-of-inserted portion detecting step, the shape of a portion of the insertion unit of the endoscope inserted into the subject is detected, and graphic data expressing the shape is produced. At the display control step, the location information of the marker acquired at the marker location information acquiring step is used as a reference to graphically indicate on a display the shape of the inserted portion detected at the shape-of-inserted portion detecting step.

BRIEF DESCRIPTION OF THE DRAWINGS

FIG. 1 to FIG. 6 relate to a first embodiment of the present invention;

FIG. 1 is an explanatory diagram showing the configuration of an endoscope system;

FIG. 2 is a block diagram showing the functional configuration of a shape-of-endoscope detecting apparatus shown in FIG. 1;

FIG. 3 shows the configuration of the shape-of-endoscope detecting apparatus;

FIG. 5 is a flowchart describing a process to be performed for graphically indicating the shape of an endoscope as shown in FIG. 4A;

FIG. 9A shows an example of a graphical indication of the shape of an endoscope displayed together with an absolute scale according to the third embodiment of the present invention;

FIG. 9B shows an example of a graphical indication of the shape of an endoscope displayed together with a square lattice (grid);

FIG. 11A to FIG. 12B are directed to a fourth embodiment of the present invention;

FIG. 11A is a perspective view showing an effective detectable range within which a coil unit can detect magnetic fields;

FIG. 12B shows an example of graphically indicating the shape of a portion of an endoscope lying within the effective detectable range on the screen of the monitor;

FIG. 13A to FIG. 16 are directed to a fifth embodiment of the present invention;

FIG. 13A shows an example in which the length of the inserted portion of an endoscope is displayed together with the shape of the endoscope;

FIG. 14 is a flowchart describing a process to be performed for determining the length of an inserted portion of an endoscope;

FIG. 15 is a flowchart describing a process to be performed for recording the length of the inserted portion of the endoscope;

FIG. 16 is a flowchart describing a process to be performed for determining an insertion time of the inserted position of the endoscope;

FIG. 17A to FIG. 18 are directed to a sixth embodiment of the present invention;

FIG. 17A shows an example in which an insertion ratio, that is, a ratio of the straight distance between the coordinates of a point specifying the distal position of an endoscope and a cut point to the length of the inserted portion of the endoscope together with the shape of the endoscope, wherein the insertion ratio is low;

FIG. 18 is a flowchart describing a process to be performed for calculating and indicating the insertion ratio;

FIG. 19A to FIG. 21 are directed to a seventh embodiment of the present invention;

FIG. 19A shows an example in which the shape of an endoscope is graphically indicated with a magnification which is varied according to the ratio of the length of the portion of the endoscope inserted into a patient's body cavity to the overall length of the endoscope;

FIG. 19B shows an example of the prior art in which the shape of an endoscope is graphically indicated at a constant magnification irrespective of the ratio of the length of the portion of the endoscope inserted into the patient's body cavity to the overall length of the endoscope;

FIG. 21 is a flowchart describing a process to be performed for indicating the shape of the endoscope as shown in FIG. 19A;

FIG. 22 to FIG. 42 are directed to an eighth embodiment of the present invention;

FIG. 22 shows the configuration of an endoscope system;

FIG. 23 is a block diagram illustrating the functional configuration of a shape-of-endoscope detecting apparatus shown in FIG. 22;

FIG. 25 is an explanatory diagram concerning the relationship between the marker plate and marks produced to represent the marker coils on the marker plate in a display unit;

FIG. 26 is a flowchart describing an example of a process to be performed for producing marks of FIG. 25;

FIG. 27 shows the marks produced according to the flowchart of FIG. 26;

FIG. 28A is an explanatory diagram illustrating the relationship between a detectable range of the apparatus and a display area;

FIG. 28B shows the positional relationship between the detectable range and the shape of an inserted portion of an endoscope according to the conventional apparatus;

FIG. 28C shows the shape of the endoscope as graphically indicated in the display area when the positional relationship shown in FIG. 28B is present in the conventional apparatus;

FIG. 29 is a flowchart describing a process to be performed in the shape-of-endoscope detecting apparatus of the present invention;

FIG. 30A shows a state in which the insertion portion of an endoscope begins to enter a range consistent with the display area;

FIG. 30B shows a state in which the graphical indication of the shape of the inserted portion of the endoscope is moved from the state shown in FIG. 30A to the center of the display area;

FIG. 30C shows the positional relationships between the detectable range, the display area, and the shape of the inserted portion of the endoscope;

FIG. 30D shows the shape of the inserted portion of the endoscope graphically indicated in the display area of a monitor;

FIG. 32 is a flowchart describing a process of extensible registration;

FIG. 33 is the first explanatory diagram relating to the process of extensible registration;

FIG. 34 is the second explanatory diagram relating to the process of extensible registration;

FIG. 35 is the third explanatory diagram relating to the process of extensible registration;

FIG. 36 is the fourth explanatory diagram relating to the process of extensible registration;

FIG. 37 is the fifth explanatory diagram relating to the process of extensible registration;

FIG. 38 is a flowchart describing another operation executed by the shape-of-endoscope detecting apparatus;

FIG. 39 is a flowchart describing a process for rotating the shape of an endoscope performed by the shape-of-endoscope detecting apparatus of the present invention;

FIG. 40 is an explanatory diagram for explaining the zoom feature with respect to the display marks representing the marker coils depending on the size of the patient;

FIG. 41 is a flowchart describing a process to be performed for zooming in on the shape of an endoscope on a monitor in relation to the displayed marks representing the marker coils;

FIG. 42 shows the positions of the display marks as referenced in the flowchart of FIG. 41;

FIG. 43 to FIG. 61 are directed to a ninth embodiment of the present invention;

FIG. 43 is an explanatory diagram showing the overall configuration of an endoscopic imaging system;

FIG. 44 is a block diagram showing the electrical circuitry of the shape-of-endoscope detecting apparatus shown in FIG. 43;

FIG. 45 shows an example of the arrangement of a plurality of buttons on an operator panel;

FIG. 46 shows an example of a graphical indication of the inserted portion of an endoscope as displayed on the screen of a monitor;

FIG. 47 shows another example of a graphical indication displayed on the screen of the monitor;

FIG. 48 is a block diagram showing the configuration of a CPU in accordance with the ninth embodiment;

FIG. 50 shows an example of a data structure for the examination record file;

FIG. 51 shows an example of an arrangement for a patient identification number entry window presented on a display screen;

FIG. 52 is a flowchart describing a process to be performed by an endoscopic manipulation information indicating/recording unit;

FIG. 53 is a flowchart describing a patient identification information acquisition process;

FIG. 54 is a flowchart describing an examination serial number acquisition process;

FIG. 55 is a flowchart describing a process for displaying information regarding an endoscopic manipulation operation;

FIG. 56 is a flowchart describing a process for displaying information regarding an angling operation performed on the endoscope;

FIG. 57 is a flowchart describing a process for displaying information regarding a rotation operation performed on the endoscope;

FIG. 58 is a flowchart describing a process for writing examination information into an examination record file;

FIG. 59 is a flowchart describing a process for writing angling information into an examination record file;

FIG. 60 is a flowchart describing a process for writing rotation information into an examination record file;

FIG. 61 is a flowchart describing a process for confirming the file size of an examination record;

FIG. 62 and FIG. 63 are directed to a tenth embodiment of the present invention;

FIG. 62 is a block diagram showing the electrical circuitry of a shape-of-endoscope detecting apparatus of the tenth embodiment;

FIG. 63 is a block diagram showing the configuration of a CPU in accordance with the tenth embodiment;

FIG. 64 to FIG. 76 are directed to an eleventh embodiment of the present invention;

FIG. 64 is an explanatory diagram of an arrangement of source coils in a shape detection endoscope;

FIG. 65 is a first explanatory diagram of a three-dimensional model employed in the graphical indication of a detected endoscope shape;

FIG. 66 is a flowchart describing a process to be performed for depicting the shape of the endoscope using the three-dimensional model of FIG. 65;

FIG. 67 is a second explanatory diagram of the three-dimensional model employed in the graphical indication of the shape of an endoscope;

FIG. 68 shows a model curve representing the shape of an inserted portion and constructed using the coordinates of interpolated points based on the coordinates of points specifying detected locations of source coils;

FIG. 69A shows a graphical image expressing the shape of an inserted portion and having a large thickness;

FIG. 69B shows a graphical image expressing the shape of an inserted portion and having a small thickness;

FIG. 69C shows a graphical image expressing the shape of an inserted portion and having a very small thickness;

FIG. 70A shows an example of a graphical image expressing the shape of an inserted portion in which the twisted state of the insertion unit is hard to discern;

FIG. 70B shows a graphical image expressing the shape of an inserted portion of the insertion unit in which the twisted state of the insertion unit is easy to discern;

FIG. 71A to FIG. 71C are explanatory diagrams for describing how a graphical image expressing the shape of an inserted portion is displayed in an anus cut mode;

FIG. 71A shows a graphical image expressing the shape of the whole insertion unit displayed on the display screen;

FIG. 71B shows a graphical image expressing the shape of the inserted portion of the insertion unit but not expressing a portion thereof located outside markers placed near the anus;

FIG. 71C is an explanatory diagram for explaining the portion of the insertion unit whose shape is not expressed in the graphical image shown in FIG. 71B;

FIG. 72 shows a normal graphical image displayed in a normal anus cut mode and indicating the distal position of the insertion unit and the rear position thereof near the anus;

FIG. 73A and FIG. 73B show graphical images having an identifier for helping to identify the position of the distal part of the insertion unit;

FIG. 73A shows an example of the identifier for helping to identify the distal position of the insertion unit;

FIG. 73B shows another example of the identifier for helping to identify the distal position of;

FIG. 74 shows a graphical image expressing the shape of the insertion unit and having an identifier for helping to identify the rear position of the insertion unit near the anus;

FIG. 75 shows a graphical image expressing the shape of the insertion unit and having both the identifiers for helping to identify the distal position of the insertion unit and the rear position thereof near the anus; and FIG. 76 is a flowchart describing a process to be performed for displaying a graphical image, which expresses the shape of the insertion unit, on the display screen.

DETAILED DESCRIPTION OF THE PREFERRED EMBODIMENTS

Figure 1:
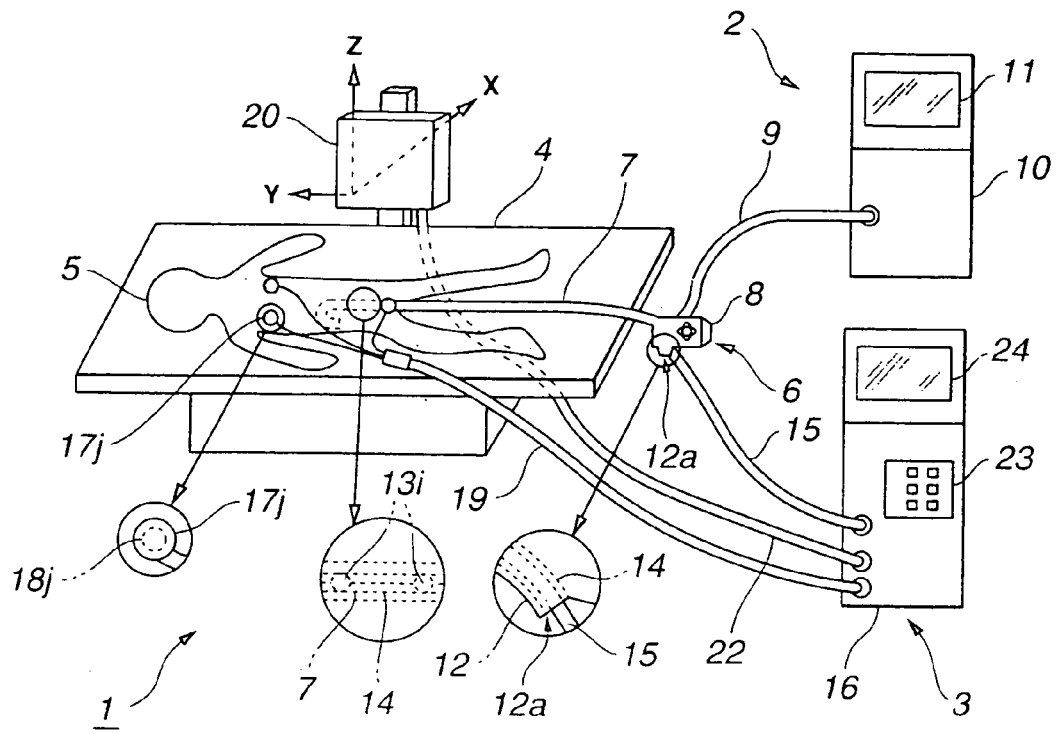

Referring to the drawings, the preferred embodiments of the present invention will be described below.

The first embodiment of the present invention will be described with reference to FIG. 1 through FIG. 5.

As shown in FIG. 1, an endoscope system 1 consists generally of an endoscopic imaging system 2 used for endoscopic examination, and a shape-of-endoscope detecting apparatus 3 used to assist in endoscopic examination and to detect the shape of an inserted portion of an insertion unit of an endoscope. The shape-of-endoscope detecting apparatus 3 is used in an endoscopic examination procedure to assist the insertion of an insertion unit 7 of an electronic endoscope 6 is inserted into a body cavity of a patient 5 lying down on an examination table. Hereinafter, the electronic endoscope 6 may be referred to as an endoscope, and the shape of the inserted portion of the insertion unit of the endoscope may be referred to as the shape of the endoscope.

The elongated insertion unit 7 of the electronic endoscope 6 is flexible. An operation unit 8 having an angling knob is provided at the rear end of the insertion unit 7. A universal cord 9 is extended from the operation unit 8 and coupled to a video imaging system or a video processor 10.

The electronic endoscope 6 has a light guide passed through it. Illumination light emanating from a light source unit, which is not shown, in the video processor 10 is propagated over the light guide. The illumination light propagated over the light guide is emitted through an illumination window affixed in the distal part of the insertion unit 7, for illuminating an object to be examined, such as a lesion or the like. Light reflected from the illuminated lesion, for example, being examined forms an image through an objective lens affixed in an observation window adjacent to the illumination window. The image is converged on an imaging device located on the image plane. The optical image converged on the imaging device is converted into an electrical signal, whereby photoelectric conversion is achieved.

The electrical signal is processed by a video signal processing unit in the video processor 10, whereby a standard video signal is produced. Consequently, the image of the object is displayed on an image viewing monitor 11 connected to the video processor 10.

The electronic endoscope 6 has a forceps channel 12 extending therethrough. A probe 14 having, for example, twelve source coils 13a, 13b, etc., and 13l (hereinafter referred to generically as 13i) serving as magnetic field generation elements is passed into the insertion unit 7 from an insertion port 12a of the forceps channel 12. The plurality of source coils 13i is thus incorporated in the insertion unit 7.

In the probe 14, the distal source coil 13a is succeeded by the other source coils 13b to 13l arranged orderly at predetermined intervals. When the probe 14 is provided in the forceps channel 12, the distal source coil 13a is located at a known position in the distal part of the insertion unit 7. The other succeeding source coils 13b to 13l are also located at known positions along the length of the insertion unit 7.

A source cable 15 serving as a high-frequency signal propagating means is extended from the rear end of the probe 14. A connector attached to the rear end of the source cable 15 is coupled to the main unit 16 of the shape-of-endoscope detecting apparatus 3 so that the connector can be uncoupled freely. A high-frequency signal serving as a driving signal is applied from the main unit 16 to the source coils 13i over the source cable 15, whereby the source coils 13i radiate electromagnetic waves including magnetic fields.

In the present embodiment, the probe 14 having the source coils, 13i is inserted in the forceps channel 12 in the electronic endoscope 6, whereby the source coils 13i are incorporated in the insertion unit 7 of the electronic endoscope 6. Alternatively, the source coils 13i may be incorporated directly in the insertion unit 7 of the electronic endoscope 6.

Moreover, three markers i.e., first, second, and third markers 17a, 17b, and 17c (hereinafter referred to generically as 17j), are placed on the skin of the patient 5, far example, near the anus and on the left side and right side of the patient's torso. The markers 17j have marker coils 18j each serving as a magnetic field generation element.

A marker cable bundle 19 that is a bundle of marker cables extending from the markers 17j and serving as a high frequency signal propagating means has, like the source cable 15 extending from the probe accommodating the source coils 13i, a connector attached to the rear end thereof. The connector is coupled to the main unit 16 of the shape of-endoscope detecting apparatus 3 so that the connector can be uncoupled freely.

A high-frequency signal serving as a driving signal is applied from the main unit 16 to the marker coils 18j via the marker cable bundle 19, whereby the marker coils 18j radiate electromagnetic waves including magnetic fields.

Figure 2:
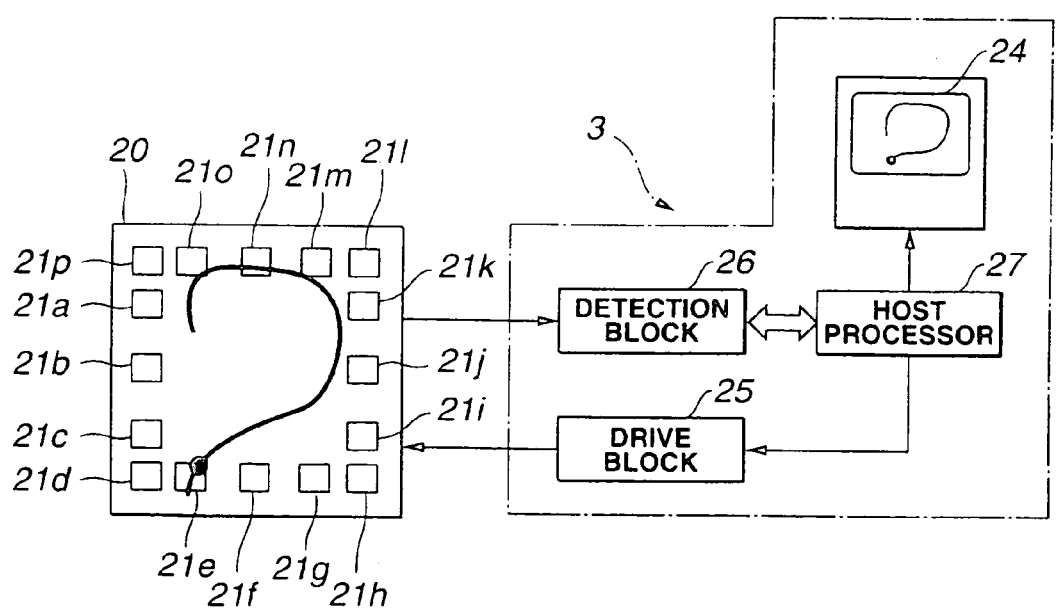

For magnetically detecting the locations of the source coils 13i or markers 17j, a coil unit 20 serving as a shape detecting means and a marker locator is installed at a predetermined position near the patient 5. A plurality of sensor coils, for example, 16 sensor coils 21a, 21b, etc., and 21p (hereinafter referred to generically as 21k) that are single-core coils are, as shown in FIG. 2, located at known positions in the coil unit 20.

The sensor coils 21k detect magnetic signals generated by the source coils 13i or markers 17j. The detected signals are propagated to the main unit 16 over a sensor cable 22 serving as a detected signal propagating means.

The main unit 16 has an operator panel 23, a keyboard, or an operator pad a user uses to operate the apparatus. Moreover, the main unit 16 has a monitor 24 serving as a display means on which a detected shape of the endoscope is, graphically indicated.

A description will now be provided of the detailed configuration of the shape-of-endoscope detecting apparatus 3.

As shown in FIG. 2, the shape-of-endoscope detecting apparatus 3 consists generally of a drive block 25, a detection block 26, and a host processor 27. The drive block 25 drives the source coils 13i and marker coils 18j. The detection block 26 detects signals received by the sensor coils 21k. The host processor 27 processes the signals detected by the detection block 26.

Figure 3:
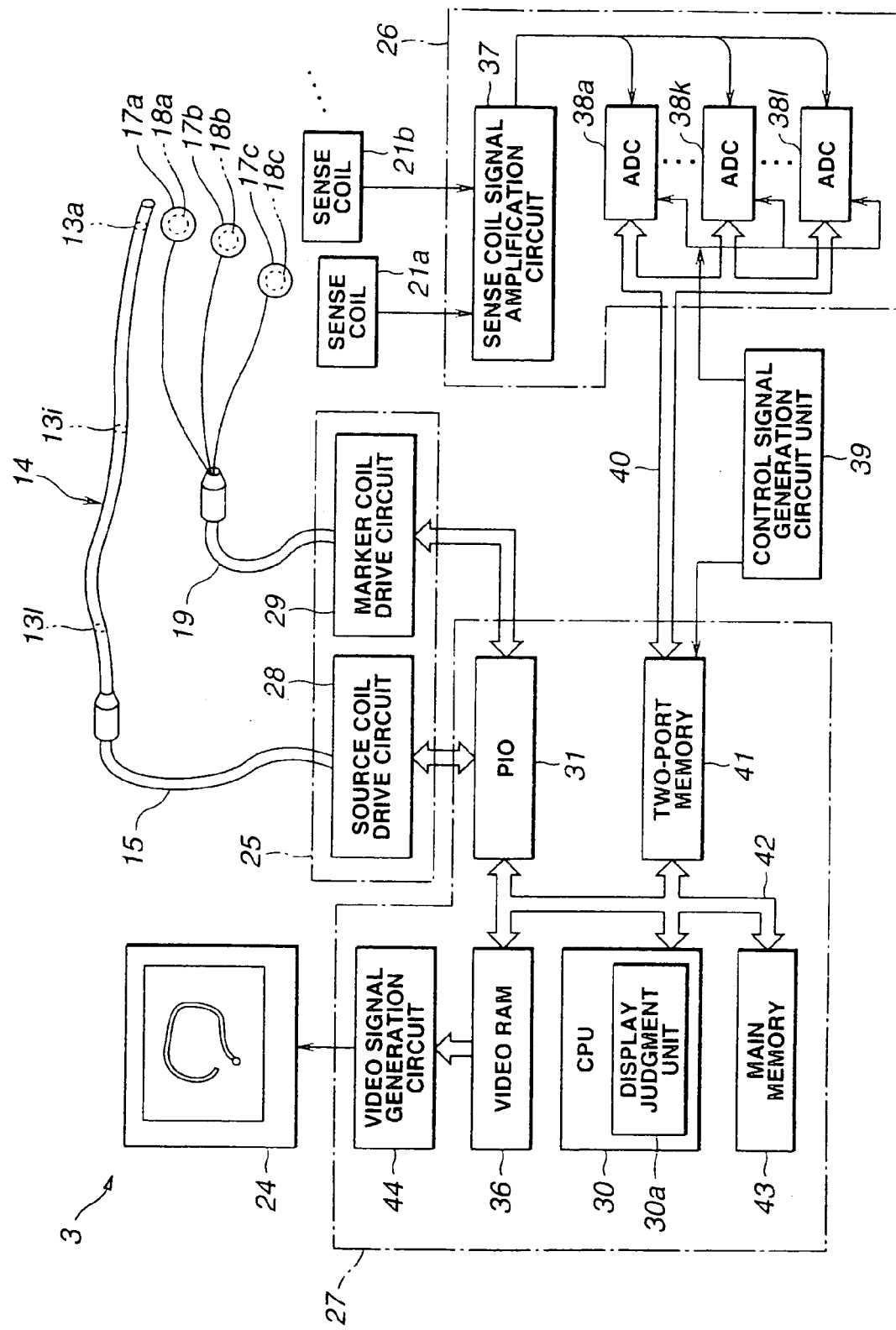

As shown in FIG. 3, the twelve source coils 13i for inducing magnetic fields are, as mentioned above, arranged in the probe 14, which is inserted into the insertion unit 7 of the electronic endoscope 6, at predetermined intervals along the length of the insertion unit 7. The source coils 13i are connected to a source coil drive circuit 28 included in the drive block 25 for producing twelve driving signals of different high frequencies.

The marker coils 18j are connected to a marker coil drive circuit 29 included in the drive block 25 for producing three driving signals of mutually different high frequencies different from the high frequencies of the source coil driving signals.

The source coil drive circuit 28 drives the source coils 13i with driving signals of currents of sine waves having mutually different frequencies. The frequencies of the driving signals are set based on driving frequency setting data (which may be referred to hereinafter as driving frequency data) stored in a driving frequency setting data storage means or a driving frequency setting data memory means, which is not shown, included in the source coil drive circuit 28.

The marker coil drive circuit 29 drives the marker coils 18j with driving signals of currents of sine waves having mutually different frequencies. The frequencies of the driving signals are set based on driving frequency setting data (which may be referred to hereinafter as driving frequency data) stored in a driving frequency setting data storage means or driving frequency setting data memory means, which is not shown, included in the marker coil drive circuit 29.

The driving frequency data is stored in the driving frequency data storage means (not shown) in the source coil drive circuit 28 or marker coil drive circuit 29 via a parallel input/output circuit (PIO) 31 by means of a central processing unit (hereinafter CPU) 30 included in the host processor 27 for performing arithmetic operations to detect the shape of an endoscope.

The sensor coils 21k are connected to a sensor coil signal amplification circuit 37 included in the detection block 26.

As shown in FIG. 3, the detection block 26 consists of the sensor coil signal amplification circuit 37, and analog-to-digital converters (hereinafter referred to as A/D converters) 38a to 38l (hereinafter referred to generically as 38k). Feeble signals detected by the sensor coils 21k are amplified by the sensor coil signal amplification circuit 37, and converted into digital data, which is structured to be readable by the host processor 27, by the A/D converters 38k. The digital data is transferred to a two-port memory 41 via a local data bus 40 and stored therein in response to a control signal sent from a control signal generation circuit 39.

The CPU 30 reads the digital data stored in the two-port memory 41 via an internal bus 42 in response to a control signal sent from the control signal generation circuit 39. The CPU 30 uses a main memory 43 to sample frequencies exhibited by the digital data (through fast Fourier transform (FFT)). The CPU 30 then separates and extracts as magnetic field information the frequency components of the digital data exhibiting the same frequencies as the frequencies of the driving signals applied to the source coils 13i and marker coils 18j. The CPU 30 then uses the magnetic field information from the digital data to calculate coordinates in a three-dimensional space specifying the locations of the source coils 13i incorporated in the insertion unit 7 of the electronic endoscope 6 and of the marker coils 18j.

The calculated coordinates specifying the locations of the source coils 13i are used to interpolate the coordinates of intermediate points or to estimate the inserted state of the insertion unit 7 of the electronic endoscope 6. Graphic data expressing the shape of the endoscope is then produced and output to a video RAM 36. The calculated coordinates specifying the locations of the marker coils 18j are used to produce graphic data representing the marker coils 18j. The graphic data is then output to the video RAM 36.

The graphic data is output from the video RAM 36 to a video signal generation circuit 44 and converted into an analog video signal. The analog video signal is output to the monitor 24.

Figure 4A:
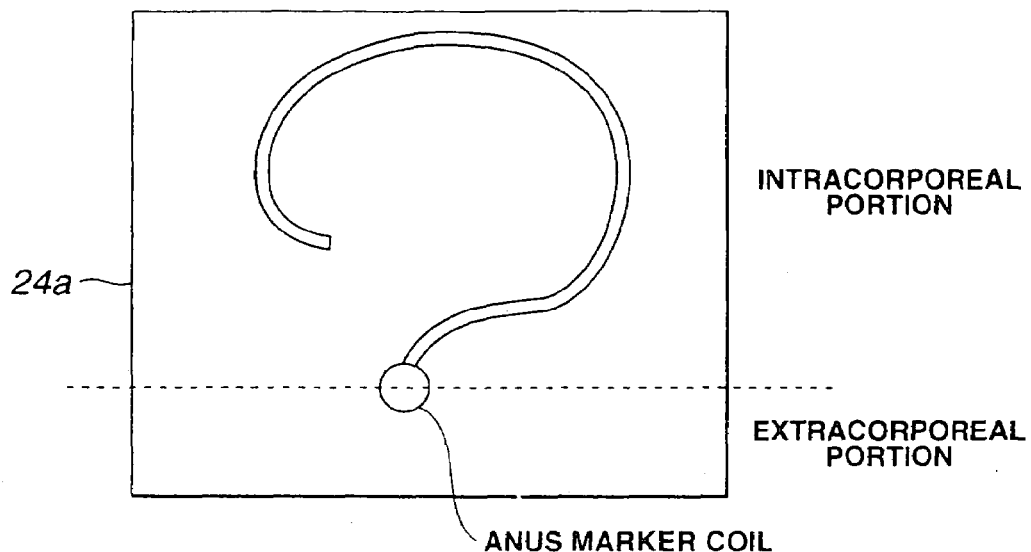
FIG. 4A shows the shape of an endoscope graphically indicated on the screen of a monitor according to the first embodiment.
Figure 5:
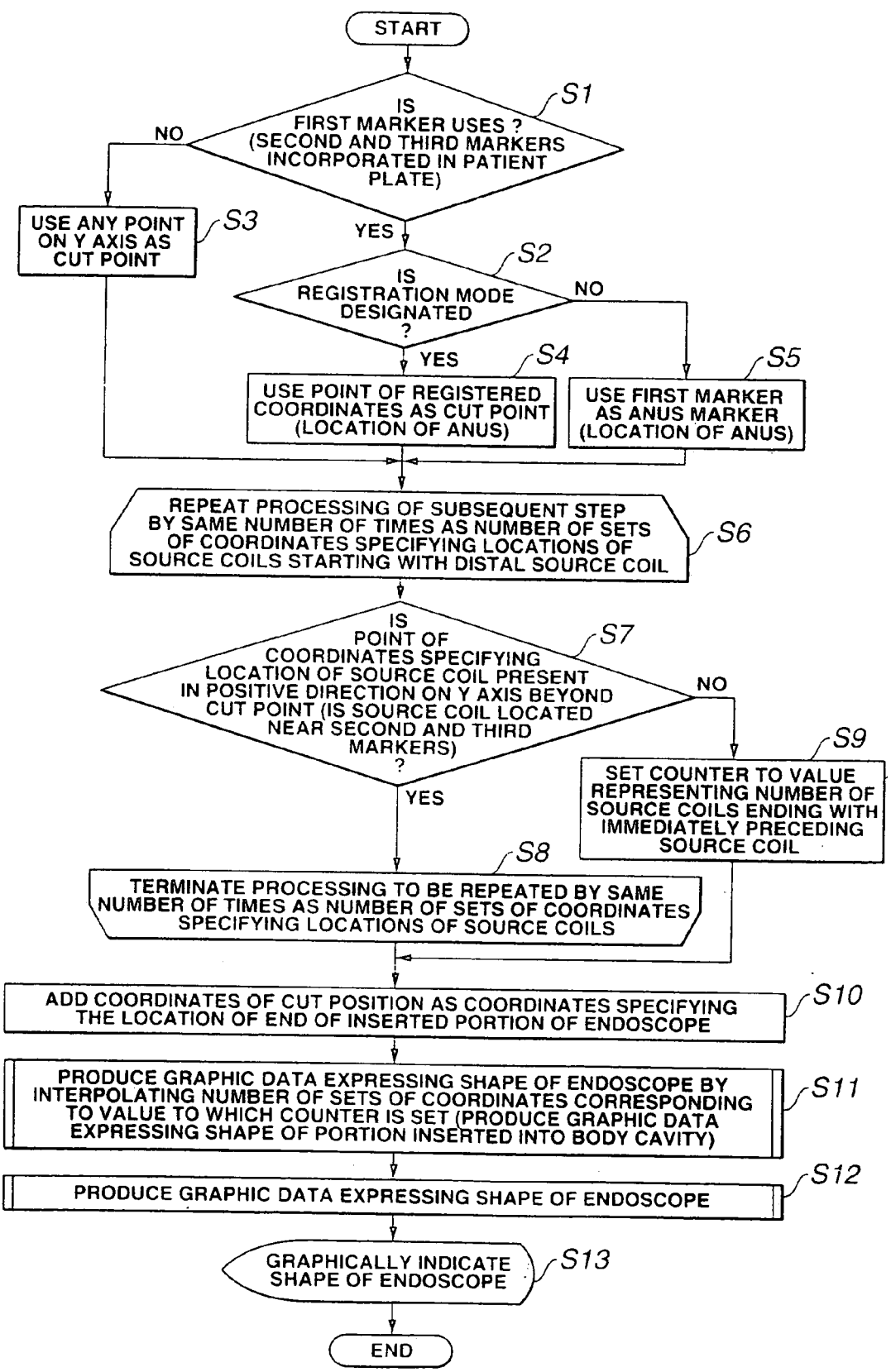

According to the present embodiment, a process as described in FIG. 5 is performed on the coordinates specifying the locations of the source coils 13i incorporated in the insertion unit 7. Specifically, it is judged through comparison whether or not the Y coordinates (in the positive direction along the Y axis) for the source coil locations are larger than a Y coordinate included in coordinates specifying the location of the anus through which the insertion unit 7 is inserted into the patient's body. Herein, the coordinates of the point specifying the location of the anus is regarded as a reference point. Coordinates of points specifying the various locations along the endoscope judged to be located inside the patient's body are used to produce graphic data expressing the shape of the inserted portion of the endoscope (which may be referred to as the shape of the endoscope). The graphic data is then output to the video RAM 36, whereby the shape of the portion of the endoscope inserted into the human body is graphically indicated as shown in FIG. 4A.

The CPU 30 included in the host processor 27 shown in FIG. 3 in turn includes a display judgment unit 30a. The display judgment unit 30a stores the Y coordinate contained in the coordinates specifying the location of the anus as a reference value into, for example, an internal register. The Y coordinates contained in the coordinates specifying the locations of the source coils 13i are compared with the reference value held in the register in order to judge whether the source coils 13i lie inside or outside the patient's body. The coordinates specifying the locations of the source coils 13i judged to lie inside the patient's body by the display judgment unit 30a are used to interpolate intermediate points, whereby graphic data expressing the shape of the insertion unit 7 is produced.

The orientation of the axes referenced by the coordinates (X, Y, Z) in a three dimensional space are defined, for example, as shown in FIG. 1. Specifically, the Y axis extends in parallel with the longitudinal direction of the examination table 4. The direction towards the head of the patient 5 is the positive direction along the Y axis. When the shape of the endoscope is graphically indicated on a screen 24a of the monitor as shown in FIG. 4A or FIG. 4B, an upward direction included in vertical directions corresponds to the positive direction along the Y axis, while the horizontal direction on the screen 24a corresponds to a direction along the X axis.

The coordinates specifying the locations of the marker coils 18j and containing Y coordinates equal to or larger than the Y coordinate contained in the coordinates specifying the location of the anus are used to produce graphic data, which are then output to the video RAM 36.

For example, the first marker coil 18a may be placed at the location of the anus and used as an anus marker coil. In this case, the shape of the intracorporeal portion of the endoscope is graphically indicated together with the anus marker coil on the screen 24a as shown in FIG. 4A.

Figure 4B:
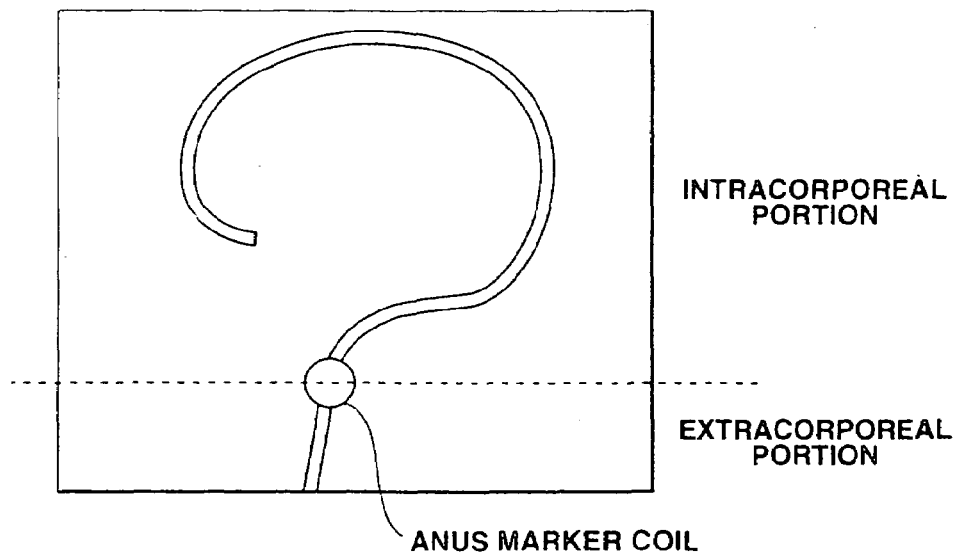
FIG. 4B shows the shape of an endoscope graphically indicated on a monitor as know in the prior art.

In the prior art, the shape of the endoscope is graphically indicated together with the anus marker coil as shown in FIG. 4B. In this display mode, the shape of the intracorporeal portion of the endoscope actually lying inside the patient's body is indiscernible. According to the present embodiment, the shape of only the intracorporeal portion of the endoscope located beyond the anus marker coil is graphically indicated as shown in FIG. 4A. In other words, the shape of the portion of the insertion unit of the endoscope actually inserted into the patient's body is indicated explicitly graphically, while portions of the endoscope located outside the patient's body is omitted from the display.

In short, it may be said that the shape of the endoscope is graphically indicated in a cut mode. The cut mode is such that the extracorporeal portion of the insertion unit of the endoscope is regarded as a portion whose shape need not be graphically indicated, and is therefore cut from the graphical indication of the endoscope shape.

FIG. 5 is a flowchart describing the process to be performed in the shape-of-endoscope detecting apparatus 3 for graphically indicating the shape of the endoscope as shown in FIG. 4A.

When the shape-of-endoscope detecting apparatus 3 is activated, it is judged at step S1 whether the first marker coil is used. In FIG. 5, for the sake of brevity, the first through third marker coils are referred to as the first through third markers. If it is judged that the first marker coil is used, it is judged at step S2 whether a registration mode in which coordinates specifying the location of the patient's anus are stored or registered as registered coordinates has been designated.

If it is judged at step S1 that the first marker coil is not used, the process moves on to step S3, in which any point along the Y axis is regarded as a cut point. The process then advances to step S6. The cut point may be set to any point other than the coordinates of a point specifying the location of the patient's anus. However, since the cut point is used to discriminate the intracorporeal portion of the endoscope from the extracorporeal portion thereof, the cut point is preferably set to the coordinates of the point specifying the location of the patient's anus.

If the registration mode is designated at step S2, the process advances to step S4. The registered coordinates are adopted as the coordinates of the cut point (specifying the location of the patient's anus), whereupon the process then proceeds to step S6. In contrast, if the registration mode is not designated at step S2, the process proceeds to step S5, in which the first marker coil (first marker in FIG. 5) is designated as an anus marker coil (the location of the anus), and the process then proceeds to step S6.

The process described from step S6 through step S8 is repeated the same number of times as the number of sets of coordinates specifying the locations of the source coils 13$i$ incorporated in the insertion unit 7, starting with the distal-most source coil. This process will be described below.

It is judged at step S7 from the coordinates specifying the location of a point on the endoscope (that is, the location of each of the source coils 13$i$ incorporated in the endoscope) whether or not the point on the endoscope is located near the second and third marker coils positioned on the patient's torso as described above with reference to FIG. 1, or whether or not the coordinates of the point is located in the positive direction along the Y axis. If so, this step is repeated for the coordinates specifying the location of the next source coil 13($i$+1). If the judgment of step S7 is negative, the process passes from this step to step S9. At step S9, a counter is set to a value representing the number of source coils judged affirmatively in step S7, ending" with the immediately preceding one.

To be more specific, source coils meeting the condition set for step S7 are located inside the patient's body beyond the anus. A source coil not meeting the condition is located outside the patient's body. The counter is set to a value representing the number, of source coils meeting the condition, ending with the immediately preceding source coil. The process then passes to step S10, and the coordinates of the cut point are added as the coordinates specifying the proximal end position of the intracorporeal portion of the endoscope.

Next, the process proceeds to step S11. The number of sets of coordinates corresponding to the value to which the counter is set is used to interpolate the coordinates of intermediate points and to produce graphic data expressing the shape of the endoscope. Thus, the shape of the portion inserted into the body cavity is produced. The process then proceeds to step S12, where the graphic data expressing the shape of the endoscope is produced. At step S13, the shape of the endoscope is graphically indicated on the screen of the monitor 24 according to the graphic data. The process is then terminated.

According to the present embodiment, it is judged with respect to the reference point such as the coordinates of a point specifying the location of the anus marker coil placed at the anus whether the source coils provided in the insertion unit lie inside a patient's body. The shape of the portion of the insertion unit accommodating the source coils judged to lie inside the patient's body is graphically indicated as the shape of the inserted portion. An operator can therefore easily determine the shape of the portion of the insertion unit inserted into the patient's body upon viewing the graphical indication representing the shape of the endoscope displayed on the screen of the monitor.

Interpolation may be performed between adjacent sets of coordinates specifying the locations of source coils up to the first source coil judged to lie outside a patient's body. Thus, the detected shape may be the shape of a portion of the endoscope ending at a point along the endoscope coincident with the patient's anus.

Moreover, the display mode in which the shape of the endoscope is graphically indicated on the screen of the monitor 24 is not limited to the one shown in FIG. 4A. The display mode shown in FIG. 6A or FIG. 6B may also be used. Specifically, when the insertion unit 7 is not inserted into a patient's body, if the shape of the insertion unit 7 is graphically indicated together with the anus marker coil by detecting the locations of the source coils, the distal part of the insertion unit 7 may be, as shown in FIG. 6A, graphically indicated below the anus marker coil.

In this variant, if it is judged that the distal-most source coil located in the distal-most part of the insertion unit 7 is located below the anus marker coil along the Y-axis direction, that is, located outside a patient's body, it is judged that the insertion unit has not been inserted into a patient's body. Thus the anus marker coil alone is graphically indicated as shown in FIG. 6B.

Figure 6A:
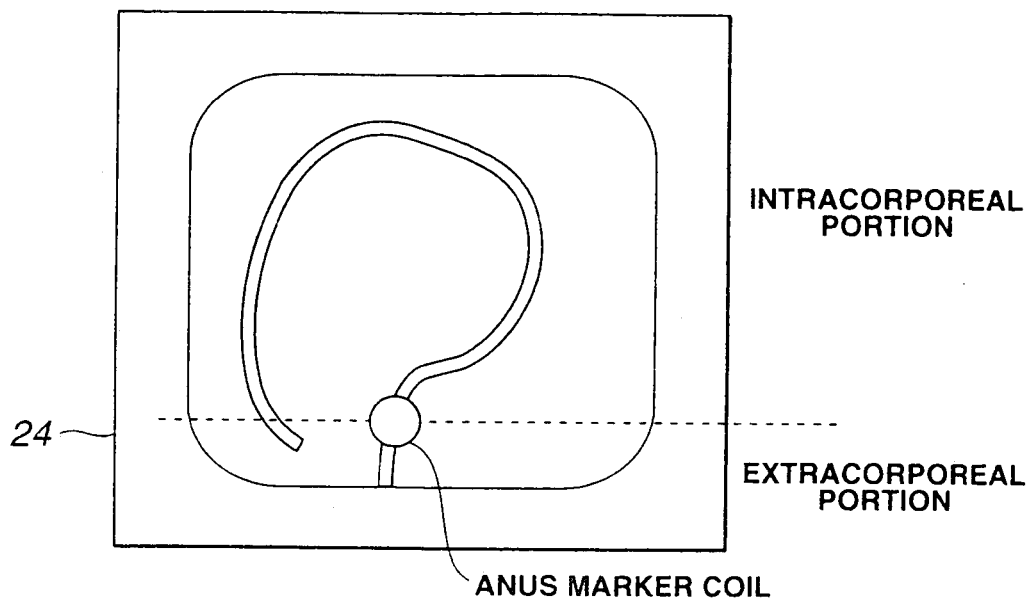
FIG. 6A shows an example of the shape of an endoscope graphically indicated on a monitor.
Figure 6B:
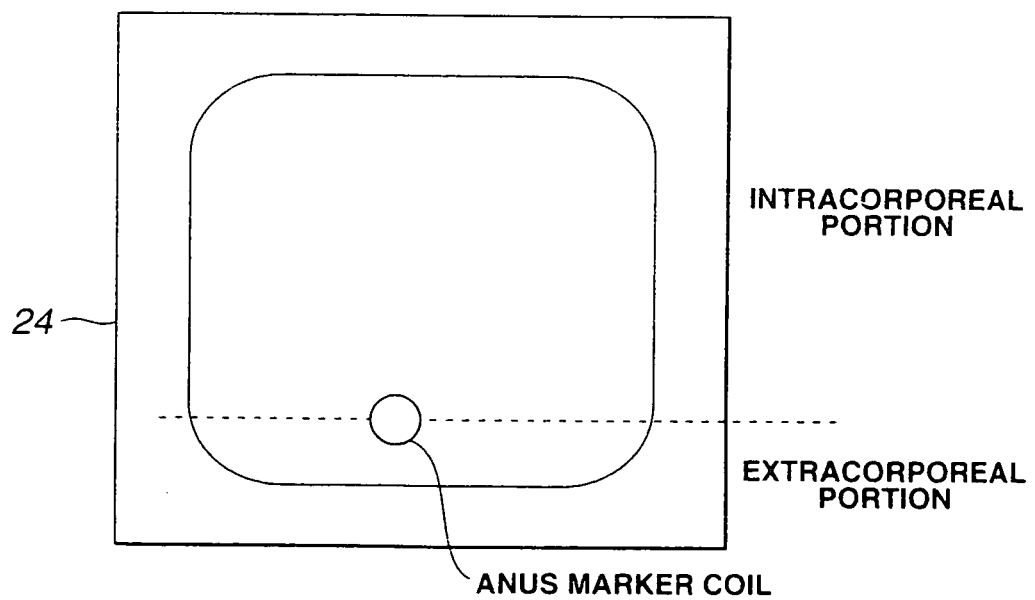
FIG. 6B shows an example of an alternative graphical indication when the shape of the endoscope as shown in FIG. 6A is detected.

In short, when the insertion unit 7 is inserted into a patient's body, it is not possible for the insertion unit 7 to be shaped as is graphically indicated in FIG. 6A. If such a configuration is detected, therefore, it is judged that the insertion unit 7 has not been inserted into a patient's body. Therefore, the shape of the insertion unit is not graphically indicated, and only the anus marker coil alone is graphically indicated.

The precision in detecting the location of a source coil outside a detectable range of the coil unit 20 is low, which will be described later. An incorrect location may be detected as the location of such a source coil. According to a variant of the present invention, therefore, the shape of the endoscope can be prevented from being graphically indicated to be located at the coordinates of incorrect points defined on the screen. At this time, the anus marker coil is located within the detectable range of the coil unit 20. The anus marker coil is therefore graphically indicated.

Another display mode may be used in which a patient plate is substituted for the anus marker coil and is used to set the reference point. The patient plate may be constructed using three source coils. In this display mode, the portion of the endoscope whose shape need not be graphically indicated is defined by using as a reference point any of the coordinates calculated using the patient plate. Thus, the shape of the endoscope may be graphically indicated (depicted).

Moreover, according to the embodiment described above, the Y coordinate (for example; Yref) contained in the coordinates specifying the location of the anus through which the insertion unit is inserted into a patient's body is used as a criterion for judgment. The Y coordinate contained in the coordinates specifying the detected location of a source coil 13*i* (for example, Yi) assumes a positive value larger than that contained in the coordinates of the reference point (Yi-Yref). Alternatively, the Z coordinates contained in the coordinates specifying the locations of markers placed on the patient's skin surface may be referenced to make the judgment.

According to the present embodiment, only the shape of an intracorporeal portion of the endoscope is graphically indicated. Alternatively, as will be described later with respect to another embodiment with reference to FIG. 9A and FIG. 9B, the shape of an intracorporeal portion of the endoscope and the shape of an extracorporeal portion thereof may be graphically indicated using different colors so that they can be discriminated from each other.

Figure 7:
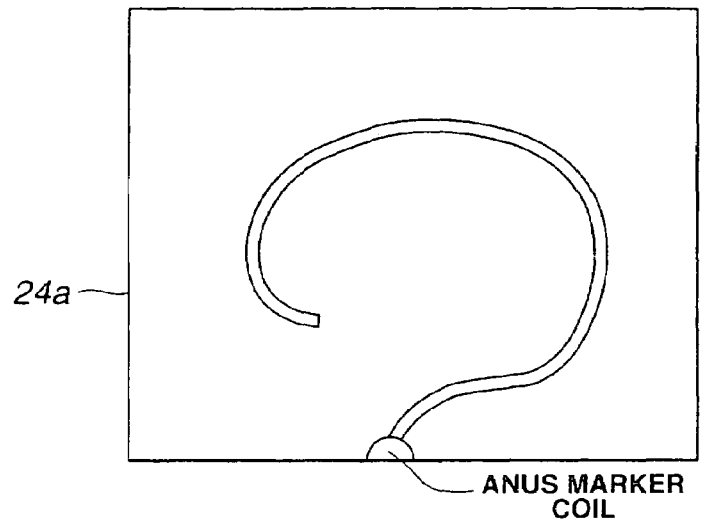
FIG. 7 shows another example of a graphically indication of the shape of an endoscope according to a second embodiment of the present invention.
Figure 8A:
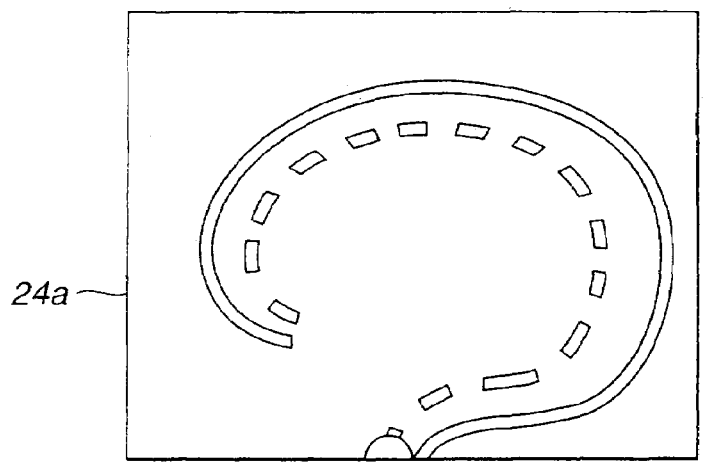
FIG. 8A shows an example of an enlarged graphical indication of the endoscope shape shown in FIG. 7.
Figure 8B:
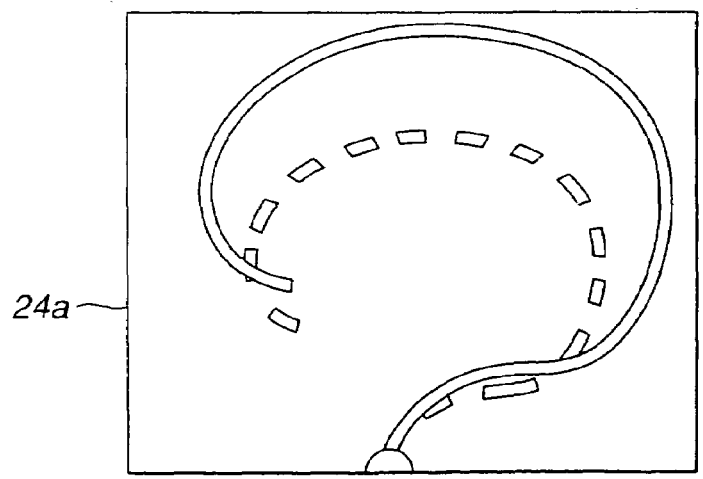
FIG. 8B shows an example of an enlarged graphical indication of the shape of an endoscope which effectively utilizes the screen on a monitor.

The second embodiment of the present invention will now be described with reference to FIG. 7 through FIG. 8B.

According to the first embodiment, when the shape of the endoscope is graphically indicated, part of the display screen is not used effectively. In the present embodiment, as shown in FIG. 7, the location of the anus marker coil at which the insertion unit is inserted into a patient's body is indicated on the lower margin of the display screen of the monitor 24. In other words, the present embodiment includes a means for displacing the coordinates of points located on the dashed line in FIG. 4A, FIG. 4B, FIG. 6A, and FIG. 6B, which represents the border between the intracorporeal and extracorporeal portions of the endoscope, to the lower margin of the display screen.

Thus, to most effectively use the display screen, the apparatus includes the capability to graphically indicate the shape of the endoscope in enlargement. Although it may be possible to enlarge the shape of the endoscope with the center of the screen shown in FIG. 7 (a non-enlarged view) as the center of enlargement, in this case, as apparent from the difference shown in FIG. 8A between the non-enlarged shape of the endoscope shown with the dashed lines and the enlarged shape thereof shown with the solid line image, part of the enlarged shape of the endoscope is not graphically indicated on the screen. For this reason, when the shape of the endoscope is graphically indicated in enlargement, a graphic representing the anus marker coil placed at the anus is used as the center of enlargement. In other words, the coordinates of a point specifying the location of the anus is used as a reference point for enlargement. Consequently, the drawback underlying the display mode shown in FIG. 8A is overcome. Consequently, the shape of the whole intracorporeal portion of the endoscope is graphically indicated in enlargement as shown in FIG. 8B.

As mentioned above, when the shape of an intracorporeal portion of the endoscope is graphically indicated, the coordinates of the point specifying the position on the patient's body at which the insertion unit is inserted into the patient's body is displaced to be aligned with the lower margin of the display space in a screen. In this manner, only the required view of the shape of the inserted portion of the endoscope is graphically indicated with a reduced sense of unnaturalness than would be present without the displacement of the coordinates of the reference point into the lower margin.

Moreover, the shape of the endoscope is graphically indicated in enlargement, with the coordinates of a point specifying the position on a patient's body at which the insertion unit is inserted into the patient's body is used as a reference point for enlargement. The display space in a screen can therefore be effectively utilized. Moreover, the shape of the endoscope can be graphically indicated without cutting off a portion of the shape of the inserted portion thereof.

The third embodiment of the present invention will now be described with reference to FIG. 9A and FIG. 9B.

Figure 9A:
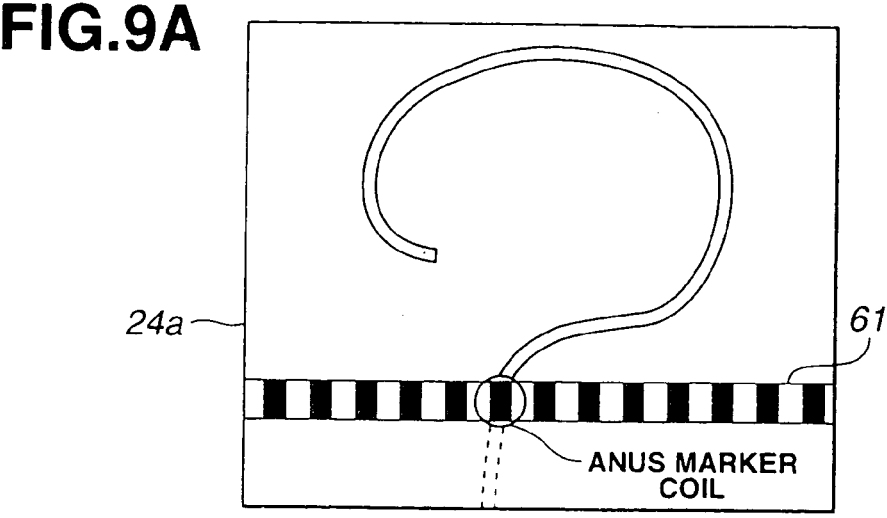
FIG. 9A and FIG. 9B are explanatory diagrams relating to a third embodiment of the present invention.

According to the present embodiment, a superimposing function is provided for, as shown in FIG. 9A, superimposing a stripe 61 on the shape of the endoscope shown in FIG. 4A on the screen 24*a* of the monitor. The stripe 61 serves as an absolute scale and extends horizontally to pass through the coordinates of a point specifying the location of the patient's anus. The width of the white and black bands forming the stripe 61 is set to a certain value, for example, 10 mm. The shape of the endoscope is graphically indicated together with the stripe 61 serving as an absolute scale. Thus, the position of each part of the endoscope whose shape is graphically indicated can be determined more easily than when the stripe 61 is not present.

Figure 9B:
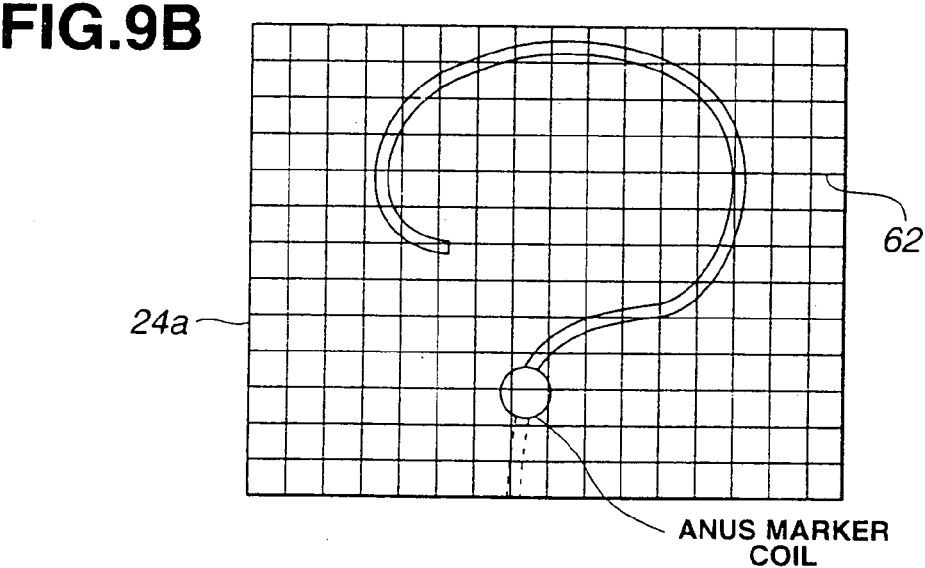

For making it possible to more easily determine the position of each part of the endoscope whose shape is graphically indicated, a grid 62 may be, as shown in FIG. 9B, displayed on the screen 24 of the monitor. The vertical and lateral widths of each of the squares in the grid 62 are, for example, 10 mm. Thus, the position of any part of the endoscope such as the distal part of the insertion unit 7 inserted into a body cavity can be determined even more easily than when the stripe 61 is used as shown in FIG. 9A.

Consequently, the actual position in a body cavity at which the distal part of the insertion unit 7 inserted into the body cavity is located can be readily discerned. The endoscope can thus be manipulated smoothly in order to insert it into a deeper region in the patient's body cavity. Moreover, if the endoscope is looped in the body cavity, the diameter of the loop can be determined more easily than when the absolute scale or any other scale is not displayed.

Although, the width of the bands constituting the stripe or the vertical or lateral width of the squares constituting the grid are set to 10 mm according to the present embodiment, such widths are not limited to 10 mm. As long as the bands or squares can be distinguished from one another, the width may be set to any value. Moreover, the width may be selectable from among several values using the operator panel (see, e.g., reference numeral 23 in FIG. 1) or the like. Otherwise, the width may be settable to any operator-desired value. Moreover, either the stripe or the grid can be selected or both may be displayed at the same time on the display screen.

Also, for graphically indicating the shape of the endoscope, the shape of only the portion of the endoscope inserted into a patient's body may be shown. In the present embodiment, for example, the shape of an intracorporeal portion of the endoscope and the shape of an extracorporeal portion thereof bordered by a graphic representation of the anus marker coil are graphically indicated using different colors. In FIGS. 9A and 9B, the different colors are indicated using two different types of lines, i.e., a solid line and a dashed line. Thus, the shape of the intracorporeal portion of the endoscope (solid line) is distinguishable from the shape of the extracorporeal portion thereof (dashed line).

For example, in an early stage of insertion in which the insertion unit has just been inserted through the patient's anus, the extracorporeal portion of the insertion unit should be indicated graphically. This is because compared with the case when only the shape of the intracorporeal portion is graphically indicated, the direction of insertion or the like can be more easily determined. Therefore, at least in the early stages of insertion, the shape of the intracorporeal portion of the endoscope and the shape of the extracorporeal portion thereof may be graphically indicated using different colors so that they can be easily differentiated from each other.

Figure 10:
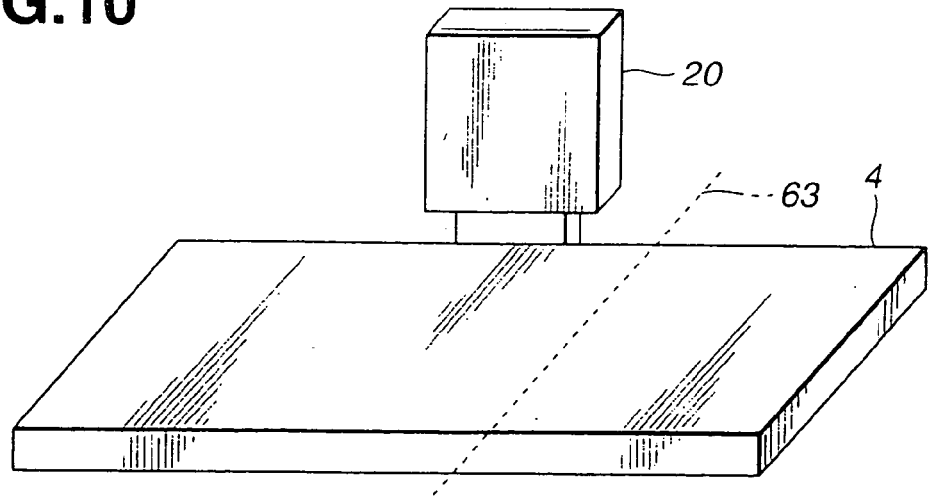
FIG. 10 shows a case where a reference line is used instead of a marker coil to distinguish an intracorporeal portion of the endoscope from an extracorporeal portion thereof.

What serves as the border between the intracorporeal portion of the endoscope and the extracorporeal portion thereof is not limited to the presence of an anus marker coil. In particular, the anus marker coil may optionally be omitted. Specifically, as shown in FIG. 10, a reference line 63 (in which the Y coordinate contained in the coordinates specifying the location of any point on the line is a constant) may be drawn at a position on the examination table 4 at which the anus of a patient is usually positioned. In other words, a patient is asked to lie down on the examination table 4 so that his/her anus will be positioned on the reference line 63. The Y coordinate contained in the coordinates specifying the location of any point on the reference line 63 is used as a reference to distinguish the shape of the intracorporeal portion of the endoscope from the shape of the extracorporeal portion thereof.

The fourth embodiment of the present invention will now be described with reference to FIG. 11A through FIG. 12B.

Figure 11A:
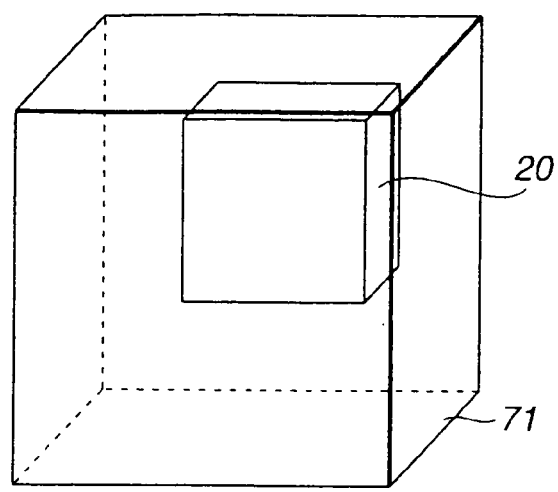
Figure 11B:
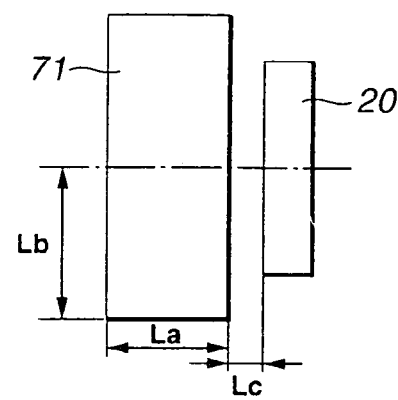
FIG. 11B is a plan view or side view showing the effective detectable range of FIG. 1A.

According to the present embodiment, the shape of the endoscope is graphically indicated with respect to an effective detectable range 71 for the coil unit 20 shown in FIG. 11A and FIG. 11B.

Specifically, the effective detectable range 71 is shaped like a parallelepiped. The depth of the detectable range 71 extends to a distance La from the face of the coil unit 20, and the width and length of the detectable range 71 extends to double the distance Lb from the center of the coil unit 20. However, the range within the distance Lc from the face of the coil unit 20 that is also within the distance La is not included in the depth of the detectable range 71. This is because a signal detected by the sensor coil $21k$ may contain an error depending on the size of the sensor coil or a signal detected thereby may cause an overflow error. (i.e., a computer calculation error).

Figure 12A:
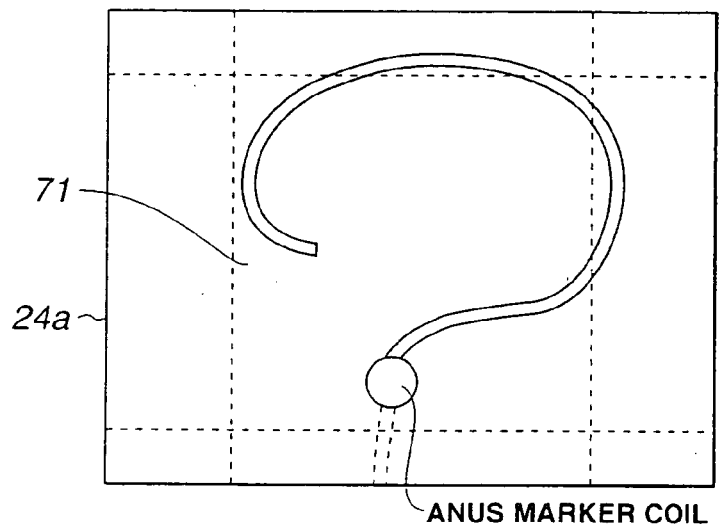
FIG. 12A shows a practical example of indicating the effective detectable range together with the shape of an endoscope on the screen of a monitor.

As shown in FIG. 12A, the effective detectable range 71 may be indicated with dashed lines together with the shape of the endoscope on the screen 24a of the monitor. This display mode helps an operator discern the portion of the endoscope whose shape is graphically indicated which the apparatus is capable of detecting with high precision.

Figure 12B:
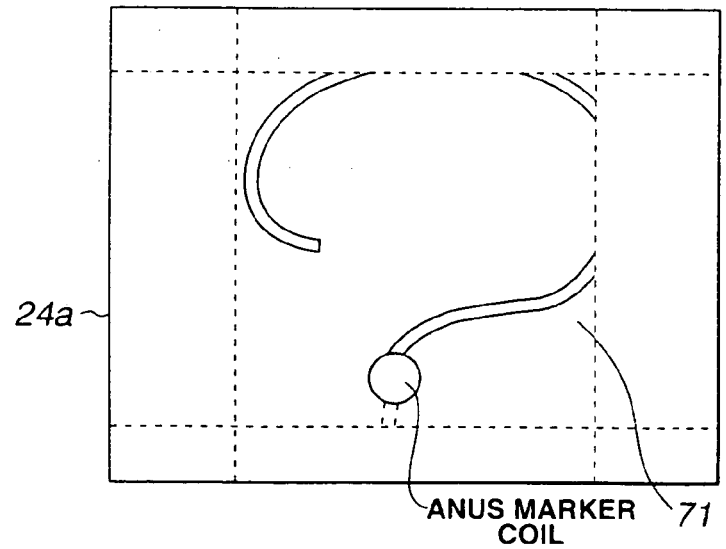

As shown in FIG. 12B, while the effective detectable range 71 may be indicated with dashed lines, the shape of the portion of the endoscope lying within the effectively detectable range 71 only may be graphically indicated. Additionally, the shape of the intracorporeal portion of the endoscope and the shape of the extracorporeal portion thereof may be graphically indicated using different colors.

This display mode makes it possible to graphically indicate the shape of the endoscope with little distortion, due to the high precision of detection in the effective detectable range. A user can therefore discern the shape of the portion of the endoscope detected with high precision (FIG. 12A), or alternatively is enabled to view the shape of only that portion (FIG. 12B).

The fifth embodiment of the present invention will now be described with reference to FIG. 13A through FIG. 16.

Figure 13A:
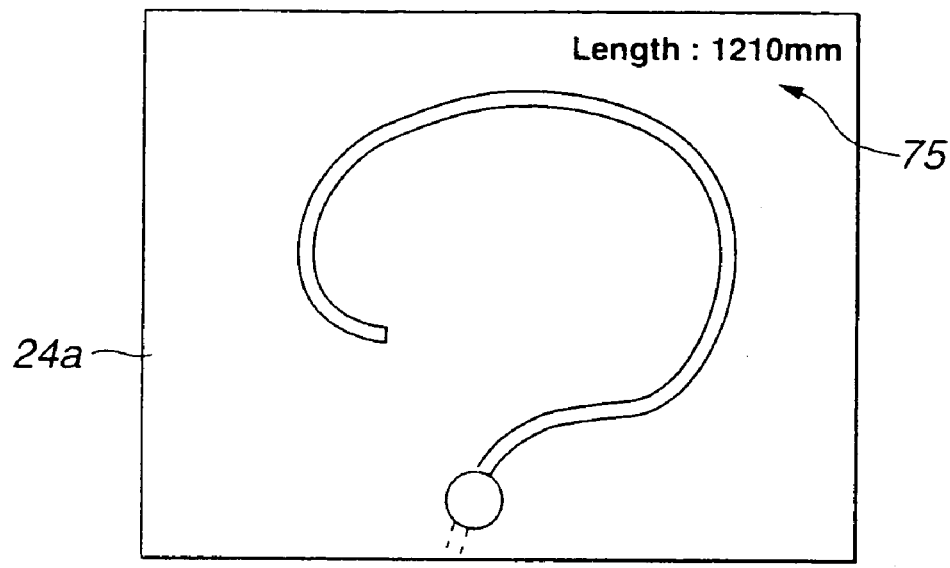

The present embodiment has, in addition to the same components as those of the first embodiment, for example, a length-of-inserted portion indicator for indicating the length of an inserted portion of the endoscope. Specifically, a length-of-inserted portion indicator region 75 is, for example, as shown in FIG. 13A, defined on the screen 24a of the monitor, in which the length of the inserted portion is displayed in the space 75.

Figure 14:
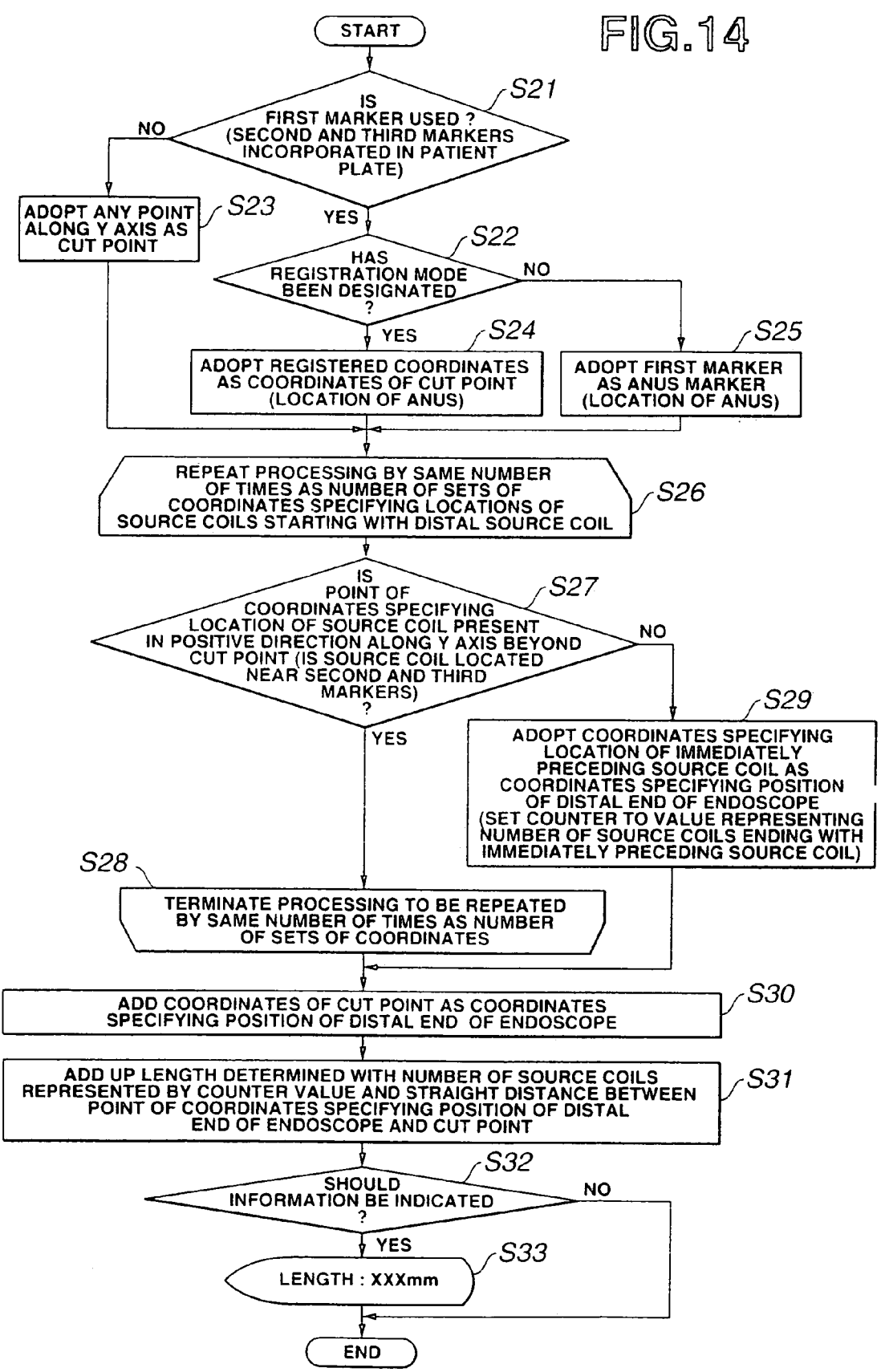

FIG. 14 describes a process performed in the shape-of-endoscope detecting apparatus for indicating the length of an inserted portion of the endoscope.

When the shape-of-endoscope detecting apparatus 3 is activated, it is judged at step S21 whether the first marker coil is used (similarly to the discussion of FIG. 5, for the sake of brevity, the first through third marker coils are referred to as the first through third markers).

If the first marker coil is used, the process proceeds to step S22. It is judged whether a registration mode, in which coordinates specifying the location of the anus are stored or registered as registered coordinates, has been designated. In contrast, if it is judged at step S21 that the first marker coil is not used, the process proceeds to step S23, in which any point along the Y axis is regarded as a cut point, and the process then proceeds to step S26.

The cut point may be set to the coordinates of any point other than the coordinates of a point specifying the location of the patient's anus. However, the cut point is preferably set to the coordinates of the point specifying the location of the patient's anus because it is used to distinguish the intracorporeal portion of the endoscope from the extracorporeal portion thereof.

If the registration mode has been designated at step S22, the process proceeds to step S24. The registered coordinates are used as the coordinates of the cut point (the location of the anus), and the process proceeds to step S26. In contrast, if the registration mode has not been designated at step S22, the process proceeds to step S25, wherein the first marker coil (the first marker in FIG. 14) is designated as an anus marker coil (the location of the anus), and the process then proceeds to step S26.

The process described from steps S26 through S28 is repeated the same number of times as the number of sets of estimated coordinates specifying the locations of the source coils incorporated in the insertion unit 7. The process is repeatedly performed on coordinates specifying the location of each of the source coils starting with the distal-most source coil. This process will be described below.

At step S27, it is judged from the coordinates specifying the location of a source coil whether or not the source coil is located near the second and third marker coils positioned on the patient's torso as described hereinabove, that is, the coordinates of the point is located in the positive direction along the Y axis beyond the cut point. If so, the judgment is repeated for the coordinates specifying the location of the next source coil. If the condition set for step S27 is not met, the process proceeds from step S27 to step S29. At step S29, a counter is set to a value representing the number of source coils ending with the immediately preceding source coil.

Specifically, a source coil meeting the condition set for step S27 is considered to lie inside a patient's body beyond the anus, while a source coil not meeting the condition is considered to lie outside the patient's body. For this reason, the counter is set to a value representing the number of source coils meeting the condition, ending with the immediately preceding source coil. The process then proceeds to step S30, whereupon the coordinates specifying the most proximal position of the inserted portion of the endoscope is added as the coordinates of the cut point.

The process then proceeds to step S31, wherein the length of the portion of the insertion unit 7 inserted into a patient's body is calculated by adding up the straightened distance between the coordinates of a point specifying the distal end of the endoscope and the cut point. It is judged at step S32 whether the calculated length information should be displayed. If it is judged that the information should be displayed, the process proceeds to step S33, whereupon the length of the inserted portion is displayed in the format, for example, Length: XXX mm. The process is then terminated. If it is judged at steps 32 that the length information should riot be displayed, the process is terminated.

In short, if it is designated that the length information should be displayed, the length of the portion of the insertion unit 7 inserted into a patient's body is displayed in the length-of-inserted portion indicator region 75 together with the shape of the endoscope as shown in FIG. 13A.

Figure 15:
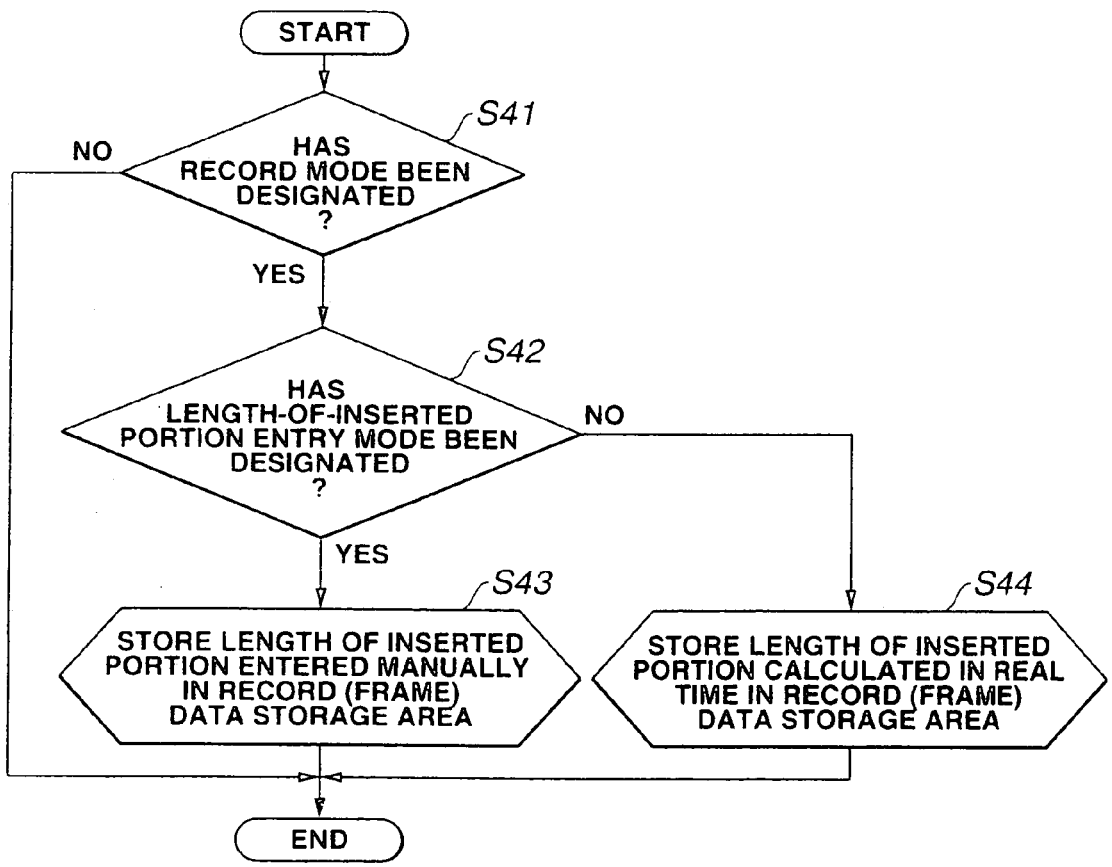

FIG. 15 describes the process to be performed for recording the length of the inserted portion.

When the shape-of-endoscope detecting apparatus 3 is activated, it is judged at step S41 whether a record mode has been designated. If the record mode has not been designated, the process is terminated. In contrast, if it is judged at step S41 that the record mode has been designated, the process proceeds to step S42. It is then judged whether a length-of-inserted portion entry mode has been designated.

If it is judged at step S42 that the length-of-inserted portion entry mode has been designated, the process proceeds to step S43. The length of an inserted portion entered manually is stored in a record (frame) data storage area, and recorded during recording. The process is then terminated. In contrast, if it is judged at step S42 that the length-of-inserted portion entry mode has not been designated, the process proceeds to step S44, whereupon the length of the inserted portion is calculated in real time and stored in a record (frame) data storage area, and recorded during recording. The process is then terminated.

When the length of the inserted portion is recorded, the length of the inserted portion can be referenced during the next examination. This is advantageous because reproducible data can be acquired during endoscopic examination.

According to the present embodiment, the length of the portion of the endoscope inserted into a body cavity can be displayed simultaneously with the shape of the endoscope, so that an operator of the endoscope will be informed of the length of the portion of the insertion unit 7, actually inserted into the body cavity. The operator's attention will therefore not be distracted from watching the monitor 24, on which the shape of the endoscope is indicated, or the monitor 11, on which the endoscopic image is displayed, to look at the insertion unit 7 of the endoscope so as to check the length of the inserted portion of the insertion unit. Such an arrangement results in an environment in which the insertion procedure can be readily performed with improved maneuverability or user-friendliness of the endoscope.

Moreover, since the apparatus includes the capability to record the length of the inserted portion, the recorded length can be utilized effectively for endoscopic examination.

Figure 13B:
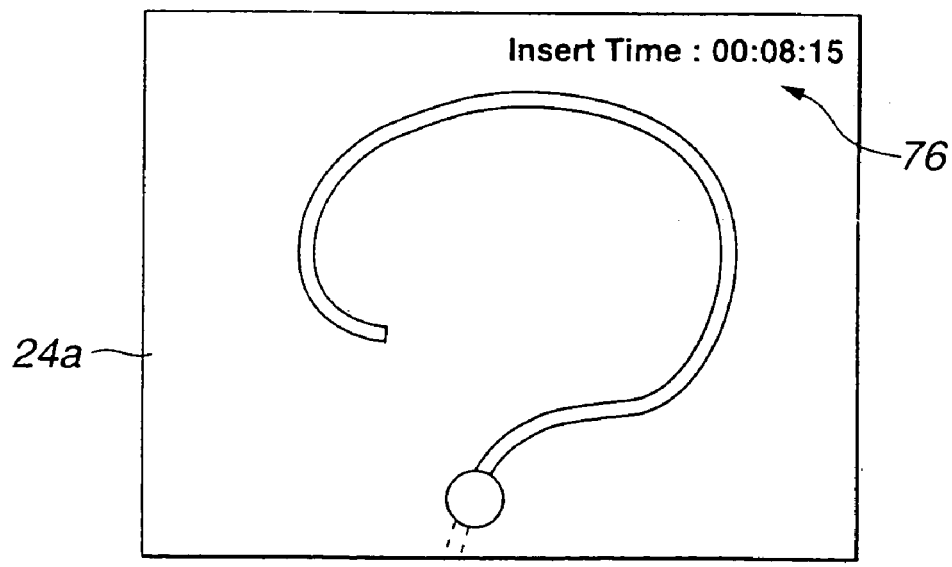
FIG. 13B shows an example in which the insertion time is displayed together with the shape of an endoscope.
Figure 16:
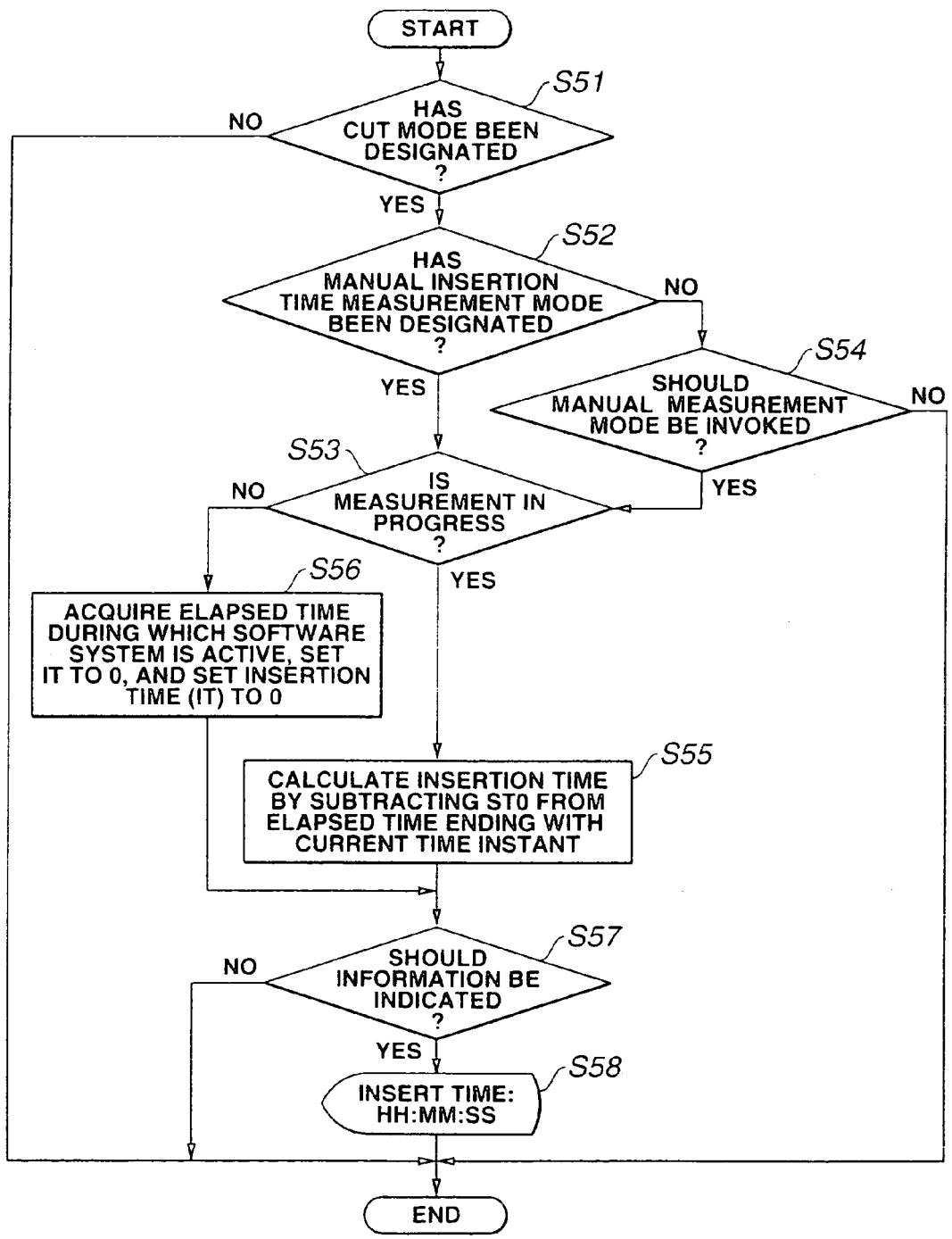

FIG. 13B shows a display mode in which an insertion time is displayed in an insertion time indicator region 76 together with the shape of the endoscope. FIG. 16 describes the process for attaining this display mode.

When the shape-of-endoscope detecting apparatus 3 is activated, it is judged at step S51 whether a cut mode in which the shape of only the portion of the endoscope inserted into a patient's body is graphically indicated has designated. If it is judged that the cut mode has not been designated, the process is terminated. If the cut mode has been designated, the process proceeds to step S52.

At step S52, it is judged whether an automatic insertion time measurement mode in which the insertion time is measured has been designated. If the automatic insertion time measurement mode has been designated, the process proceeds to step S53, wherein it is judged whether measurement is in progress. If it is judged at step S52 that the automatic insertion time measurement mode has not been designated, the process proceeds to step S54. It is then judged whether a manual measurement mode should be invoked. If it is judged that the manual measurement mode should be invoked, the process proceeds to step S53. If it is judged that the manual measurement mode should not be invoked, the process is terminated.

If it is judged at step S53 that measurement is not in progress, the process proceeds to step S56. An elapsed time during which a software system has been active is acquired. The elapsed time ST is set to 0. The host processor 27 saves the elapsed time in a register in the internal CPU 30. An insertion time IT is also set to 0. The process then proceeds to step S57 to judge whether the insertion time information should be displayed.

In contrast, if it is judged at step S53 that measurement is in progress, the process proceeds to step S55. The insertion time IT is calculated by subtracting the elapsed time STO, during which measurement is not in progress, from an elapsed time ending with the current time instant. The process then proceeds to step S57.

If it is judged at step S57 that the insertion time information should be displayed, the process proceeds to step S58, whereupon insertion time is then displayed as shown in FIG. 13B. The process is then terminated. In contrast, if it is judged at step S57 that the insertion time information should not be indicated, the insertion time is not displayed but the process is terminated.

As mentioned above, when the insertion time is displayed, an operator of the endoscope is apprised of an estimated time required for inserting the endoscope. An expert operator can complete the insertion work in a shorter period of time by referencing the displayed insertion time. When the endoscopic examination time is shortened, the pain the patient experiences during examination can be alleviated.

The sixth embodiment of the present invention will be described with reference to FIG. 17A through FIG. 18.

The present embodiment has, in addition to the same components as those of the first embodiment, for example, means for calculating an insertion ratio and displaying the information together with the shape of the endoscope. Herein, the insertion ratio is a ratio of the distance between the coordinates of a point specifying the distal position of the endoscope to the cut point to the length of the inserted portion of the endoscope.

When the insertion ratio, that is, the ratio of the distance between the coordinates of the point specifying the distal position of the endoscope and the cut point to the length of the inserted portion of the endoscope is displayed, it helps the operator of the endoscope to judge whether the insertion unit 7 inserted into a body cavity is looped or whether the insertion unit 7 is straightened.

Even when the endoscope is looped, the indicated shape of the endoscope may appear straight depending-on the direction of the indication. It maybe hard to judge upon viewing the indicated shape of the endoscope on the monitor whether the endoscope is actually looped or nearly straightened.

For example, a technique of looping the insertion unit 7, straightening it, and thus inserting it into a deep region may be employed in clinical practice. In this case, it must be determined whether the insertion unit is looped or straightened during the insertion process.

Figure 17A:
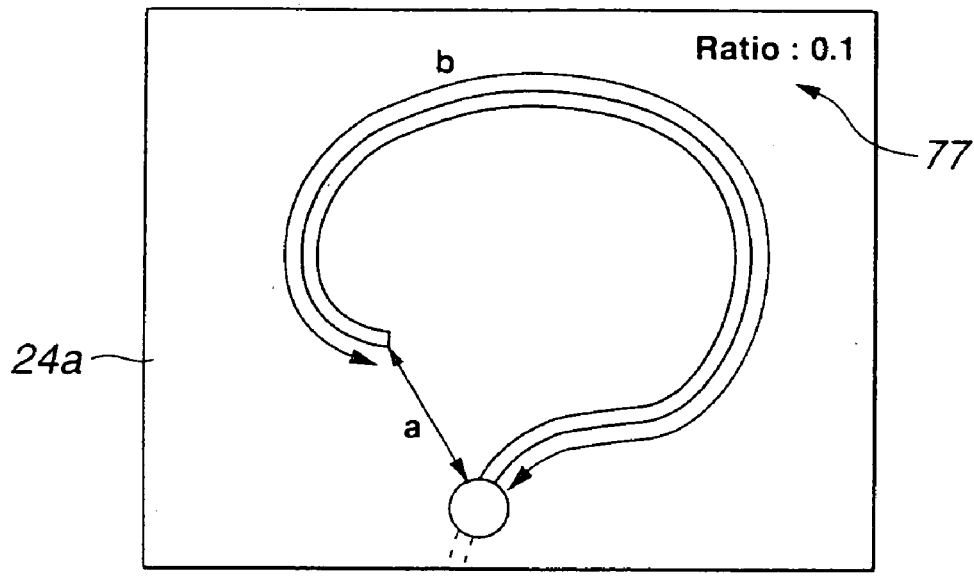
Figure 17B:
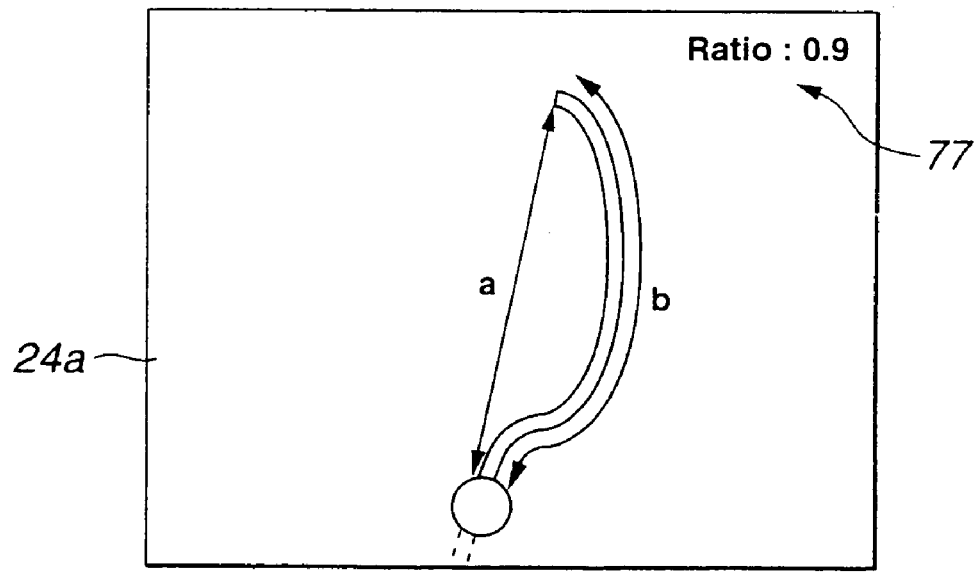
FIG. 17B shows another example in which the insertion ratio is displayed together with the shape of the endoscope, wherein the insertion ratio is high.

FIG. 17A and FIG. 17B show the indicated shape of the endoscope. Moreover, an insertion ratio, that is, a ratio of a straight distance between the coordinates of a point specifying the distal position of the endoscope and the cut point to the length of the inserted portion of the endoscope (a/b in FIGS. 17A and 17B) is displayed in an insertion ratio indication region 77. Based on the thus displayed insertion ratio, whether or not the endoscope is looped can be recognized without the necessity to change a direction of indication or a viewing direction in which the shape of the endoscope is graphically indicated.

In FIG. 17A, the insertion ratio displayed in the insertion ratio indication region 77 is low. This means that the endoscope is looped. In FIG. 17B, the indicated insertion ratio is high. This means that the endoscope is nearly straightened.

Figure 18:
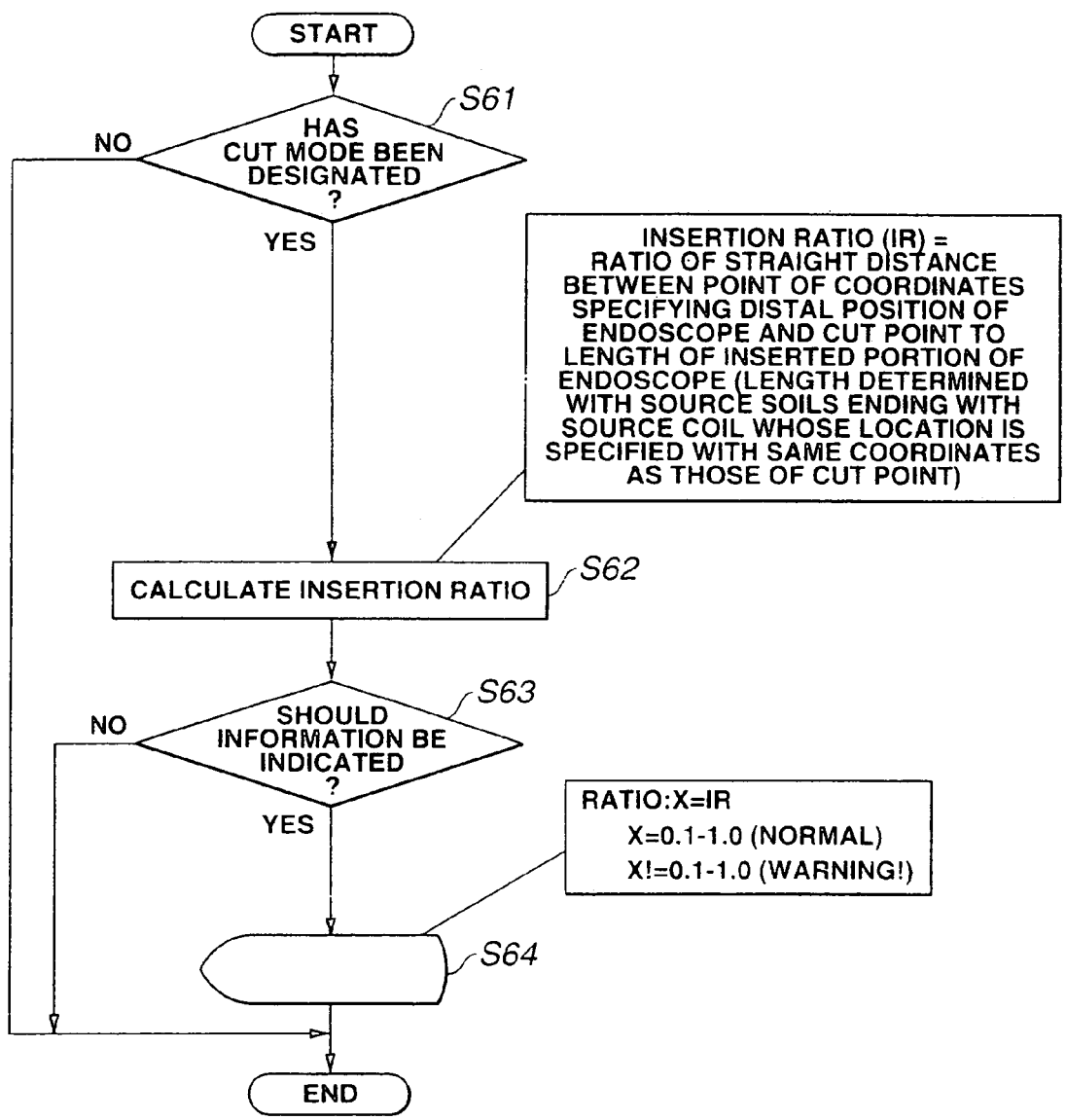

FIG. 18 describes the process performed for calculating and displaying the insertion ratio.

When the shape-of-endoscope detecting apparatus 3 is activated, it is judged at step S61 whether a cut mode in which the shape of only the portion of the endoscope inserted into a patient's body cavity is graphically indicated has been designated. If the cut mode has not been designated, the process is terminated. If the cut mode has been designated, the process proceeds to step S62, and the insertion ratio is calculated.

Specifically, the insertion ratio (IR), that is, a ratio of the distance between the coordinates of a point specifying the distal position of the endoscope and the cut point to the length of the inserted portion of the endoscope (the distance measured along the inserted portion from the coordinates of the point specifying the distal position to the cut point) is calculated. The process then proceeds to step S63.

If it is judged at step S63 that the inserted ratio information should be displayed, the process proceeds to step S64, whereupon the insertion ratio is displayed as shown in FIG. 17A or FIG. 17B. In contrast, if it is judged that the insertion ratio information need not be displayed, the insertion ratio is not displayed but the process is terminated.

If the insertion ratio is displayed at step S64, when the insertion ratio assumes a value ranging from 0.1 to 1.0, it is judged that the endoscope has been inserted normally. If the insertion ratio assumes any value smaller than 0.1 or larger than 1.0, it is judged that the endoscope has been inserted abnormally. An alarm is then given.

According to the present embodiment, whether the endoscope is looped or the endoscope is straightened can be judged from the insertion ratio without the necessity to change the direction of indication.

The seventh embodiment of the present invention will now be described with reference to FIG. 19A through FIG. 21.

The present embodiment is different from the first embodiment that the shape of the portion of the portion of the endoscope lying in a region of interest inside a patient's body can be graphically effectively indicated within a display area.

As the insertion unit 7 is inserted into a body cavity, the length of the portion of the insertion unit 7 inserted into the body cavity varies. When the shape of the endoscope is graphically indicated on the display screen, if the shape of the endoscope is indicated at a constant magnification, the ratio of the indicated shape to the dimensions of the display screen varies, as shown in FIG. 19B, proportionally to the length of the inserted portion. In the early stage of insertion, as seen from the left panel of FIG. 19B, only a small space in the display screen of the monitor is used to graphically indicate the shape.

According to the present embodiment, as shown in FIG. 19A, the magnification at which the shape of the endoscope is graphically indicated is varied with the change in the ratio of the length of the inserted portion of the endoscope to the overall length of the endoscope. Thus, the display space of the display screen 24a of the monitor is utilized effectively.

Figure 20A:
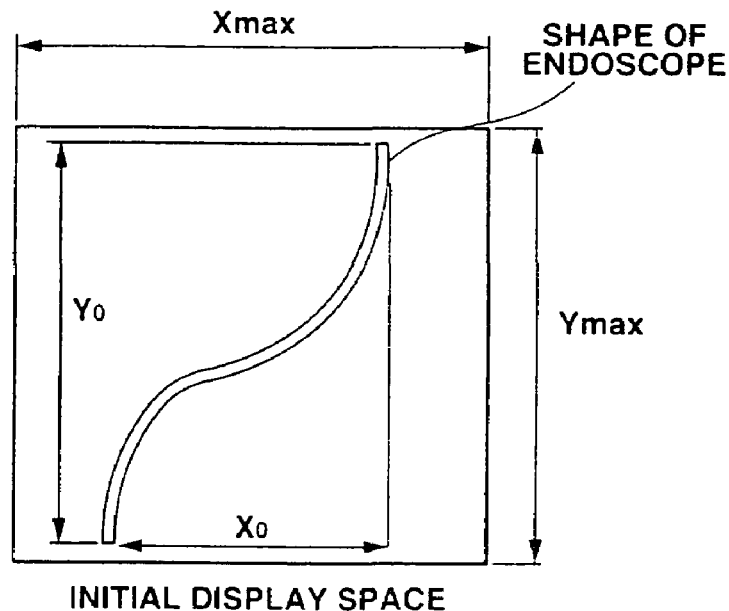
FIG. 20A shows a diagram for explaining the principles of the graphical indication mode in FIG. 19A, wherein the shape of an endoscope that is in an early stage of insertion is graphically indicated with a predetermined magnification Ao.
Figure 20B:
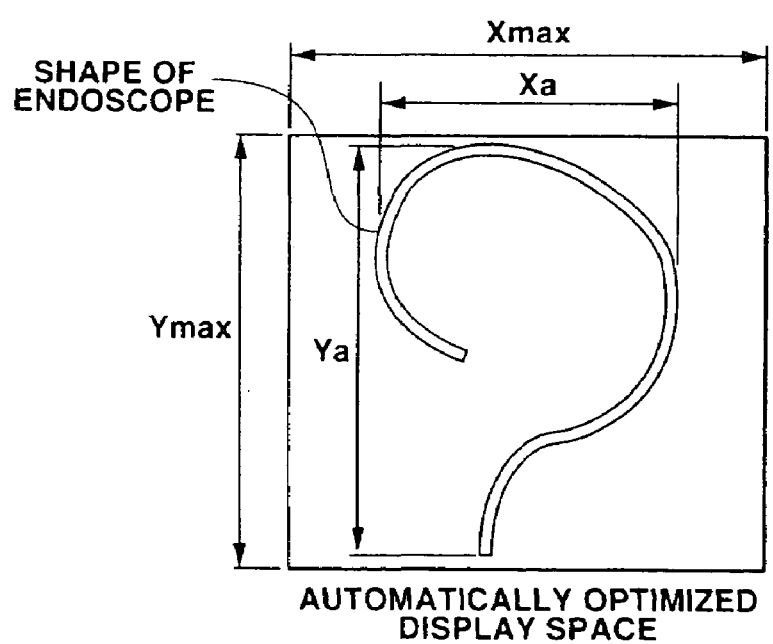
FIG. 20B shows a diagram for explaining the principles of the graphical indication mode shown in FIG. 19A, wherein the shape of an endoscope is graphically indicated at a magnification lower than the predetermined magnification Ao because a ratio of the length of the inserted portion of the endoscope to the overall length thereof has increased.

FIG. 20A and FIG. 20B are explanatory diagrams concerning the principles of graphically indicating the shape of the endoscope with a varying magnification depending on the shape.

FIG. 20A shows the shape of the endoscope, which is in an early stage of insertion, graphically indicated in the display space at a predetermined magnification Ao.

As illustrated, the shape of the endoscope is indicated within a space having a width Xo (=AoxXin) and a length Yo (=AoxYin). The magnification Ao is set to a value such that the size of the rectangular space (width Xo by length Yo) occupied by the indicated endoscope shape is only slightly smaller at least lengthwise or sideways than the size of the display space (width Xmax by length Ymax) on the screen 24a of the monitor. In FIG. 20A, the rectangular space is slightly smaller in the lengthwise direction.

Assume that the insertion unit 7 is further inserted and the width or length of the rectangular space in which the shape thereof is graphically indicated becomes a bit larger than Xo, or, Yo respectively. The apparatus detects that the rectangular space has become larger in size, and thus decreases the magnification incrementally so that the width and/or length of the rectangular space will be maintained to be slightly smaller than Xmax or Ymax.

The foregoing sequence is repeated so that the width or length of the rectangular space in which the shape of the endoscope is graphically indicated will approximate the width Xmax or length Ymax of the display space.

FIG. 20B shows the indicated shape of the endoscope having been inserted to a considerably deep region.

As illustrated, the rectangular space in which the shape of the endoscope is graphically indicated has a height Ya nearly the same as the height Ymax of the display space. In other words, the indicated shape of the endoscope is automatically optimized with respect to the display space. Incidentally, the width Xa of the rectangular space is considerably smaller than the width Xmax of the display space.

According to the present embodiment, the magnification at which the shape of the endoscope is graphically indicated is automatically varied so that at least one of the width and height of the rectangular space within which the shape is graphically indicated will approximate the width or height of the display space. Consequently, the shape of the endoscope can be graphically indicated with effective utilization of the display space.

Figure 21:
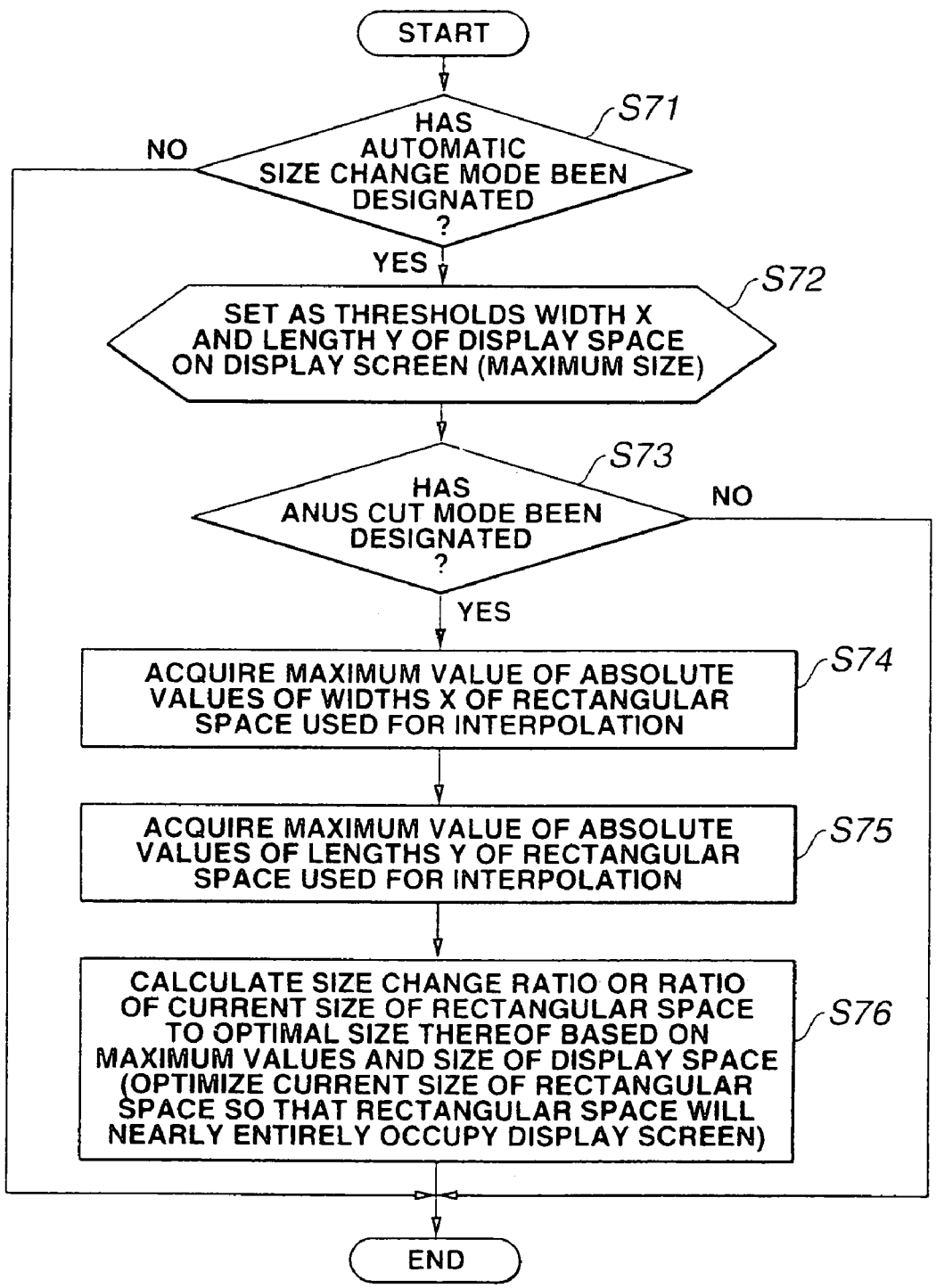

FIG. 21 describes the process for changing the magnification at which the shape of the endoscope is graphically indicated in proportion to the variation in the ratio of the length of the portion of the endoscope inserted into a patient's body cavity to the overall length of the endoscope, and for indicating the shape of the endoscope with effective utilization of the display space on the screen 24a of the monitor.

When the shape-of-endoscope detecting apparatus 3 is activated, it is judged at step S71 whether an automatic magnification change mode has been designated. If the automatic magnification change mode has not been designated, the process is terminated. If the automatic magnification change mode has been designated, the process proceeds to step S72.

At step S72, the width X and length Y (maximum width and maximum length) of the display space on the display screen are set as threshold values. The process then proceeds to step S73. As described above with reference to FIGS. 20A and 20B the threshold values may be set to values slightly smaller than the width and length of the display space respectively.

It is judged at step S73 whether an anus cut mode, in which the shape of the portion of the endoscope lying outside a patient's body beyond the anus is not graphically indicated, has been designated. Unless the cut mode has been designated, the process is terminated. If the cut mode has been designated, the process proceeds to step S74.

At step S74, the shape of the endoscope is estimated or a maximum value of (absolute values of) widths X of a rectangular space used for interpolation is acquired. At step S75, the shape of the endoscope is estimated or a maximum value of (absolute values of) heights Y of the rectangular space used for interpolation is acquired.

At step S76, a magnification change or a ratio of the current size of the rectangular space to an optimal size thereof is calculated based on the maximum values and the size of the display space. In other words, the current size of the rectangular space is adjusted so that the whole of the shape of the inserted portion of the endoscope will be graphically indicated over the whole of the display space on the screen.

Thus, the display space can be utilized effectively.

According to the present embodiment, a user need not set the magnification so that the shape of the endoscope will be graphically indicated using the whole display space. The user can observe the shape of the endoscope graphically indicated at a proper magnification using nearly the whole display space.

In the embodiments described above, a driving signal is applied to the source coils 13$i$ incorporated in the endoscope or the marker coils 18$j$ placed at predetermined positions. Magnetic fields are thus induced around the coils, and magnetically detected by the sensor coils 21$k$ located at known positions. The coils inducing magnetic fields may be replaced with the coils detecting the magnetic fields.

To be more specific, source coils may be incorporated in the coil unit, 20, and sensor coils may be incorporated in the endoscope in order to detect the magnetic field signals. The locations of the sensor coils may be calculated based on the detected signals relative to the source coils located at known positions.

Likewise, the marker coils may be realized with sensor coils, and the locations of the marker coils may be calculated based on signals detected by the marker coils.

Further embodiments constructed by combining features of the embodiments described above are also within the scope of the present invention. For example, when the shape of the endoscope is graphically indicated with the size thereof changed, an absolute scale may be displayed in accordance with the magnification at which the shape of the endoscope is graphically indicated.

The eighth embodiment of the present invention will now be described with reference to FIG. 22 through FIG. 42.

Figure 22:
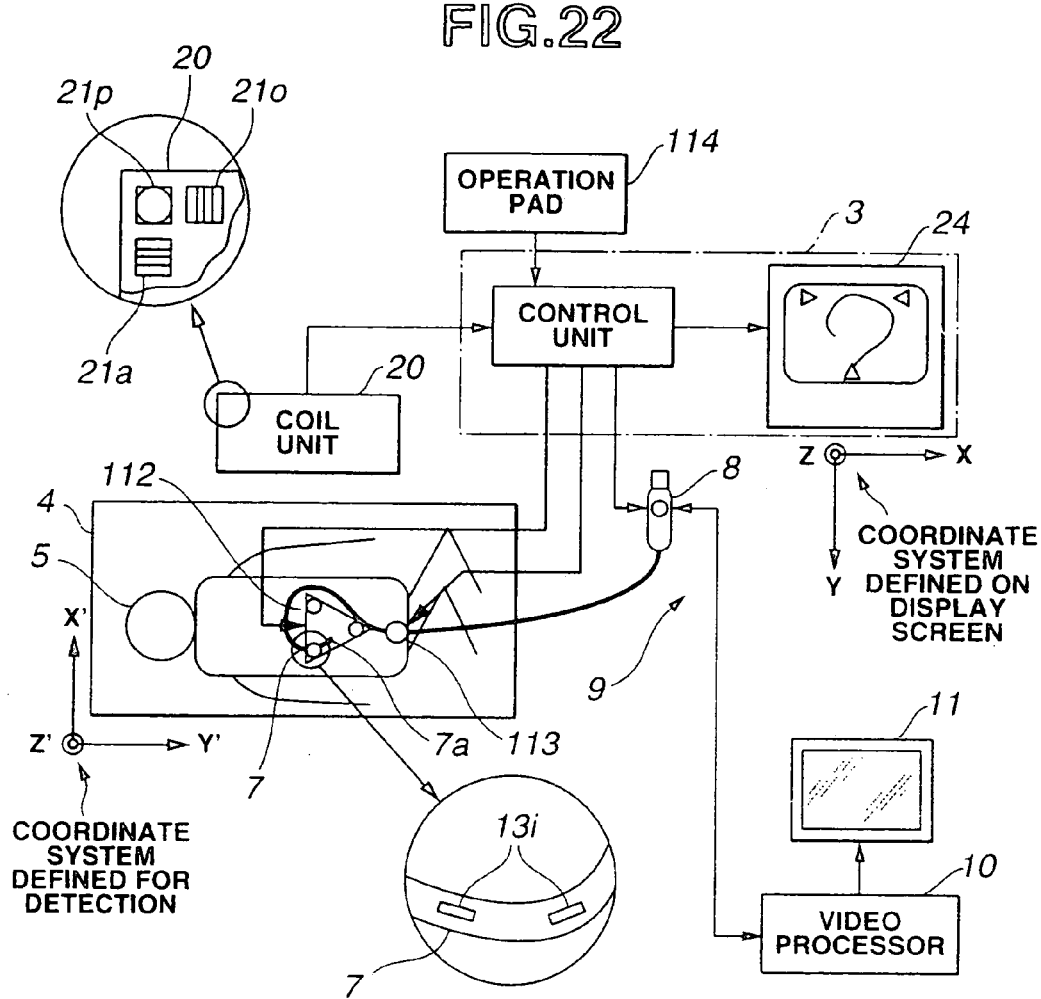

According to the first embodiment, three markers of the first through third markers 17$a$, 17$b$, and 17$c$ are placed on the skin surface of the patient 5 near the anus and on the left and right sides of the patient's torso. According to the present embodiment, as shown in FIG. 22, the endoscope system 1 includes a marker plate 112 shaped substantially like an isosceles triangle and an extracorporeal coil 113. Three coils for use in detecting a position near the anus of the patient 5 lying down on the examination table 4, a position on the left side of the patient's torso, and a position on the right side of the patient's torso are incorporated, as will be described later, in the marker plate 112. The extracorporeal coil 113 is used to sense a desired position on the patient 5 and is manipulated by an operator of the endoscope system.

Figure 23:
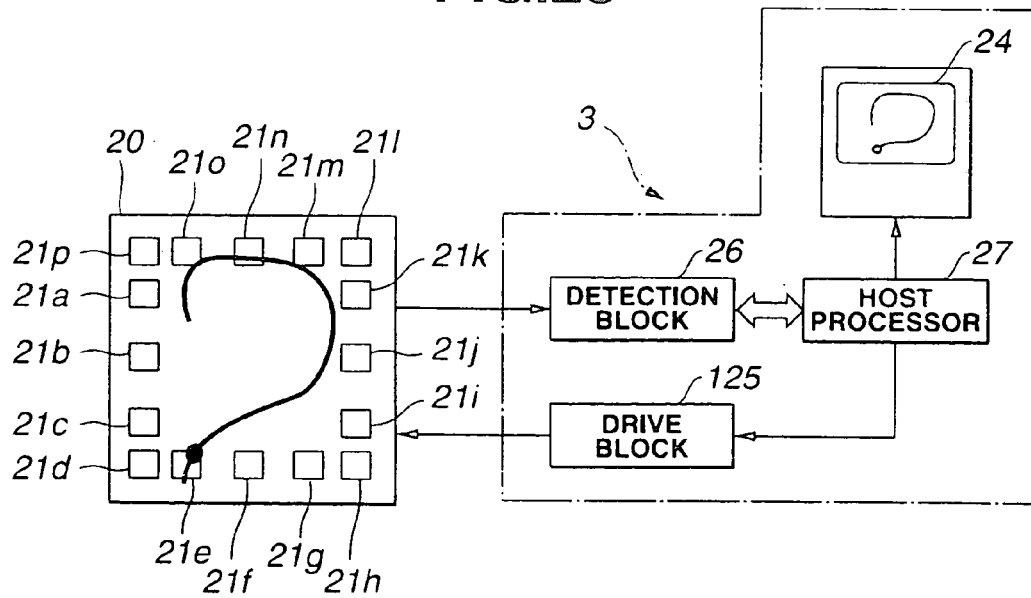

The shape-of-endoscope detecting apparatus 3 in accordance with the present embodiment and as shown in FIG. 23 consists generally of a drive block 125, the detection block 26, and the host processor 27. The drive block 125 drives the source coils 13$i$, the three coils incorporated in the marker plate 112, and the extracorporeal coil 113. The detection block 26 detects signals received by the sensor coils 21$k$. The host processor 27 processes the signals detected by the detection block 26. An operator pad 114 is used to operate the apparatus.

Figure 24A:
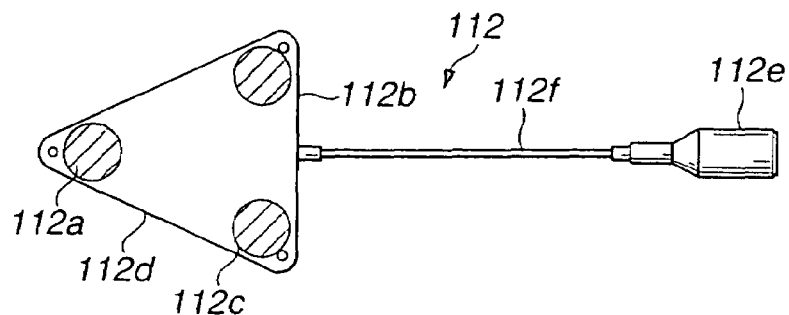
FIG. 24A is a plan view for explaining the structure of a marker plate.
Figure 24B:
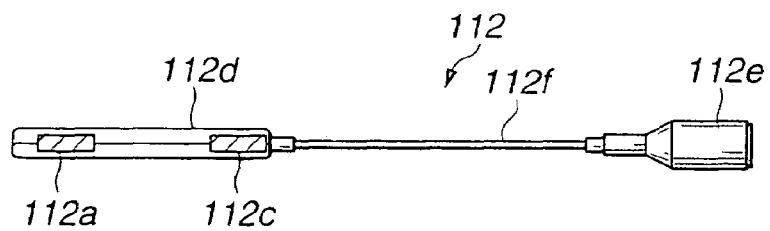
FIG. 24B is a side view for explaining the structure of the marker plate of FIG. 24A.

As shown in FIG. 24A and FIG. 24B, the marker plate 112 consists of a plate body 112$d$ and a cable 112$f$. A lower coil 112$a$ used to detect a position near a patient's anus, a right coil 112$b$ used to detect a position on the right side of the patient's torso, and a left coil 112$c$ used to detect a position on the left side of the patient's torso are incorporated on the same plane in the plate body 112$d$. A joint connector 112$e$ to be plugged into a control unit included in the shape-of-endoscope detecting apparatus so that it can be unplugged freely is attached to the cable 112$f$ extending from the plate body 112$d$.

When the joint connector 112$e$ is plugged into the control unit, the control unit applies a high-frequency signal, which serves as a driving signal, to the lower coil 112$a$, right coil 112$b$, and left coil 112$c$ in the marker plate 112, which thereby serves as a magnetic field generator. Similarly to the source coils 13$i$, the lower coil 112$a$, right coil 112$b$, and left coil 112$c$ radiate electromagnetic waves including magnetic fields. Incidentally, when a high-frequency signal serving as a driving signal is applied from the control unit to the extracorporeal coil 113, the extracorporeal coil 113 also radiates an electromagnetic wave including a magnetic field.

Figure 25:
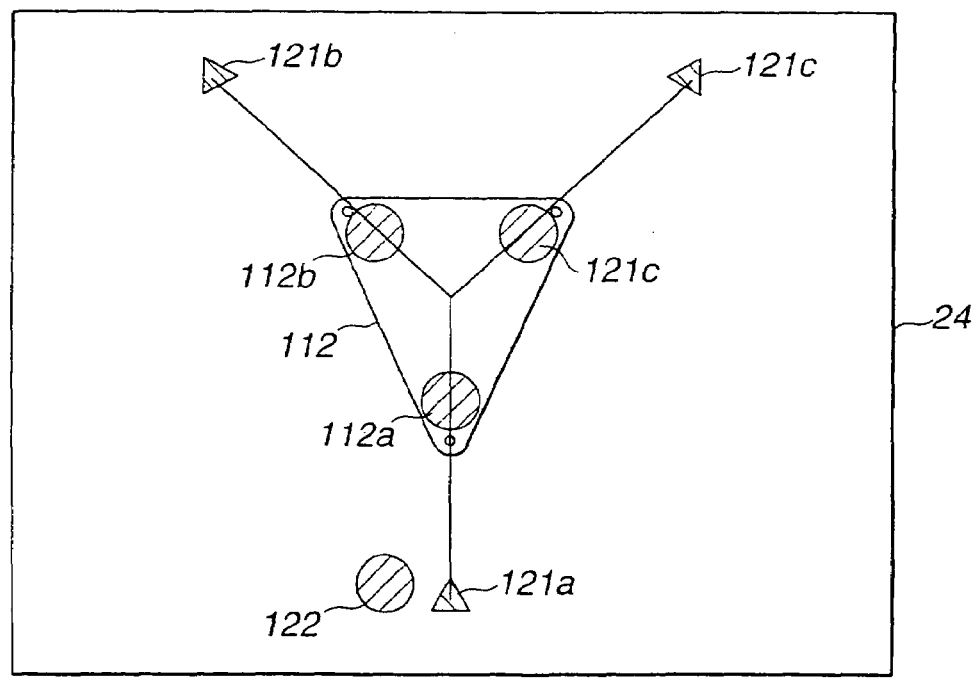

The electromagnetic waves including magnetic fields being radiated from the lower coil 112$a$, right coil 112$b$, left coil 112$c$, and extracorporeal coil 113 are detected by the sensor coils 21$k$ incorporated in the coil unit 20. Based on the electromagnetic waves detected by the sensor coils 21$k$, the control unit depicts, as shown in FIG. 25, on a monitor 24 a lower mark 121$a$, a right mark 121$b$, and a left mark 121$c$ representing the lower coil 112$a$, right coil 112$b$, and left coil 112$c$, respectively, and an extracorporeal mark 122 representing the extracorporeal coil 113.

The marker plate 112 is designed compactly so that it can be easily placed on the patient 5 as shown in FIG. 22. For this reason, the detected locations of the lower coil 112$a$, right coil 112$b$, and left coil 112$c$ are different from the positions near the anus of the patient 5, the right side of the patient's torso, and the left side thereof.

Based on the detected locations of the lower coil 112$a$, right coil 112$b$, and left coil 112$c$, the lower mark 121$a$, right mark 121$b$, and left mark 121$c$ are produced to indicate the positions near the anus, the right side of the patient's torso, and the left side thereof, respectively.

Alternatively, the lower coil 112$a$, right coil 112$b$, and left coil 112$c$ may be not incorporated in a plate body 112$d$, but may be each provided separately like the extracorporeal coil 113. However, when the lower coil 112$a$, right coil 112$b$, and left coil 112c are incorporated in the plate body 112d, the coils can be connected to the control unit via the single cable 112f, which simplifies the wiring arrangement.

A process for producing the marks displayed on a monitor and representative, the lower left and right coils will be described below.

Figure 26:
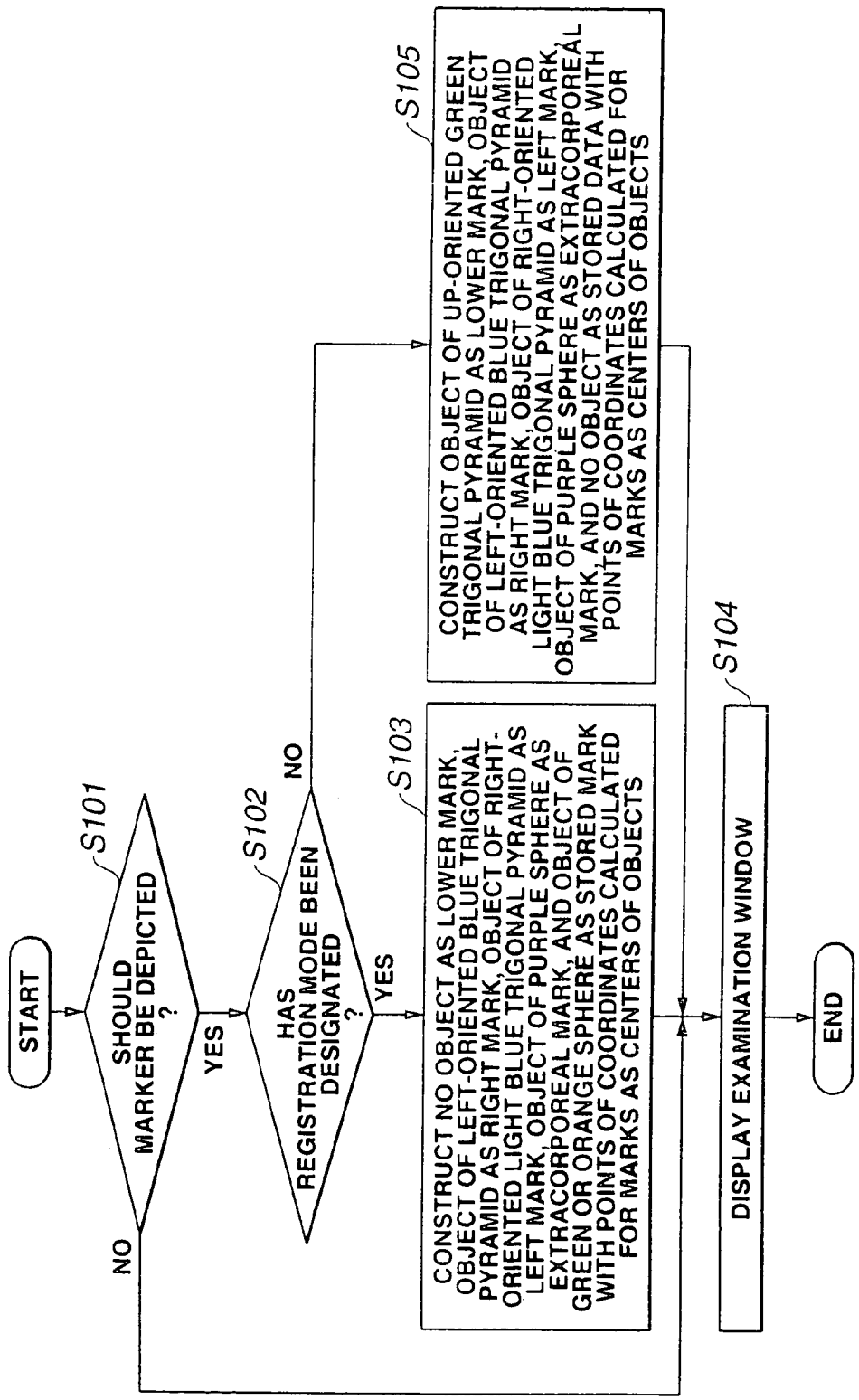

As described in FIG. 26, in the shape-of-endoscope detecting apparatus 3, it is judged at step S101 whether a marker depiction instruction has been received. Such instruction may be designated using, for example, the operator pad 114 shown in FIG. 22 if it is judged that the marker need not be depicted, the process is terminated. If an instruction has been received that the marker should be depicted, the process proceeds to step S102.

At step S102, it is judged from an entry made at the operator pad 114 whether a registration mode in which the detected locations of the lower coil 112a, right coil 112b, left coil 112c, and extracorporeal coil 113 are stored has been designated.

If the registration mode has been designated, the process proceeds to step S103 wherein various objects are created as the marks to be displayed to represent the coil positions. The coordinates of predetermined points are calculated as the centers of the marks. Specifically, a leftwardly pointing blue triangular pyramid is created as the right mark 121; a rightwardly pointing light blue triangular pyramid is created as the right mark 121c; a purple sphere is created as the extracorporeal mark 122; and a green or orange sphere is created as a mark to be stored. However, no object is created as a mark 121a to represent the lower coil 112a.

Figure 27:
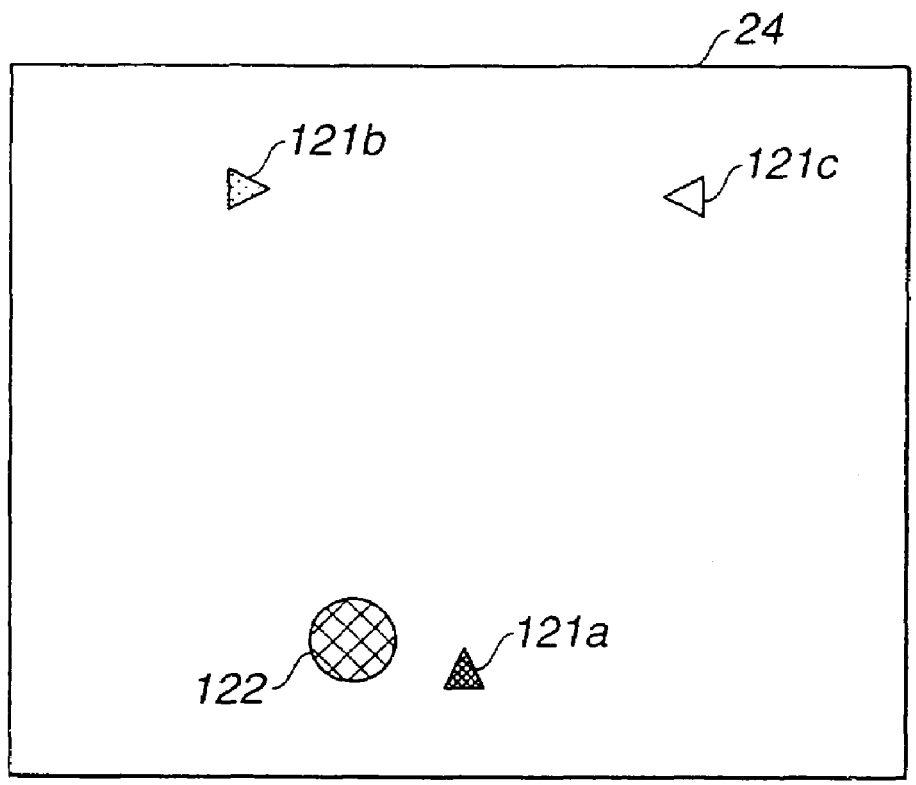

If the registration mode has not been designated, the process proceeds to step S105, wherein various objects are created as the marks to be displayed to represent the coil positions. The coordinates of predetermined points are calculated as the centers of the marks. Specifically, an upright green triangular pyramid is created as the lower mark 121a; a leftwardly pointing blue triangular pyramid is created as the right mark 121b; a rightwardly pointing light blue triangular pyramid is created as the 15, left mark 121c; and a purple sphere is created as the extracorporeal marker 122. No object is created as a mark to be stored. FIG. 27 shows an example in which the produced marks are displayed on the monitor 24.

An operation executed by the present embodiment will now be described below.

Figure 28A:
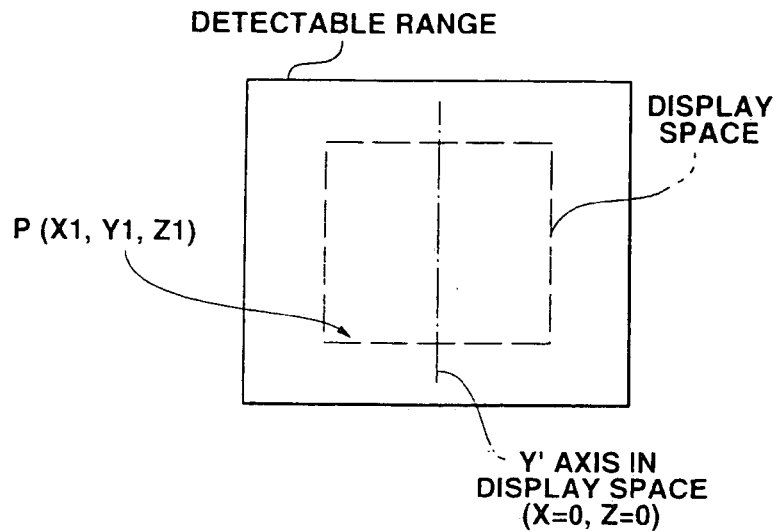
FIG. 28A to FIG. 28C are explanatory diagrams representing the shape of an endoscope graphically indicated by a conventional shape-of-endoscope detecting apparatus.
Figure 28B:
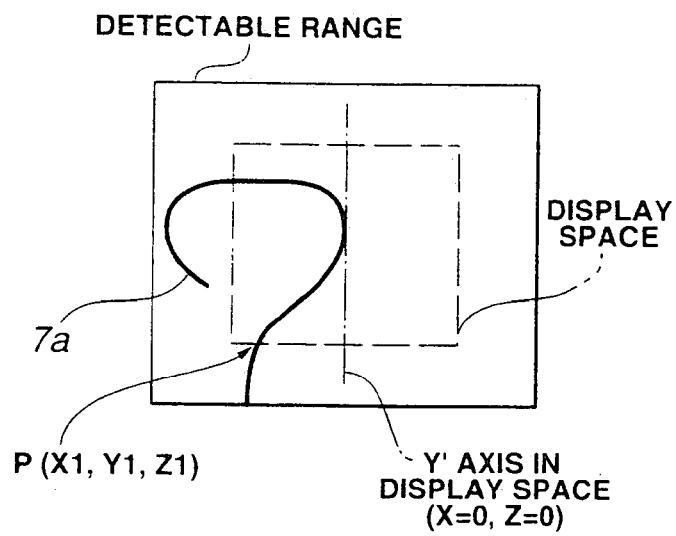
Figure 28C:
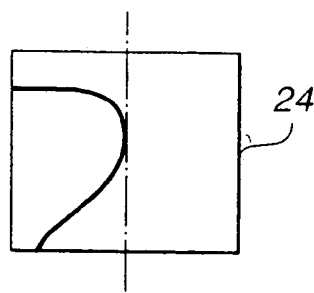

In a conventional shape-of-endoscope detecting apparatus, the detectable range or the range detectable by the sensor coils is inconsistent with the display space on a monitor, as shown in FIG. 28A. Assume that the patient 5 changes his/her posture, and that the intracorporeal position of the distal part 7a of the insertion unit 7 falls outside a range consistent with the display space, as shown in FIG. 28B. In this case, although the shape of the inserted portion of the insertion unit 7 can be detected, when the shape is graphically indicated on the monitor 24, part of the shape is missing, as shown in FIG. 28C.

For preventing this situation, in the present embodiment, a process is performed as described below.

First, a process performed when neither the marker plate 112 nor the external coil 113 is employed will be described below.

Figure 29:
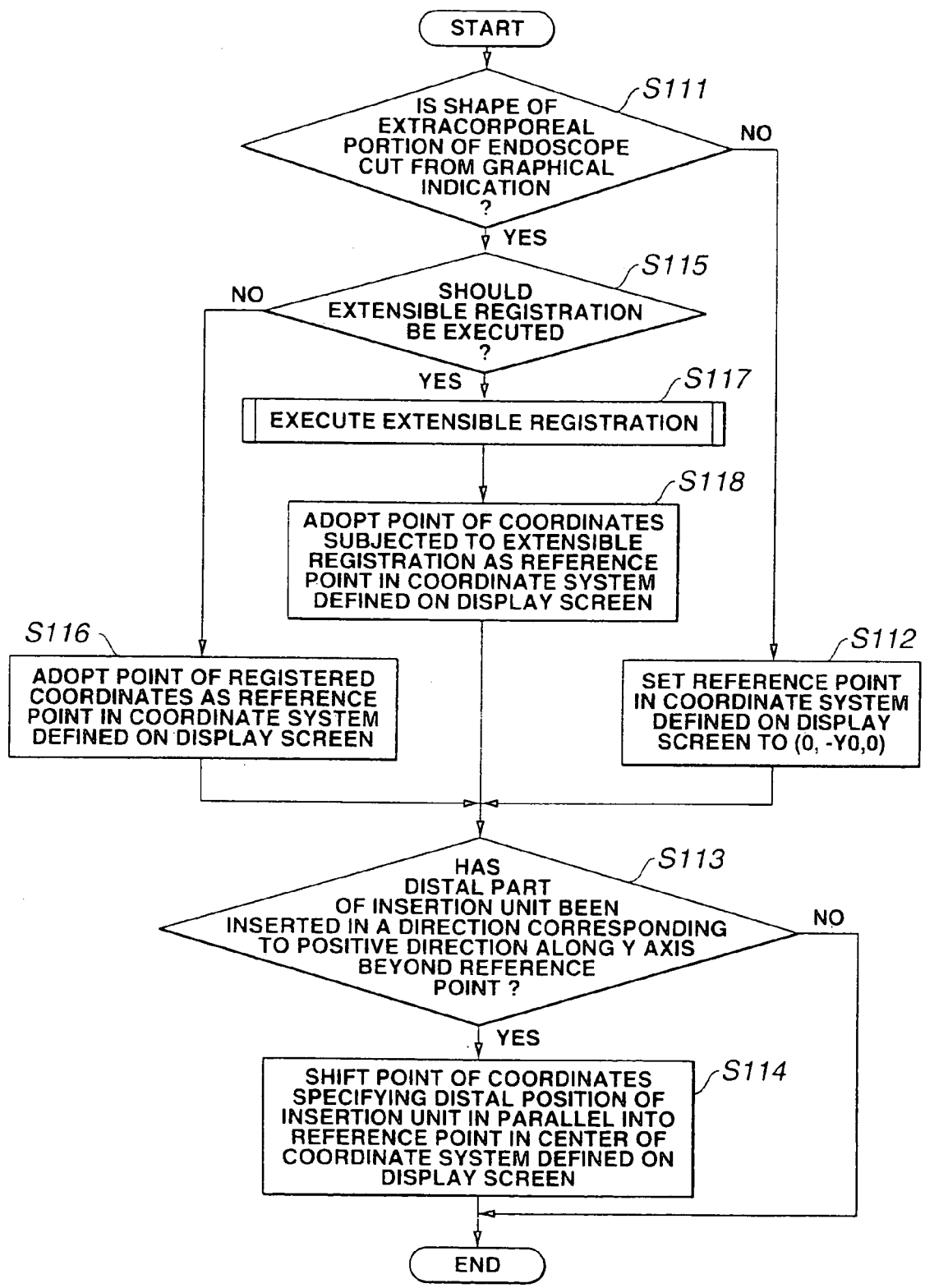

As described in FIG. 29, it is judged at step S111 whether the shape of an extracorporeal portion of the insertion unit 7 will be cut from graphical indication. If it has been designated using, for example, the operator pad 114 that the shape of the extracorporeal portion will not be cut from graphical indication, the process proceeds to step S112, in which reference point in a coordinate system defined on the display screen (X, Y, Z) (see FIG. 22) is set to a point (0, Y0, 0). The process then proceeds to step S113.

At step S113, it is detected using the sensor coils 21k whether the distal part of the insertion unit 7 has been inserted in a direction corresponding to the positive direction along the Y axis beyond the reference point. If it is detected that the distal part has been inserted in the positive Y axis direction, the process proceeds to step S114, wherein the coordinates of a point specifying the distal position of the insertion unit 7 that has just been inserted is shifted in parallel to the reference point. The process is then terminated.

Figure 30A:
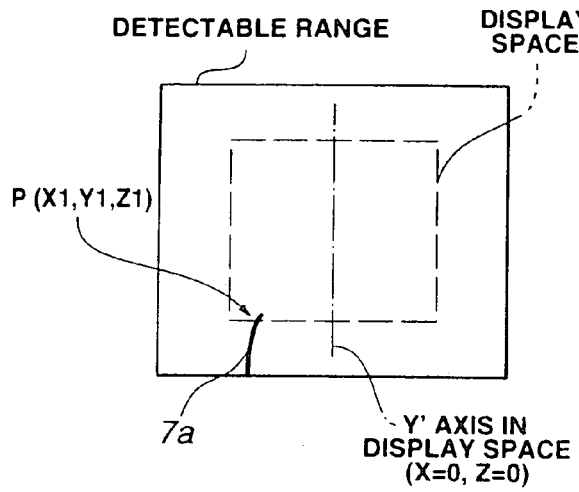
FIG. 30A to FIG. 30D show examples of graphical indication that vary with the progress of the process performed in the shape-of-endoscope detecting apparatus of the present invention.
Figure 30B:
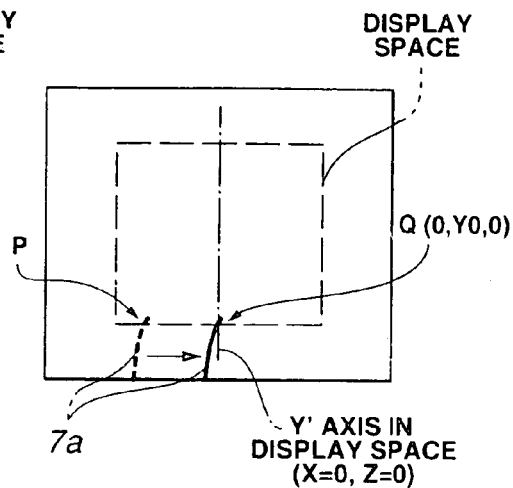
Figure 30C:
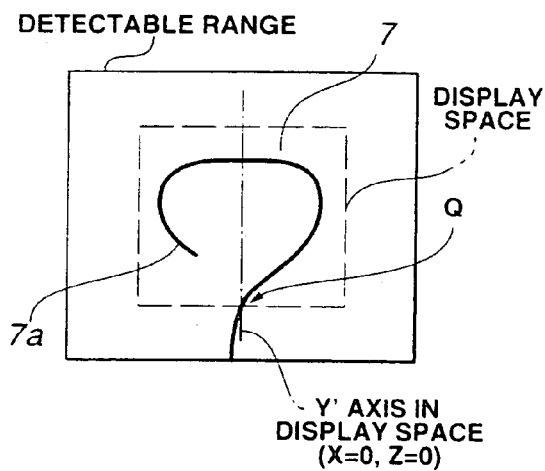
Figure 30D:
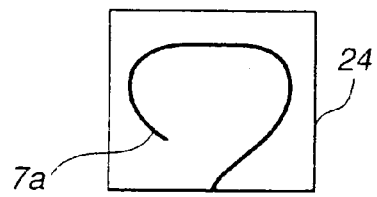

Specifically, the portion of the detectable range coincident with the display area shifts due to a change in the posture of the patient 5. For example, when the intracorporeal position of the distal part of the insertion unit 7 enters the display area slightly, as shown in FIG. 30A, the coordinates of the point specifying the distal position of the insertion unit 7 that has just been inserted is, as shown in FIG. 30B, are shifted to the reference point (0, Y0, 0) in the center of the coordinate system defined on the display screen. Consequently, the shape of the whole inserted portion of the insertion unit 7 is, as shown in FIG. 30C, detected in the range consistent with the display space. The shape of the whole inserted portion of the insertion unit 7 is therefore, as shown in FIG. 30D, graphically indicated on the monitor 24.

Next, a process performed when only the marker plate 112 alone is used will be described below.

As shown in FIG. 29, it is judged at step S111 whether an extracorporeal portion of the insertion unit 7 is to be cut from graphical indication. If the extracorporeal portion is to be cut from graphical indication, the detected locations of the lower coil 112a, right coil 112b, and left coil 112c of the marker plate 112 are stored (registered). The process then proceeds to step S115.

It is then judged at step S115 whether extensible registration (to be described later) should be executed. If extensible registration need not be executed, the process proceeds to step S116. The coordinates of a point specifying the detected and stored location of the lower coil 112a is adopted as the reference point. The above-described steps S113 and S114 are then carried out.

Figure 31A:
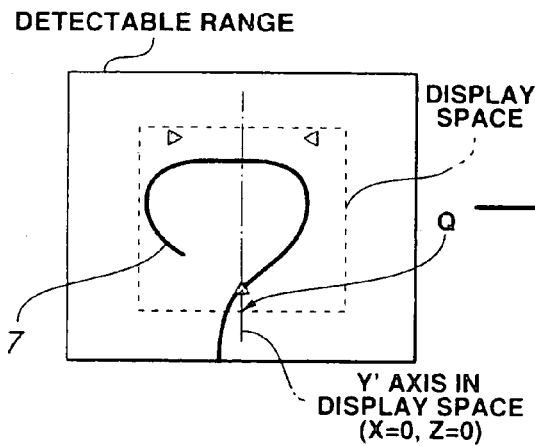
FIG. 31A and FIG. 31B are explanatory diagrams directed to another operation executed by the shape-of-endoscope detecting apparatus of the present invention.
Figure 31B:
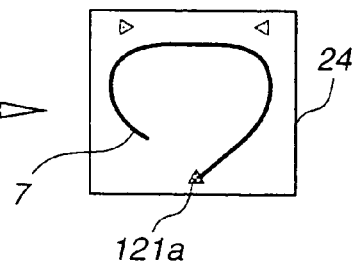

Since the reference point is set to the coordinates of a point specifying the detected location at step S116, the shape of the insertion unit 7 is, as shown in FIG. 31A detected within the range consistent with the display space. At the same time, the locations of the lower coil 112a, right coil 112b, and left coil 112c incorporated in the marker plate 112 are detected. Consequently, as shown in FIG. 31B, the shape of the insertion unit 7 is graphically indicated on the monitor 24 with the marks representing the coils displayed thereon.

The lower mark 121a representing the lower coil 112a indicates the location of the anus through which the insertion unit 7 has been inserted into a patient's body. If it is determined at step S111 that an extracorporeal portion of the insertion unit 7 is to be cut from graphical indication, the extracorporeal portion of the insertion unit 7 is cut from the graphical indication of the shape of the endoscope.

Next, a process performed when the marker plate 112 and extracorporeal coil 113 are both used will be described below.

As shown in FIG. 29, first, it is judged at step S111 whether the extracorporeal portion of the insertion unit 7 is to be cut from graphical indication. If it is determined that the extracorporeal portion is to be cut from graphical indication, the detected locations of the lower coil 112a, right coil 112*b*, and left coil 112*c* incorporated in the marker plate 112 are stored (registered). Thereafter, the process proceeds to step S115.

It is judged at step S115 whether extensible registration (to be described later) should be executed. If extensible registration will be executed, the process proceeds to step S117. Extensible registration is then executed. At step S118, the coordinates of a point subjected to extensible registration is adopted as the reference point. The process then proceeds to step S113 and step S114.

Figure 32:
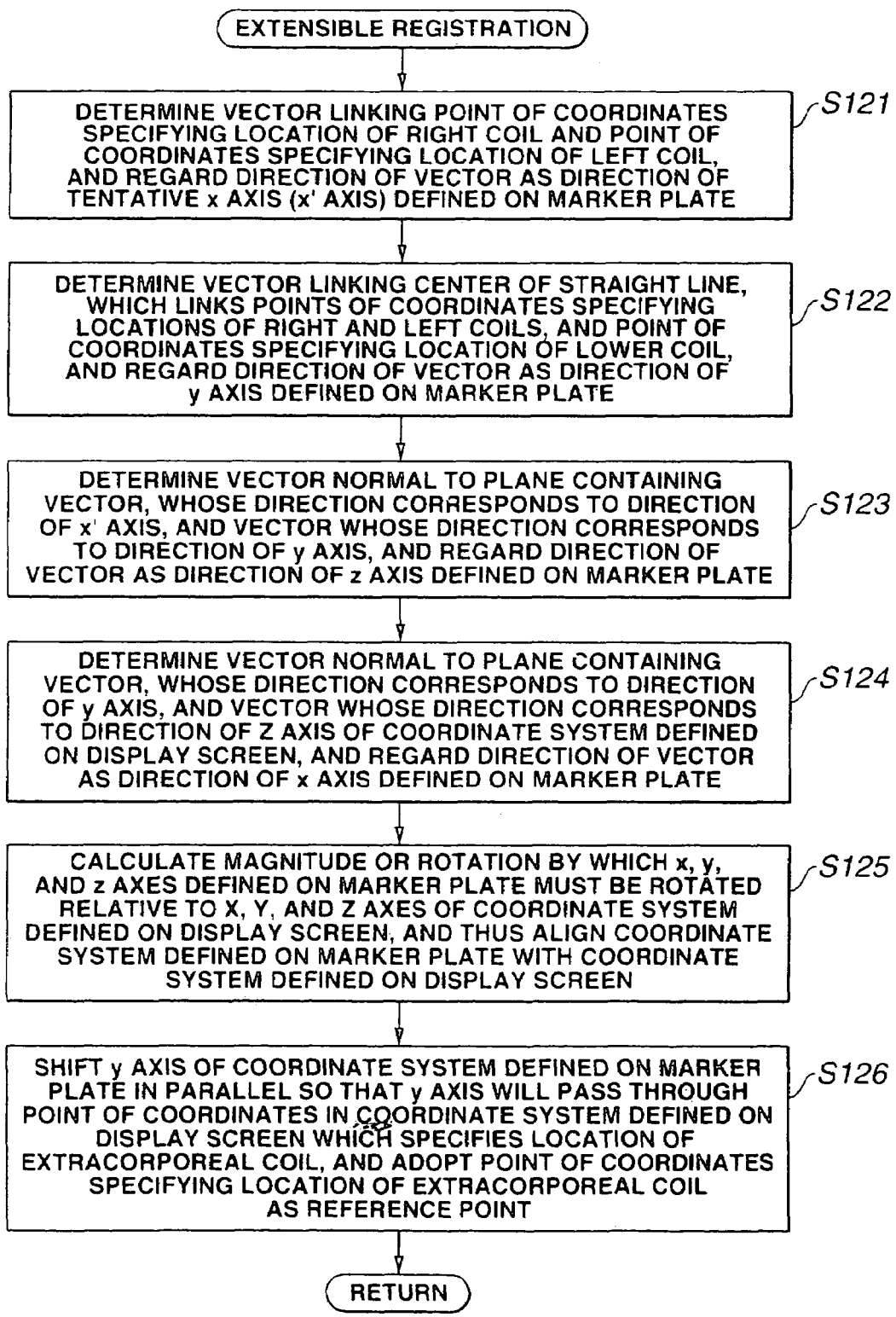
Figure 33:
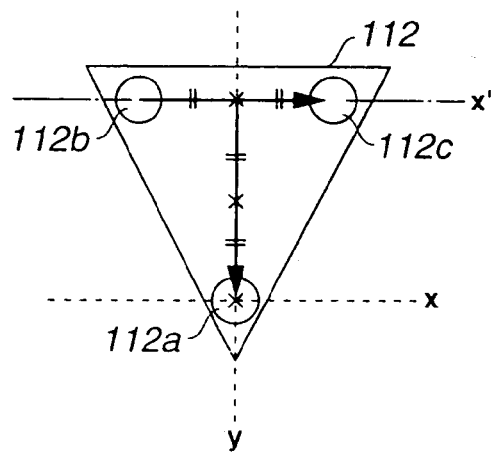
Figure 34:
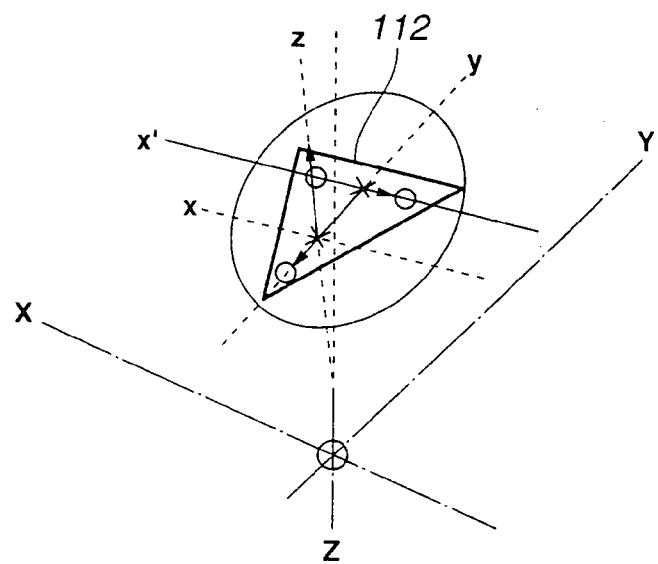

The extensible registration procedure of step S117 is described in FIG. 32. Specifically, a vector linking, as shown in FIG. 33, the coordinates of a point specifying the location of the right coil 112*b* and the coordinates of a point specifying the location of the left coil 112*c* is calculated at step S121. The direction exhibited by the vector is regarded as the direction of a tentative x axis (x' axis) defined on the marker plate 112.

The axis extending in the direction of the vector linking the coordinates of the points specifying the locations of the right coil 112*b* and left coil 112*c* is regarded as the tentative x axis. This is because if the x axis linking the coordinates of the points specifying the locations of the right coil 112*b* and left coil 112*c* is extended to the margins of the detectable range for the sensor coils 21*k*, the detection results may be distorted.

Thereafter, at step S122, a vector linking, as shown in FIG. 33, the center point on the straight line linking the coordinates of the points specifying the locations of the right coil 112*b* and left coil 12*c* and the coordinates of a point specifying the location of the lower coil 112*a* is calculated. The direction exhibited by the vector is regarded as the direction of the y axis defined on the marker plate 112.

At step S123, a vector normal to the plane containing the vector whose direction corresponds to the direction of the x axis and the vector whose direction corresponds to the direction of the y axis is calculated. The direction exhibited by the normal vector is regarded as the direction of the z axis defined on the marker plate 112.

At step S124, a vector normal to the plane containing the vector whose direction corresponds to the direction of the y axis and the vector whose direction corresponds to the direction of the z axis is calculated. The direction exhibited by the normal vector is regarded as the direction of the x axis defined on the marker plate 112.

A coordinate system (x, y, z) defined on the marker plate 112 is thus determined by the steps S121 through S124.

Figure 35:
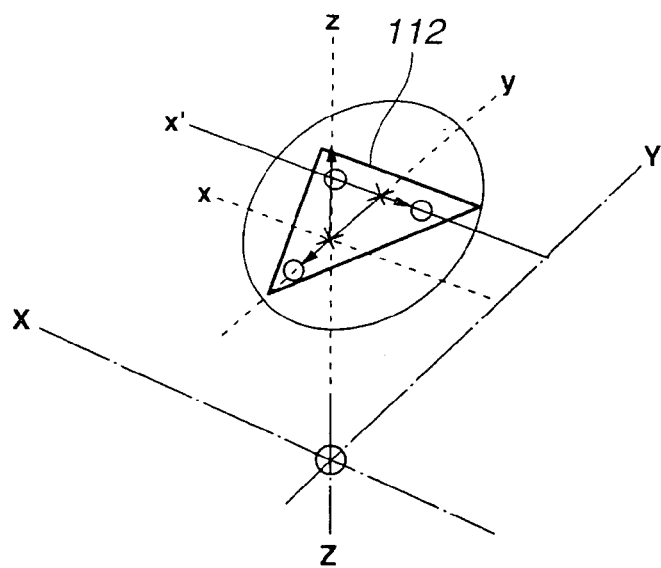

A magnitude of rotation by which the coordinate system (x, y, z) defined on the marker plate 112 and determined at step S125 is rotated relative to the coordinate system (X, Y, Z) defined on the display screen is calculated. The coordinate system (x, y, z) defined on the marker plate 112 is thus, as shown in FIG. 35, aligned with the coordinate system (X, Y, Z) defined on the display screen.

Figure 36:
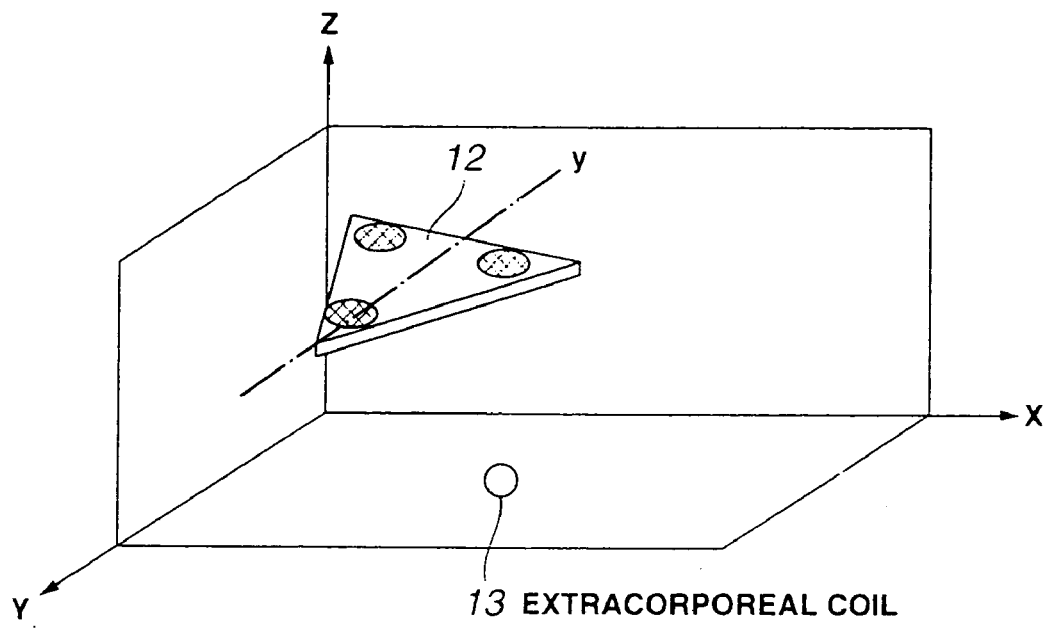
Figure 37:
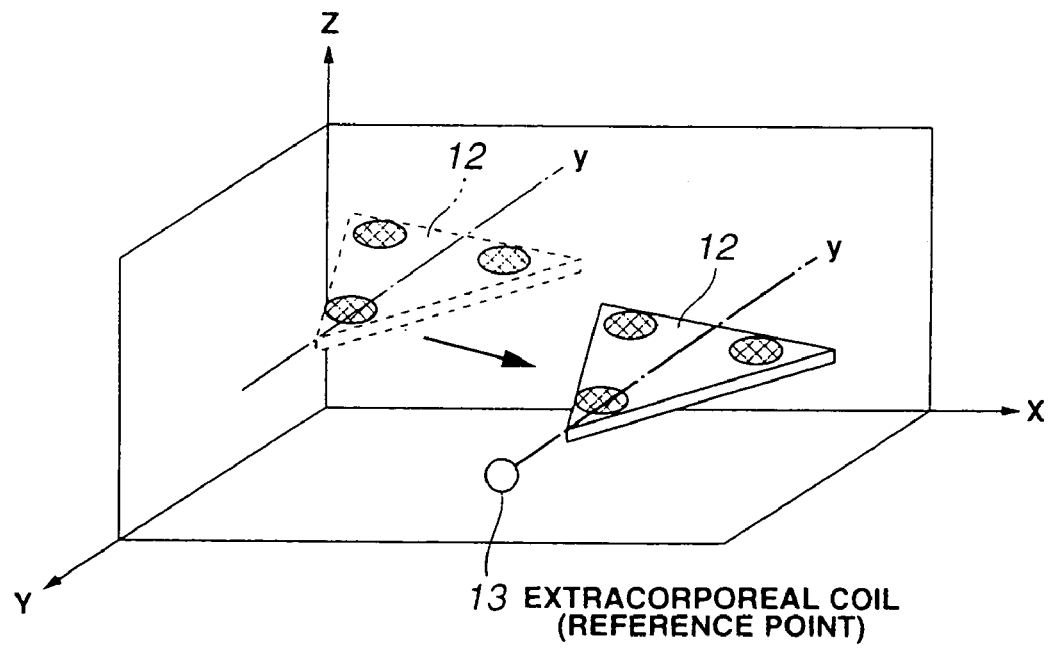

The coordinate system (x, y, z) defined on the marker plate 112 have the same directions as the coordinate system X, Y, Z) defined on the display screen. Since the location of the patient's anus is registered as the position through which the insertion unit is inserted, the y axis on the marker plate 112 does not, as shown in FIG. 36, pass through the coordinates of a point specifying the location of the extracorporeal coil 113. Therefore, the y axis on the marker plate 112 is, as shown in FIG. 37, shifted in parallel so that the y axis will pass through coordinates of the point specifying the location of the extracorporeal coil 113. The coordinates of the point specifying the location of the extracorporeal coil 113 is regarded as the coordinates of a point subjected to extensible registration, whereupon the process then returns to step S118 in FIG. 29.

The coordinates of the point subjected to extensible registration is adopted as the reference point at step S118. The process then returns to step S113 and step S114. Even if the posture of the patient 5 changes during the endoscopic examination, the shape of the endoscope can be observed in the same manner as the shape of the endoscope inserted into the body of a patient assuming an ideal posture. Also, insertion of the endoscope can be achieved with simple manipulations.

Figure 38:
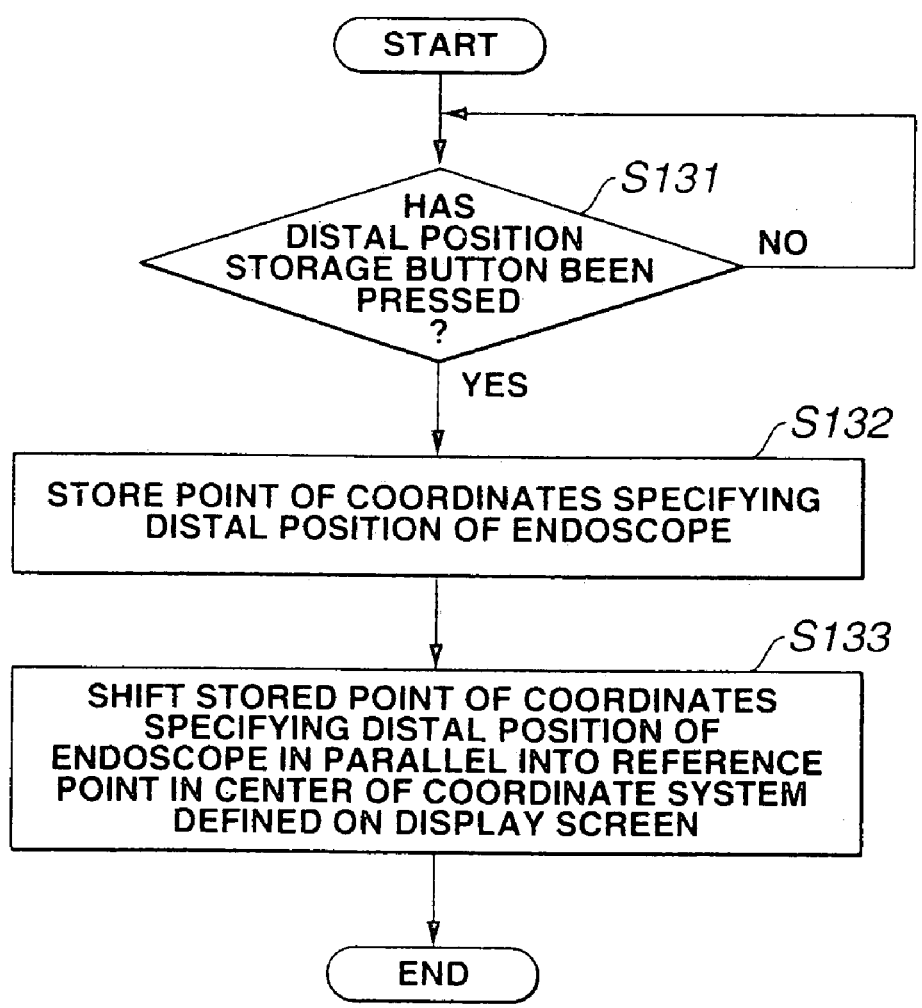

According to the present embodiment, as described in FIG. 38, when the insertion unit 7 is inserted into a patient's body, it is checked at step S131 if a distal position storage button has been pressed using the operator pad 114. If the distal position memory button has been pressed, the process proceeds to step S132.

At step S132, the coordinates of a point specifying the distal position of the insertion unit that has just been inserted is stored. The process then proceeds to step S133. The stored coordinates of the point specifying the distal position of the insertion unit is substituted for the coordinates of the point specifying the location of the extracorporeal coil 113 and being subjected to extensible registration. The y axis defined on the marker plate 112 is shifted so that it will pass through the coordinates of the point specifying the distal position of the insertion unit 7 that has just been inserted. Alternatively, the coordinates of the point specifying the distal position of the insertion unit 7 that has just been inserted may be shifted to the coordinates of the point subjected to extensible registration. The process may then be returned to step S118 in FIG. 29.

Figure 39:
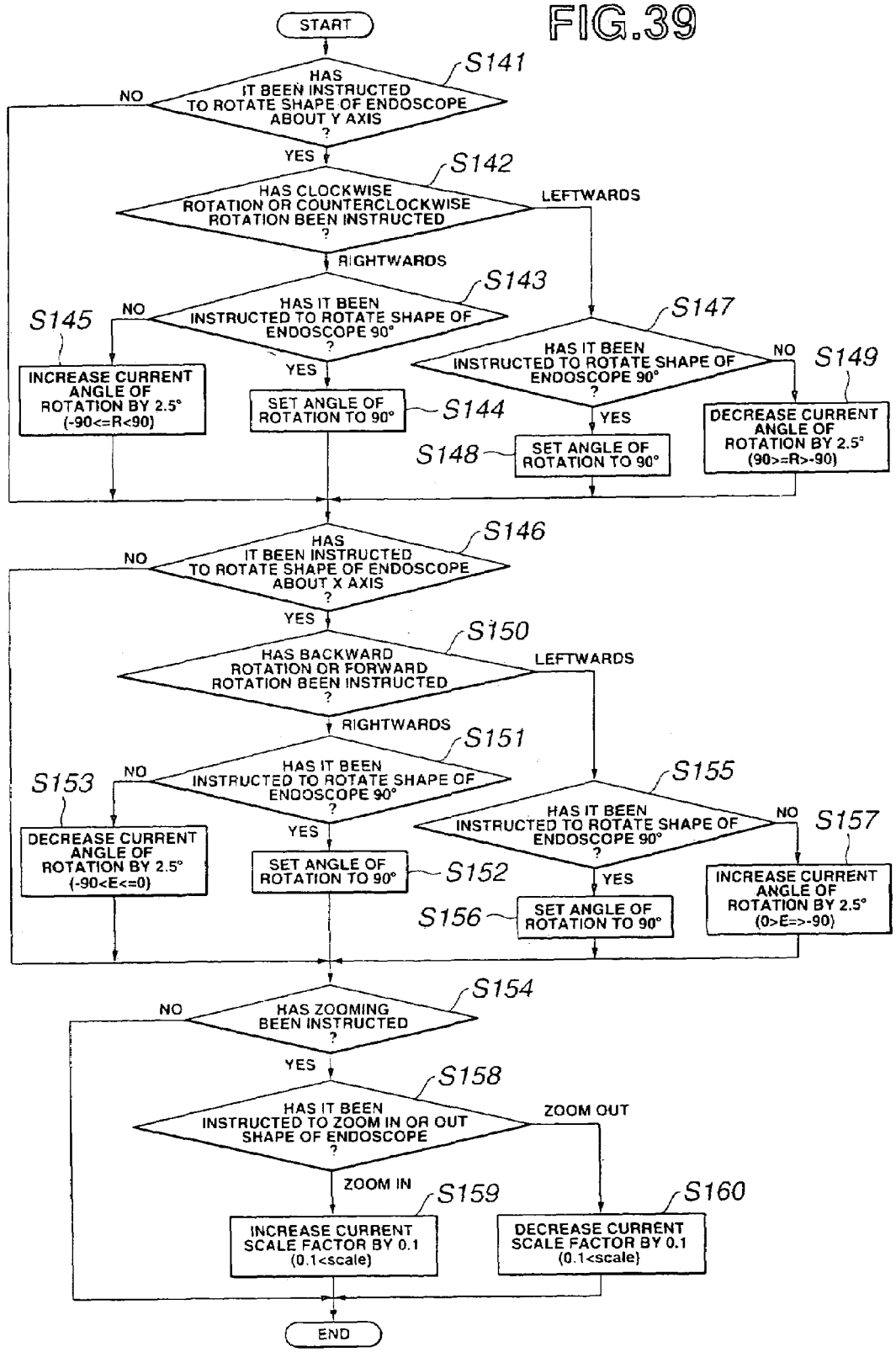

Furthermore, according to the present embodiment, it is judged at step S141 in FIG. 39 whether an instruction has been received to rotate the shape of the endoscope about the Y axis of the coordinate system defined on the display screen.

If an instruction to rotate the shape of the endoscope about the Y axis has been received, the process proceeds to step S142. It is then judged whether clockwise or counterclockwise rotation has been instructed. If no instruction to rotate the shape of the endoscope about the Y axis has been received, the process proceeds to step S146.

If it is judged at step S142 that clockwise rotation has been instructed, the process proceeds to step S143, whereupon it is judged whether an instruction to rotate the shape of the endoscope 90° has been received. If an instruction to rotate the shape of the endoscope 90° has been received, the process proceeds to step S144, whereupon the angle of rotation is set to 90', and the process then proceeds to step S146. If it is judged at step S143 that no instruction to rotate the shape of the endoscope 90° has been received, the process proceeds to step S145, whereupon the angle of rotation is increased by +2.5°, and the process then proceeds to step S146.

If it is judged at step S142 that counterclockwise rotation has been instructed, the process proceeds to step S147, whereupon it is judged whether an instruction to rotate the shape of the endoscope 90° has been received. If an instruction to rotate the shape of the endoscope 90° has been received, the process proceeds to step S148, whereupon the angle of rotation is set to 90°, and the process then proceeds to step S146. If it is judged at step S147 that no instruction to rotate the shape of the endoscope 90° has been received, the process proceeds to step S149. The angle of rotation is then decreased by 2.5°, and the process proceeds to step S146.

At step S146, it is judged whether an instruction has been given using the operator pad 114 to rotate the shape of the endoscope about the X axis of the coordinate system defined on the display screen. If an instruction to rotate the shape of the endoscope about the X axis has been given, the process proceeds to step S150, where it is then judged whether backward rotation or forward rotation has been instructed. If no instruction to rotate the shape of the endoscope about the X axis has been given, the process proceeds to step S154.

If it is judged at step S150 that backward rotation has been instructed, the process proceeds to step S151. It is judged whether an instruction has been given to rotate the shape of the endoscope 90°. If an instruction to rotate the shape of the endoscope 90° has been given, the process proceeds, to step S152, whereupon the angle of rotation is then set to 90°. If it is judged at step S151 that no instruction to rotate the shape of the endoscope 90° has been given, the process proceeds to step S153, whereupon the angle of rotation is decreased by 2.5°, and the process then proceeds to step S154.

If it is judged at step S150 that forward rotation has been instructed, the process proceeds to step S155. It is judged whether an instruction has been given to rotate the shape of the endoscope 90°. If an instruction to rotate the shape of the endoscope 90° has been given, the process proceeds to step S156, whereupon the angle of rotation is set to 90°. If it is judged at step S155 that no instruction has been given to rotate the shape of the endoscope a 90°, the process proceeds to step S157, whereupon the angle of rotation is increased by 2.5°, and the process proceeds to step S154.

At step S154, it is judged whether selection of a zoom function has been instructed using the operator pad 114. If selection of a zoom function has not been instructed, the process is terminated. If an instruction for a zoom function has been given, the process proceeds to step S158, whereupon it is judged whether it has been instructed to zoom in or out on the shape of the endoscope. If it is determined that instructions to zoom in on the shape of the endoscope have been given, the process proceeds to step S159, wherein a scale factor is increased by 0.1, and the process is then terminated. If it is judged at step S158 that instructions to zoom out on the shape of the endoscope have been given, the scale factor is decreased by 0.1 at step S1160. The process is then terminated.

The process of rotation described with reference to FIG. 39 makes it possible to turn a viewing direction, in small angle increments of rotation (2.5°) to account for every change in a patient's posture during the insertion examination procedure. Here, the shape of the endoscope is graphically indicated as if the endoscope were viewed from the viewing direction. Thus, the viewing direction can also be rotated horizontally or vertically by a large angle of rotation (90°), whereby the viewing direction can be changed readily.

Moreover, the viewing direction may is not limited to being rotated horizontally or vertically by the large angle increments of rotation (90°). If desired, the viewing direction may be rotated in increments of 45° or 30°. For example, assuming that the viewing direction is to be rotated 50°, the viewing direction is first rotated 45° and then rotated 2.5° twice. Thus, three manipulations are performed in order to rotate the viewing direction 50°. In comparison, when the viewing direction is rotated 50° in increments of 2.5°, twenty manipulations must be performed.

Figure 40:
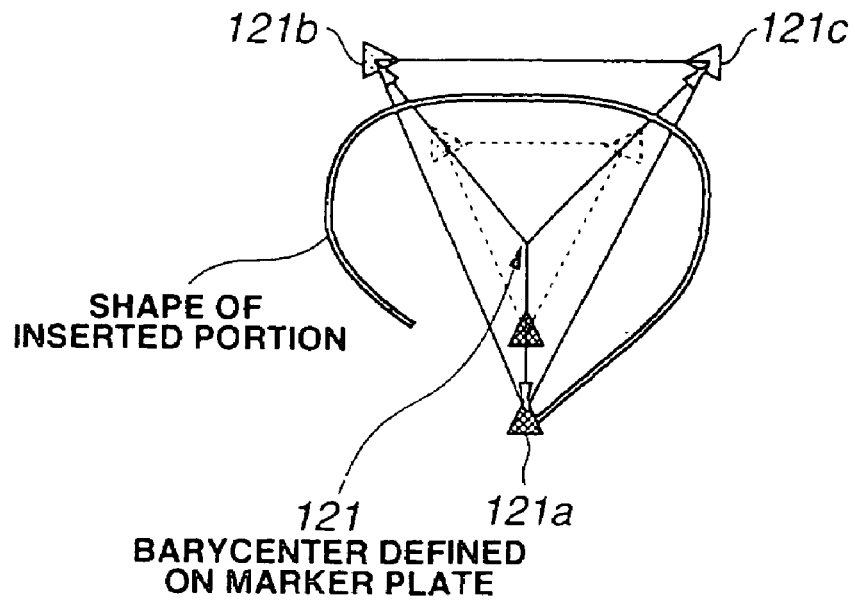

Moreover, according to the present embodiment, as shown in FIG. 40, the marks 121a, 121b and 121c on the display representing the marker coil locations can be zoomed in or out with the barycenter of the coordinate system defined on the marker plate 112 as a center. Depending on whether the patient is an adult or a child (having a smaller build than an adult), the marks 121a, 121b and 121c can be displayed differently using the same marker plate 112.

Figure 41:
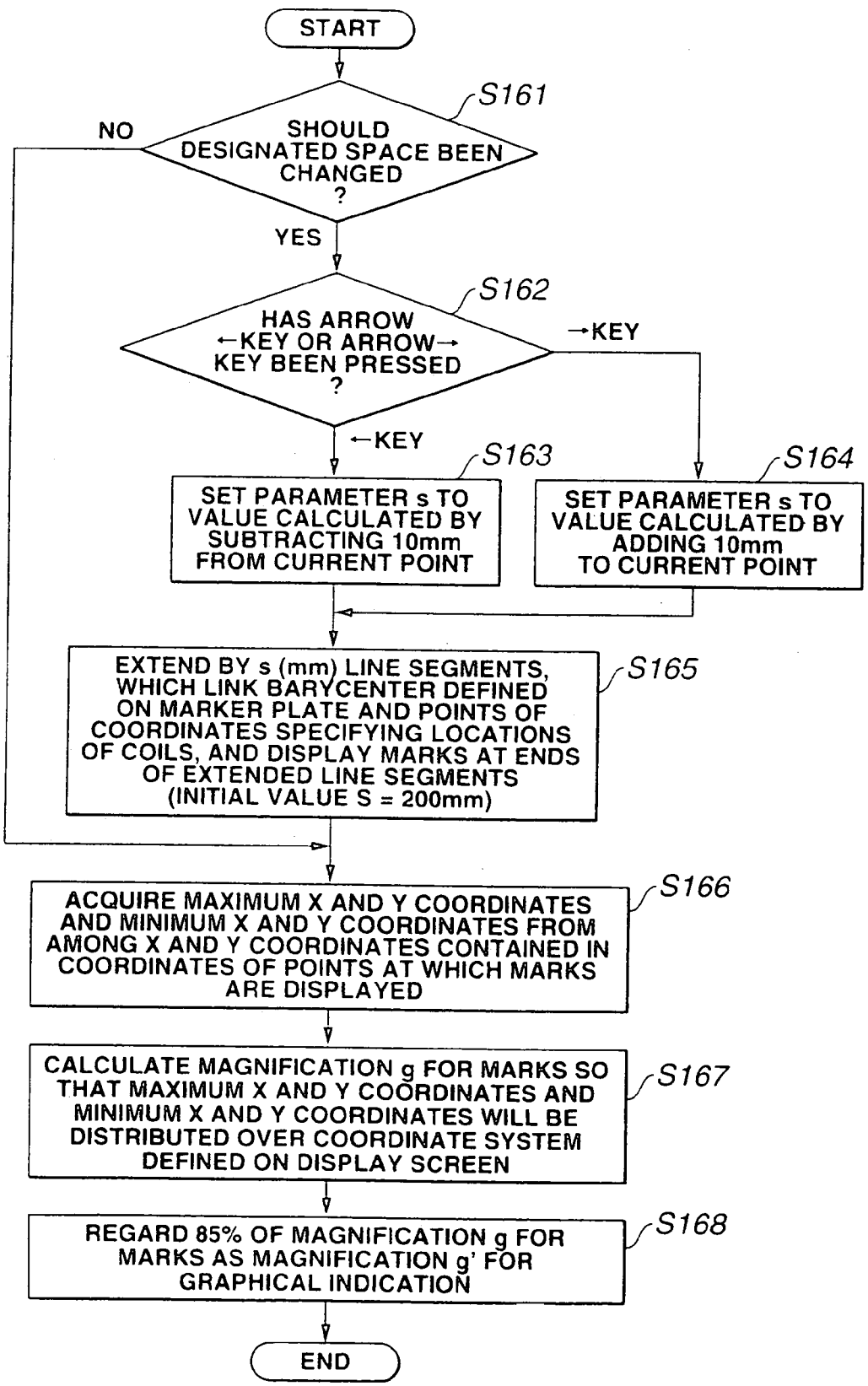

Furthermore, the marks 121a, 121b and 121c can be zoomed in or out to any size on the monitor 24. As shown in FIG. 41, first, it is judged at step S161 whether a request has been made to change the magnification (zoom). If a request has been made using operator pad 114 to change the magnification (zoom), the process proceeds to step S162. If such a request has not been made, the process proceeds to step S1166.

At step S162, it is judged whether a left arrow (←) key or right arrow (→) key has been pressed at the operation pad 114. If the left arrow (←) key has been pressed, the process proceeds to step S163. If the right arrow (→) arrow key has been pressed, the process proceeds to step S164.

At step S163, a parameter s is set to a value calculated by subtracting 10 mm from the coordinates of a current point. The process then proceeds to step S165. At step S164, the parameter s is set to a value calculated by adding 10 mm to the coordinates of the current point, and the process then proceeds to step S165.

At step S165, line segments linking the barycenter of the coordinate system defined on the marker plate 112 and the coordinates of points specifying the locations of the coils represented by the lower mark 121a, right mark 121b, and left mark 121c are extended by s (mm). The lower mark 121a, right mark 121b, and left mark 121c are then displayed at the ends of the extended line segments, and the process then proceeds to step S166.

Figure 42:
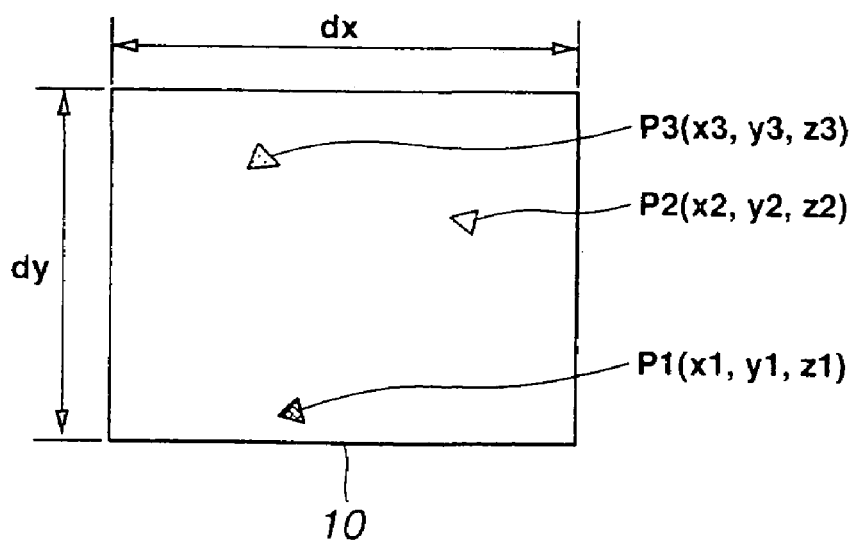

At step S166, maximum X and Y coordinates and minimum X and Y coordinates are selected from among the X and Y coordinates contained in the coordinates of the points at which the marks are displayed. For example, when the marks are displayed as shown in FIG. 42, the minimum X coordinate Xmin equals x3, the maximum X coordinate Xmax equals x2, the minimum Y coordinate Ymin equals y1, and the maximum Y coordinate Ymax equals y3.

At step S167, a magnification g for the marks is calculated so that the maximum and minimum X and Y coordinates will be distributed as widely as possible over the coordinate system defined on the display screen. In the case of the marks shown in FIG. 42, gx=dx/(Xmax-Xmin) and gy=dy/(Ymax-Ymin) are solved. If gx≦gy, the magnification g is set to gx. If gx>gy, the magnification g is set to gy.

At step S168, 85% of the magnification g for the marks is regarded as a magnification g' for graphical indication (=g×0.85). The process is then terminated.

The zoom process described in FIG. 41 makes it possible to graphically indicate the shape of the endoscope at the largest possible size on the monitor 24 in relation to the display marks representing the marker coils.

According to the present embodiment, the shape of the endoscope having been rotated or zoomed in or out can be reset to an initial state merely by pressing a Reset button provided on the operator pad 114. Moreover, the shape of the endoscope having been rotated or zoomed in or out can be registered (stored) using the operator pad 114. The registered shape of the endoscope can also be retrieved easily using the operator pad 114.

According to the present embodiment, a reference point, or more particularly, the coordinates of a reference point is (are) calculated, and the coordinates of a point specifying the distal position of the insertion unit 7 that has just been inserted is shifted in parallel to the reference point. Even if the patient changes his/her posture, the graphical indication of the shape of the endoscope can be maintained to be in the center of the monitor 24.

Moreover, the shape of the extracorporeal portion of the endoscope can be cut from the graphical indication. In particular, the display of the graphical indication of the endoscope shape can be controlled so that only the portion of the endoscope (for example, the portion inserted into a patient's body) which a user desires to view carefully is graphically indicated for observation during the entire session.

Furthermore, the coordinate system defined on the marker plate 112 is aligned with the coordinate system defined on the display screen. Also, the coordinate system defined on the marker plate 112 is shifted in parallel so that the y axis thereof will pass through the coordinates of the point specifying the location, of the extracorporeal coil 113 or the distal position of the insertion unit 7 that has just been inserted. Consequently, the shape of the endoscope can be graphically indicated with a viewing point set at an angle such that the endoscope shape can be easily observed, while being unaffected by a change in the patient's posture.

The ninth embodiment of the present invention will now be described with reference to FIG. 43 through FIG. 61.

Figure 43:
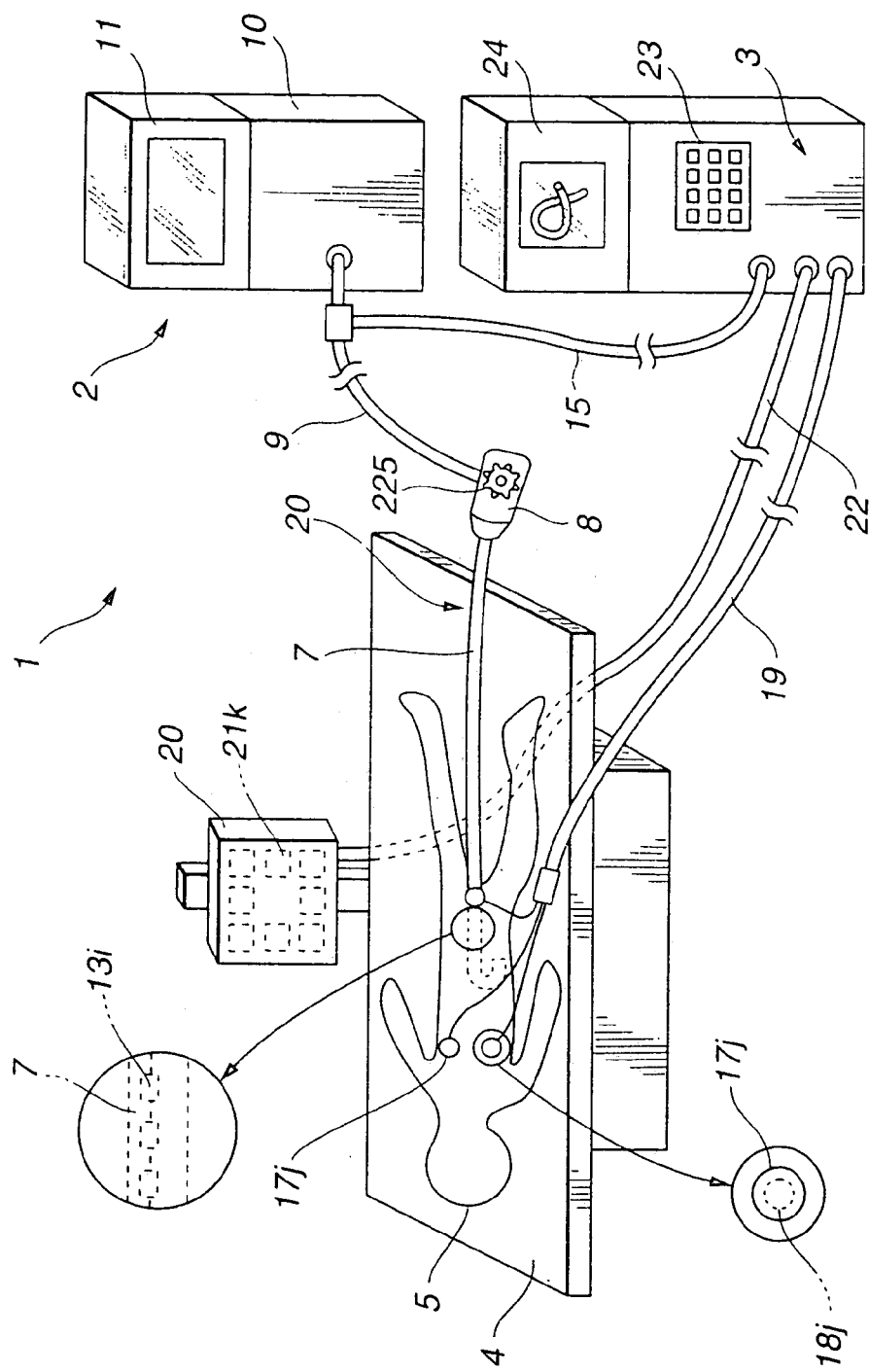
Figure 44:
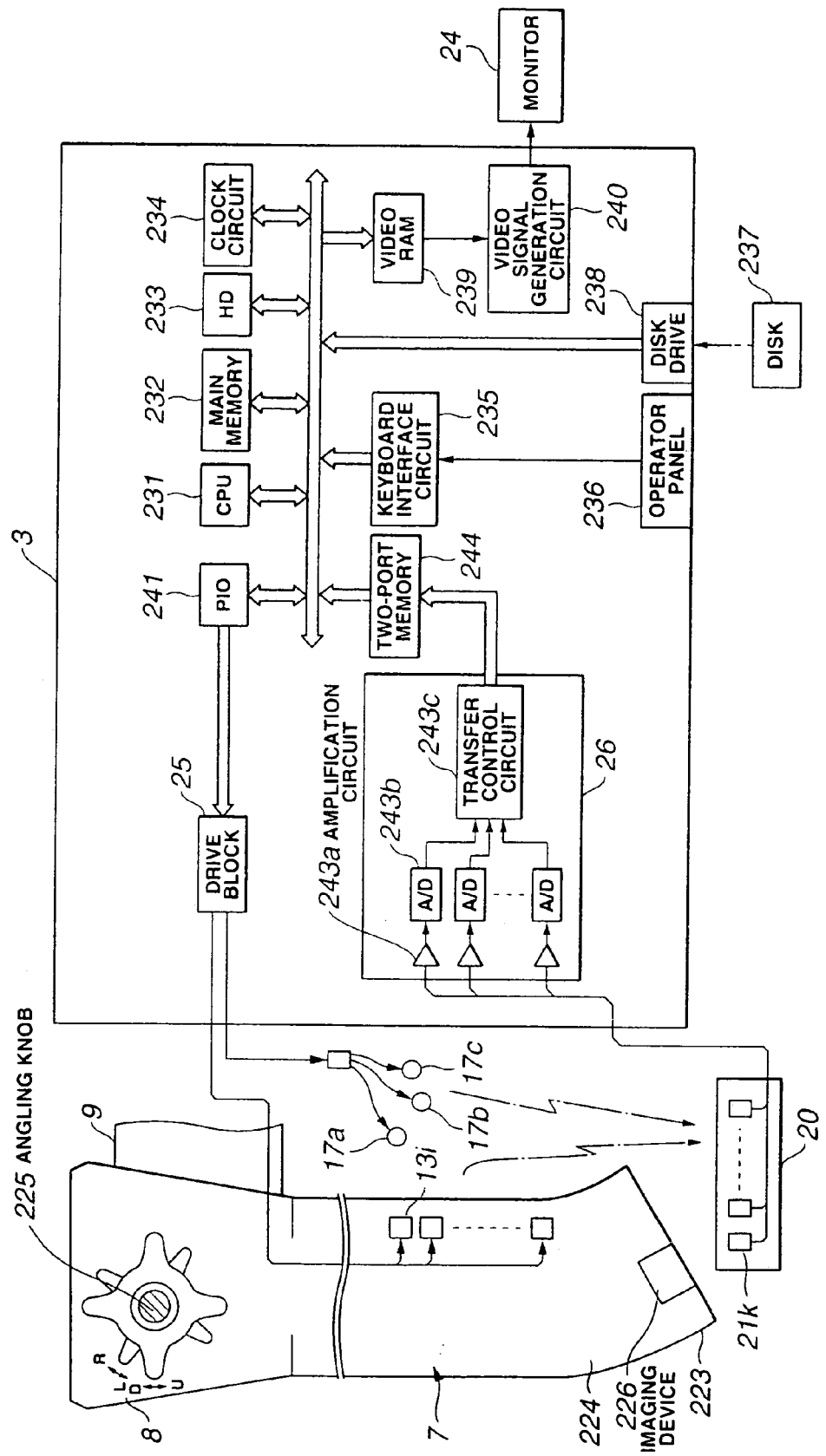

As shown in FIG. 43 and FIG. 44, the endoscope 6 has the elongated insertion unit 7 to be inserted into a body cavity. The plurality of source coils 13*i* is arranged at predetermined intervals along the length of the insertion unit 7. The operation unit 8 serving as a hand-held portion and communicating with the proximal end of the insertion unit 7 has an angling knob 225. By handling the angling knob 225, a bending portion 224 of the insertion unit 7 is angled in order to change the orientation of a distal part 223 of the insertion unit 7. An imaging device 226 is incorporated in the distal part 223 and embodied as, for example, a charge coupled device (CCD) for imaging an object and producing an image signal.

The angling knob 225 has a vertical angling knob used to angle the bending portion 224 upward or downward and a lateral angling knob used to angle the bending portion 224 leftward or rightward. Moreover, when the operation unit 8 is turned, the torque is conveyed to the insertion unit 7.

The shape-of-endoscope detecting apparatus 3 consists generally of a central processing unit (hereinafter CPU) 231, a main memory 232, a hard disk 233, a clock circuit 234, an operator panel 23, a disk drive 238, a video RAM 239, video signal generation circuit 240, the drive block 25, the detection block 26, and a two-port memory 244. The CPU 231 is responsible for primary control of the shape-of-endoscope detecting apparatus 3. The main memory 232 is connected to the CPU 231. Programs to be run by the CPU 231 or working data to be treated by the CPU 231 are stored in the main memory 232. The hard disk 233 is connected to the CPU 231. Programs to be run by the CPU 231 are stored in the hard disk 233, and data to be treated by the CPU 231 is stored and held in the hard disk 233. The clock circuit 234 is connected to the CPU 231, and informs the CPU 231 of a current date (year/month/day) and a current time (hour/min/sec). The operator panel 23 is connected to the CPU 231 via a keyboard interface circuit 235 and is used to issue an instruction to the shape-of-endoscope detecting apparatus 3 or to input data thereto. The disk drive 238 is connected to the CPU 231. A flexible disk 237 such as an auxiliary storage medium can be loaded into the disk drive 238. The video RAM 239 is connected to the CPU 231. Image data according to which an image is displayed on an image observation monitor 11 (FIG. 43) is temporarily stored in the video RAM 239. The video signal generation circuit 240 converts the image data temporarily stored in the video RAM into a video signal to thereby enable display of an image on a monitor, and outputs the resultant data to the monitor 24. The drive block 25 is controlled by the CPU 231 via a parallel input/output circuit (PIO) and drives the marker coils 18*a*, 18*b*, and 18*c* and the source coils 13*i*. The detection block 26 feeds signals sent from the sensor coils 21*k* to the shape-of-endoscope detecting apparatus 3. The two-port memory 244 is interposed between the detection block 26 and the CPU 231 and used to buffer signals sent from the sensor coils 21*k* and output from the detection block 26.

The detection block 26 consists of an amplification circuit 243*a*, an A/D conversion circuit 243*b*, and a transfer control circuit 243*c*. The amplification circuit 243*a* amplifies signals sent from the sensor coils 21*k*. The A/D conversion circuit 243*b* converts the signals output from the amplification circuit 243*a* from an analog form to a digital form. The transfer control circuit 243*c* transfers the signals output from the A/D conversion circuit 243*b* to the two-port memory 244.

Figure 45:
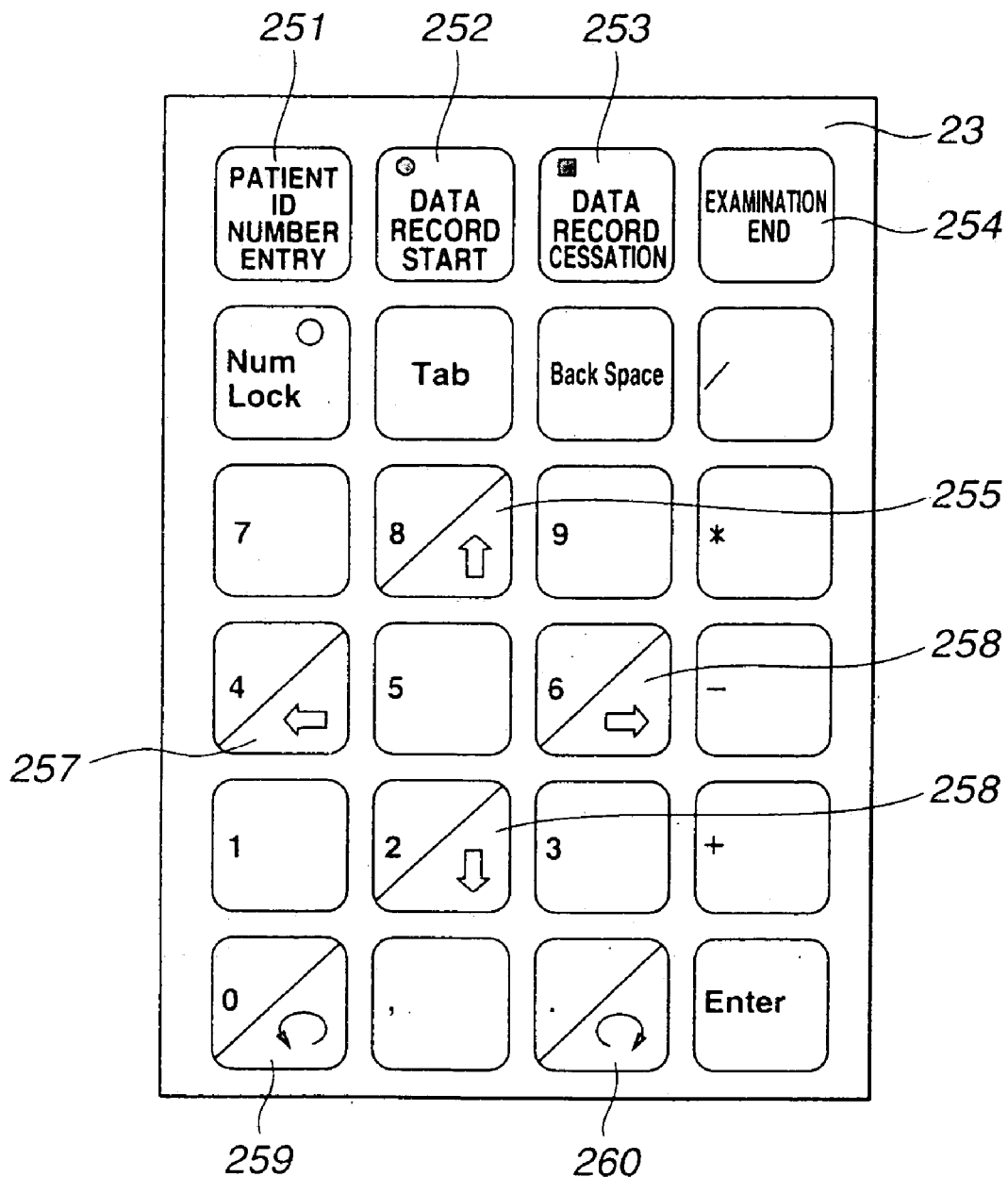

As shown in FIG. 45, the operator panel 23 has a plurality of buttons used to enter numerals or symbols. Specifically, a button 251 is used to invoke a patient identification number (hereinafter abbreviated to "ID number") entry window, which will be described later and in which a patient ID number assigned to the patient 5 is entered at the start of the examination to be performed on the patient 5. A button 252 is used to start the writing of examination information concerning the patient 5 into an examination record file that will be described later. A button 253 is used to terminate the writing of data into the examination record file. A button 254 is used to terminate the examination. Buttons 255, 256, 257, and 258 are used to manually inform the shape-of-endoscope detecting apparatus 3 of the fact that the bending portion has been angled upward, downward, leftward, or rightward. Buttons 259 and 260 are used to manually inform the shape-of-endoscope detecting apparatus 3 of the fact that the operation unit 8 has been turned in order to rotate the insertion unit 7 counterclockwise or clockwise.

Figure 46:
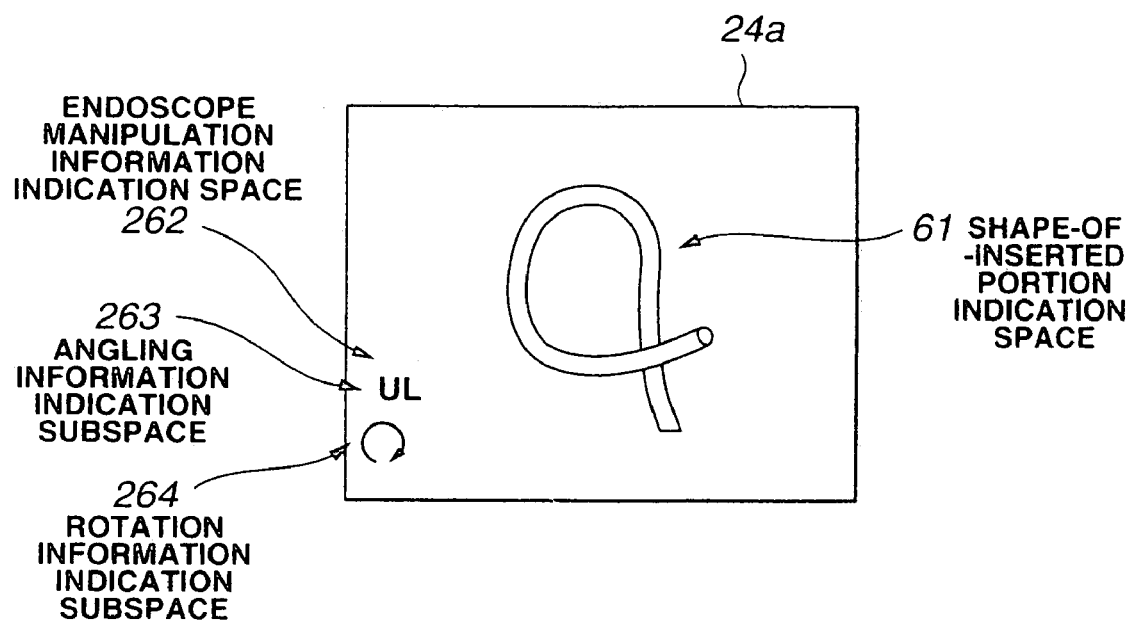
Figure 47:
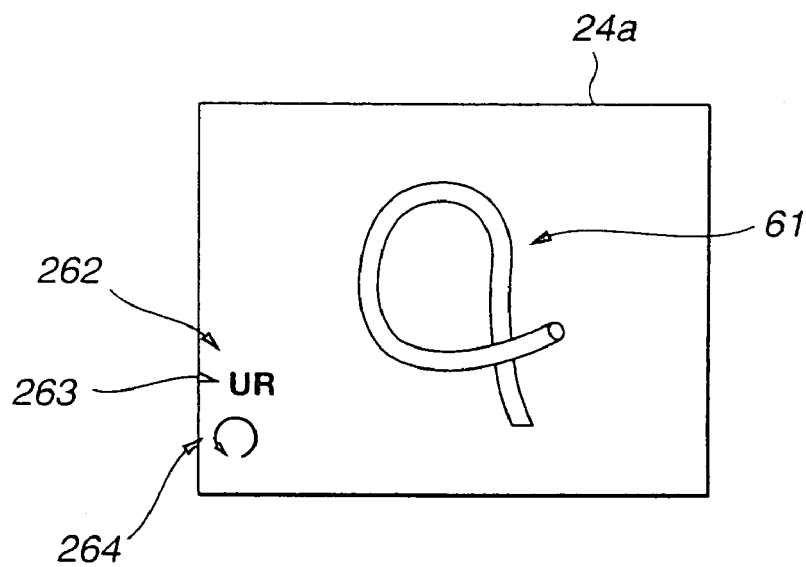

As shown in FIG. 46 and FIG. 47, the screen 24*a* of the monitor 24 has a shape-of-inserted portion indication space 261 and an endoscope manipulation information indication space 262 defined therein. The shape of the insertion unit 7 is indicated in the shape-of-inserted portion indication space 261, and manipulation information concerning the endoscope 6 is indicated in the endoscope manipulation information indication space 262.

The endoscope manipulation information indication space 262 consists of an angling information indication subspace 263 in which angling information is indicated, and a rotation information indication subspace 264 in which rotation information is indicated.

In the graphical indication example shown in FIG. 46, a letter U indicating that the bending portion has been angled upward is displayed in the angling information indication subspace 263. Moreover, a letter L indicating that the bending portion has been angled leftward is displayed in the angling information indication subspace 263. A mark indicating that the insertion unit has been rotated clockwise is displayed in the rotation information indication subspace 264.

In the graphical indication example shown in FIG. 47, a letter D serving as a mark indicating that the bending portion has been angled downward is displayed in the angling information indication subspace 263. Moreover, a letter R serving as a mark indicating that the bending portion has been angled rightward is displayed in the angling information indication subspace 263. A mark indicating that the insertion unit has been rotated counterclockwise is displayed in the rotation information indication subspace 264.

As shown in FIG. 48, the CPU 231 includes a shape-of-inserted portion detecting/indicating unit 271, and an endoscope manipulation information indicating/recording unit 273. The shape-of-inserted portion detecting/indicating unit 271 detects the shape of an inserted portion of an endoscope, graphically indicates the shape of the inserted portion, and outputs graphical data, which represents the shape of the inserted portion, to the video RAM 239. The endoscope manipulation information indicating/recording unit 273 outputs endoscope manipulation information to the video RAM 239, or creates an examination record file 272, which contains shape-of-inserted portion information and endoscope manipulation information, in the hard disk 233.

The shape-of-inserted portion detecting/indicating unit 271 consists of a source coil location detection block 271a, a shape-of-inserted portion arithmetic processing block 271b, and a graphical indication block 271c. The source coil location detection block 271a drives the marker coils 18j and source coils 13i, analyzes signals sent from the sensor coils 21k according to a known method, and calculates coordinates (X, Y, Z) in a three-dimensional space specifying the location of each of the marker coils 18j and source coils 13i. The shape-of-inserted portion arithmetic processing block 271b detects the shape of an inserted portion of the insertion unit 7 using a known technique according to the location information of the source coils provided by the source coil location detection block 271a. The graphical indication block 271c graphically indicates the shape of the insertion unit 7 using a known technique according to the shape of the inserted portion detected by the shape-of-inserted portion arithmetic processing block 271b, and outputs graphical data to the video RAM 239.

The endoscope manipulation information indicating/recording unit 273 outputs endoscope manipulation information to the video RAM 239 by referencing information input from any of the buttons 255 to 258, 259, and 260 on the operator panel 23. Moreover, the endoscope manipulation information indicating/recording unit 273 has the ability to write data into the examination record file 272. At this time, the endoscope manipulation information indicating/recording unit 273 references date/time information output from the clock circuit 234, endoscope manipulation information input from the buttons 255 to 258, 259, and 260 on the operator panel 23, and location information of the source coils output from the source coil location detection block 271a.

The video RAM 239 superimposes graphical data output from the endoscope manipulation information indicating/recording unit 273 onto graphical data output from the shape-of-inserted portion detecting/indicating unit 271.

Figure 49A:
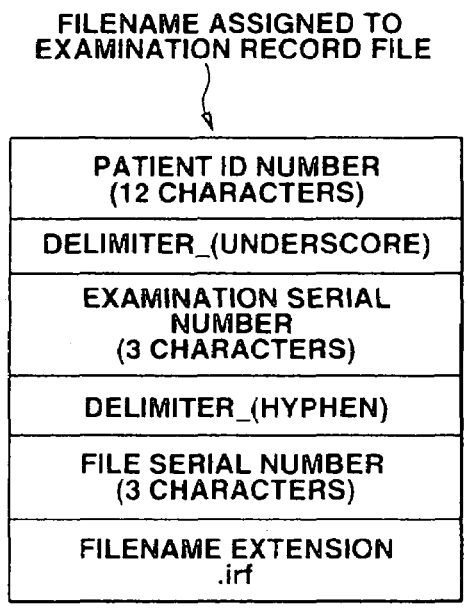
FIG. 49A is an explanatory diagram of an example of a data structure for a filename to be assigned to an examination record file.

As shown in FIG. 49A, a filename assigned to the examination record file 272 is represented by a character string. The character string includes, for example, a patient ID number (which will be described later), a delimiter_ (underscore), an examination serial number composed of, for example, three characters, a delimiter—(hyphen), a file serial number composed of, for example, three characters, and a filename extension, for example, .irf, arranged in the order shown.

Figure 49B:
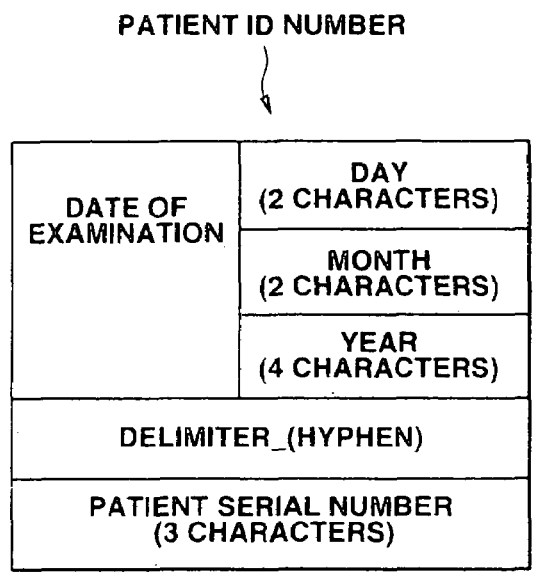
FIG. 49B is an explanatory diagram of an example of a data structure for a patient identification number.

The patient ID number is, as shown in FIG. 49B, expressed with a character string including a date of examination composed of, for example, eight characters, delimiter—(hyphen), and a patient serial number composed of, for example, three characters arranged in that order.

The patient serial number is a serial number assigned to a patient on the day of examination. The examination serial number is a serial number assigned to each examination performed on a patient identified with specific patient ID number on the day of examination. The file serial number is a serial number assigned to the examination record file 272 to be created in relation to the examination performed on the patient.

For example, a patient ID number assigned to the first patient on Jun. 2, 1999 may be expressed as 02061999-001. Moreover, a file name assigned to the first examination record file to be created in relation to the first examination performed on the patient assigned the above patient ID number on the day of examination is expressed as 02061999-001_001-001.irf.

Figure 50:
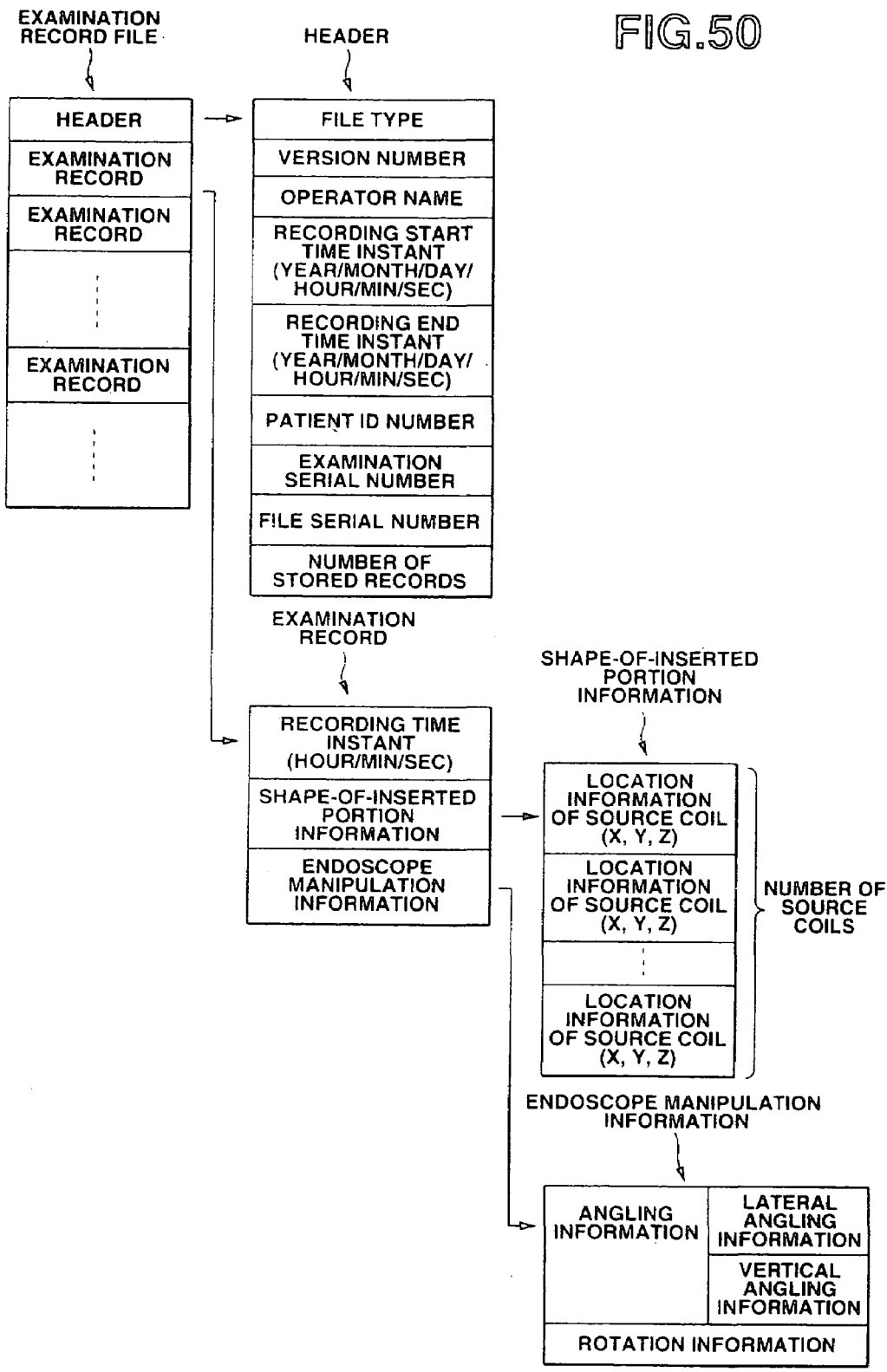

As shown in FIG. 50, the examination record file 272 is composed of a header and a plurality of examination records to be appended to the header.

The header is composed of a file type, a version number, an operator name, a recording start time, a recording end time, a patient ID number, an examination serial number, a file serial number, and the number of stored records. A code indicating a file type is specified for the file type. A version number of the shape-of-endoscope detecting apparatus 3 is specified for the version number. The number of stored examination records is specified for the number of stored records.

Each examination record is composed of a recording time, shape-of-inserted portion information, and endoscope manipulation information.

The shape-of-inserted portion information is composed of a plurality of sets of coordinates (X, Y, Z) in a three-dimensional space specifying locations of the source coils.

The endoscope manipulation information is composed of, for example, angling information and rotation information. The angling information contains lateral angling information and vertical angling information.

Figure 51:
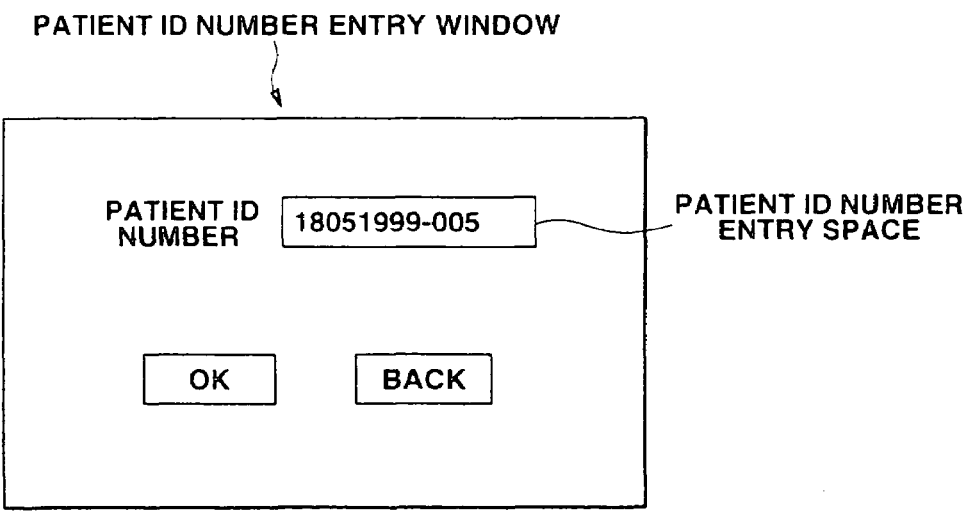

For example, a patient ID number entry window shown in FIG. 51 and invoked by pressing the button 251 on operator panel 23 has the term "Patient ID Number" displayed therein. Moreover, the patient ID number entry window has a patient ID number entry field, in which a patient ID number is to be entered. When the button labeled "OK" is clicked, the entered patient ID number is inputted to the CPU 231.

Now, a description will be made of the operation of the present embodiment.

When the endoscope 6, is inserted into a body cavity, the, imaging device 226 images an object in the body cavity and produces an image signal. The image signal is converted into a video signal, which enables display of the image on a monitor, by the video processor 10. The endoscopic image is then displayed on the monitor 24.

Magnetic fields induced by the marker coils 18j and source coils 13i driven by the shape-of-endoscope detecting apparatus 3 are detected by the sensor coils 21k. Signals output from the sensor coils 21k are fed to the shape-of-endoscope detecting apparatus 3. The source coil location detection block 271a provided in the CPU 231 which in turn is included in the shape-of-endoscope detecting apparatus 3 detects the locations of the marker coils 18*j* and source coils 13*i*. The shape-of-inserted portion arithmetic processing block 271*b* detects the shape of an inserted portion according to the source coil location information. The graphical indication block 271*c* writes graphical data in the video RAM 239 according to the shape of the inserted portion detected by the shape-of-inserted portion arithmetic processing block 271*b*. Consequently, the shape of the endoscope is graphically indicated on the screen 24*a* of monitor 24.

Next, a description will be provided for the operation of the endoscope manipulation information indicating/recording unit 273.

Figure 52:
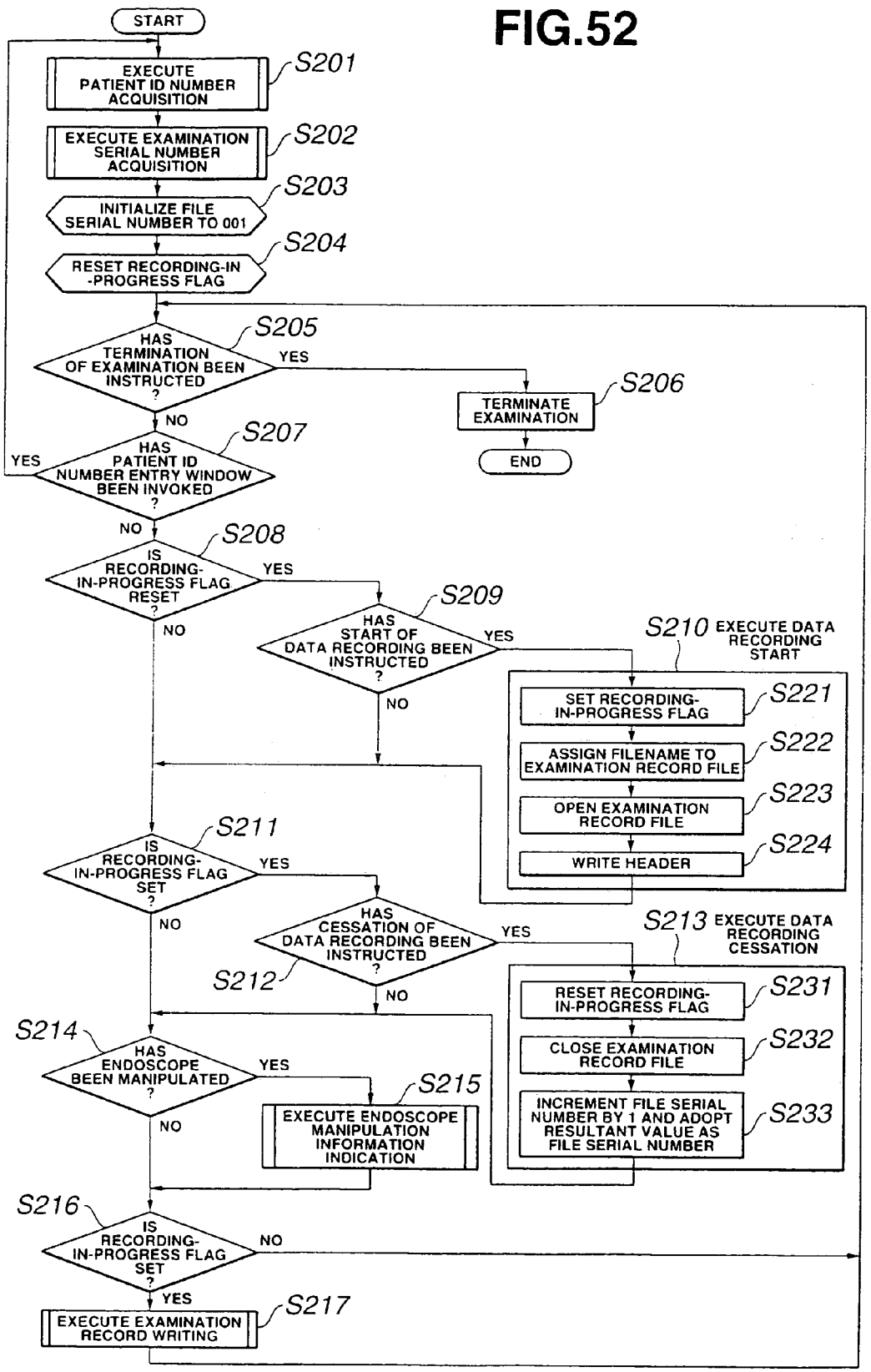

As described in FIG. 52, when the endoscope manipulation information indicating/recording unit 273 is activated, it executes a patient ID number acquisition process at step S201 to acquire a patient ID number. At step S202, an examination serial number acquisition process is executed in order to acquire an examination serial number. At step S203, a file serial number is initialized to 001. At step S204, a recording-in-progress flag indicating that the recording of data into the examination record file 272 is in progress is reset.

At step S205, it is judged whether termination of an ongoing examination has been instructed using the operator panel 23. If termination of the examination has been instructed, the process proceeds to step S206, whereupon termination of the examination is then executed. If termination of an ongoing examination has not been instructed, the process proceeds to step S207.

At step S207, it is judged whether the patient ID number entry window has been invoked at the operator panel 23. If the patient ID number entry window has been invoked, the process returns to the patient ID number acquisition process of step S201. If the patient ID number entry window has not been invoked, the process proceeds to step S208.

At step S208, the recording-in-progress flag indicating that recording data in the examination record file 272 is in progress is checked. If data recording is in progress, that is, if the recording-in-progress flag has been set, the process proceeds to step S211. If data recording is not in progress, that is, the recording-in-progress flag has been reset, the process proceeds to step S209.

At step S209, it is judged whether an instruction to start the recording of data has been given using the operator panel 23. If an instruction to start process recording data has been given, a data recording start process is executed at step S210, and then the process proceeds to step S211. If no instruction to start recording data has been given, the process proceeds directly from step S209 to step S211.

At step S211, the recording-in-progress flag indicating that the recording of data in the examination record file 262 is in progress is checked. If data recording is not in progress, that is, the recording-in-progress flag has been reset, the process proceeds to step S214. If data recording is in progress, that is, the recording-in-progress flag has been set, the process proceeds to step S212.

At step S212, it is judged whether cessation of data recording has been instructed using the operator panel 23. If cessation of data recording has been instructed, data recording cessation is executed at step S213. The process then proceeds to step S214. If cessation of data recording has not been instructed, the process proceeds directly from step S212 to step S214.

At step S214, it is judged whether the endoscope has been manipulated. If the endoscope has been manipulated, the process proceeds to step S215. Endoscope manipulation information indication is then executed, and the process proceeds to step S216. If the endoscope has not been manipulated, the process proceeds directly from step S214 to step S216. According to the present embodiment, whether the endoscope has been manipulated is judged by checking if endoscope manipulation information has been entered using the operator panel 23.

At step S216, the recording-in-progress flag indicating that the recording of data into the examination record file 272 is in progress is checked. If data recording is not in progress, that is, the recording-in-progress flag has been reset, the process returns to step S205. If data recording is in progress, that is, the recording-in-progress flag has been set, an examination record writing process is executed at step S217. The process then returns to step S205.

During the data recording start process executed at step S210, for example, the recording-in-progress flag is set at step S221. A filename to be assigned to the examination record file 272 is created at step S222. The examination record file 272 is newly created and opened at step S223. A header is recorded in the examination record file 272 at step S224.

During the data recording cessation process executed at step S213, for example, the recording-in-progress flag is reset at step S231. The examination record file 272 is closed at step S232. The file serial number is incremented by one at step S233.

Figure 53:
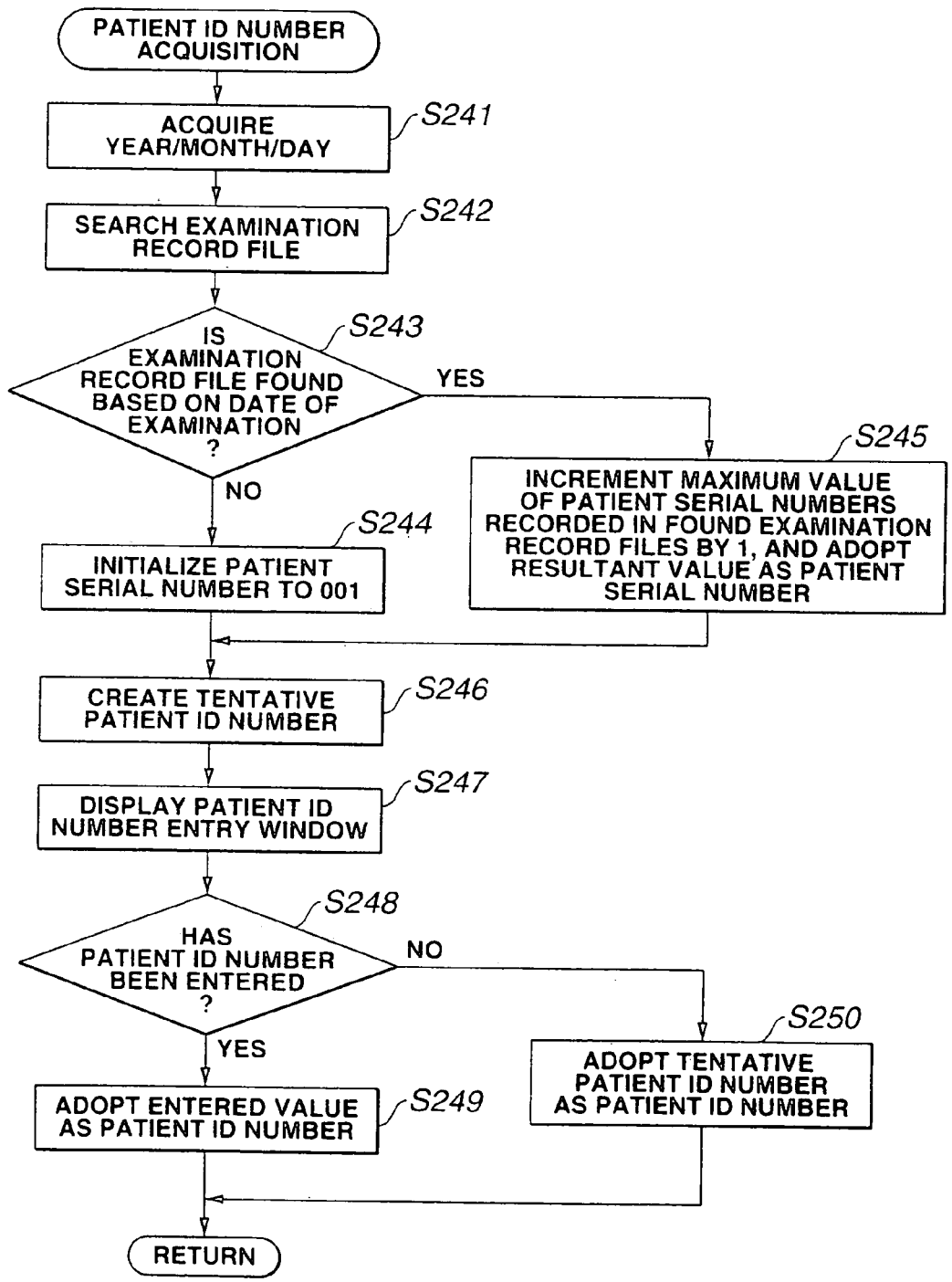

As described in FIG. 53, in the patient ID number acquisition process executed at step S201 in FIG. 52, first, the year/month/day indicating the day of examination is acquired at step S241. The examination record file 272 is searched based on the date of examination, at step S242. It is judged at step S243 whether the examination record file 272 specified with the date of examination is found from a memory stage location. If the examination record file 272 specified with the date of examination is established at step S241 is not found, the process proceeds to step. S244. The patient serial number is initialized to 001, and the process proceeds to step S246. If the examination record file 272 specified with the date of examination established at step S241 is found to exist in memory at step S243, the process proceeds to step S245. The maximum value among all patient serial numbers specified in the filenames assigned to the existing examination record files 272 is incremented by one, and the resultant value is adopted as the patient serial number for the present operation. The process then proceeds to step S246.

At step S246, a tentative patient ID number is created based on the year/month/day of the date of examination and the patient serial number. The patient ID number entry window is displayed at step S247. At this time, the tentative patient ID number is indicated in the patient ID number entry space in the patient ID number entry window.

At step S248, it is judged whether a new patient ID number has been entered or the tentative patient ID number has been edited in the patient ID number entry window. If a new patient ID number has been entered or the tentative patient ID number has been edited, the process proceeds to step S249. The entered or edited patient ID number is finalized as the patient ID number. The patient ID number acquisition process is then terminated. In contrast, if no new patient ID number has been entered and the tentative patient ID number has not been edited, the tentative patient ID number is finalized as the patient ID number at step S250. The patient ID number acquisition process is then terminated.

Figure 54:
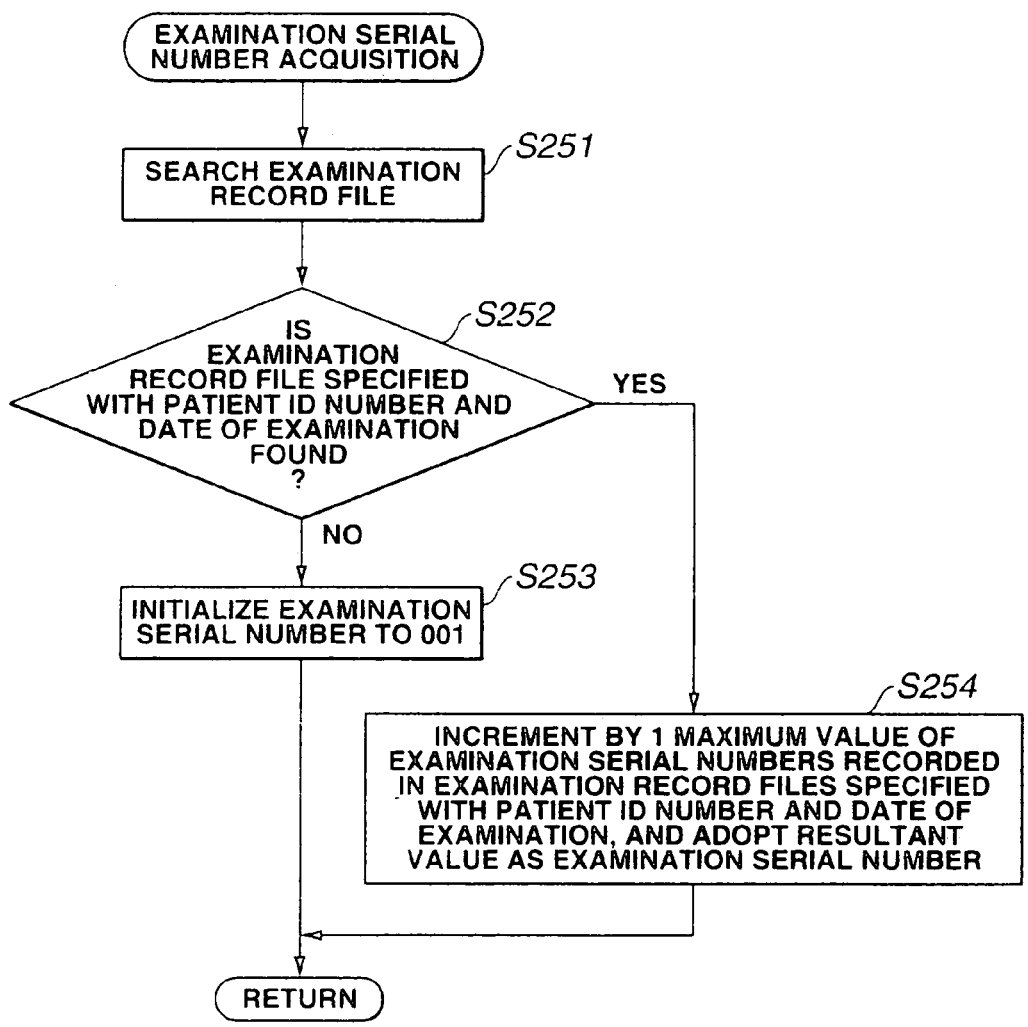

As described in FIG. 54, in the examination serial number acquisition process executed at step S202 in FIG. 52, first, the examination record file 272 is searched at step S251. It is judged at step S252 whether the examination record file 272 specified with the date of examination and the patient ID number established in the process shown in FIG. 53 is found in a memory storage location. If the file is not found, the process proceeds to step S253. The examination serial number is initialized to 001, and the examination serial number acquisition process is terminated. If the file is found to exist in memory at step S252, the process proceeds to step S254. The maximum value among all examination serial numbers specified in the filenames assigned to the existing examination record files 272 specified with the date of examination and the patient ID number established in the process of FIG. 52 is incremented by one. The resultant value is adopted as the examination serial number for the present operation.

The examination serial number acquisition process is then terminated.

Figure 55:
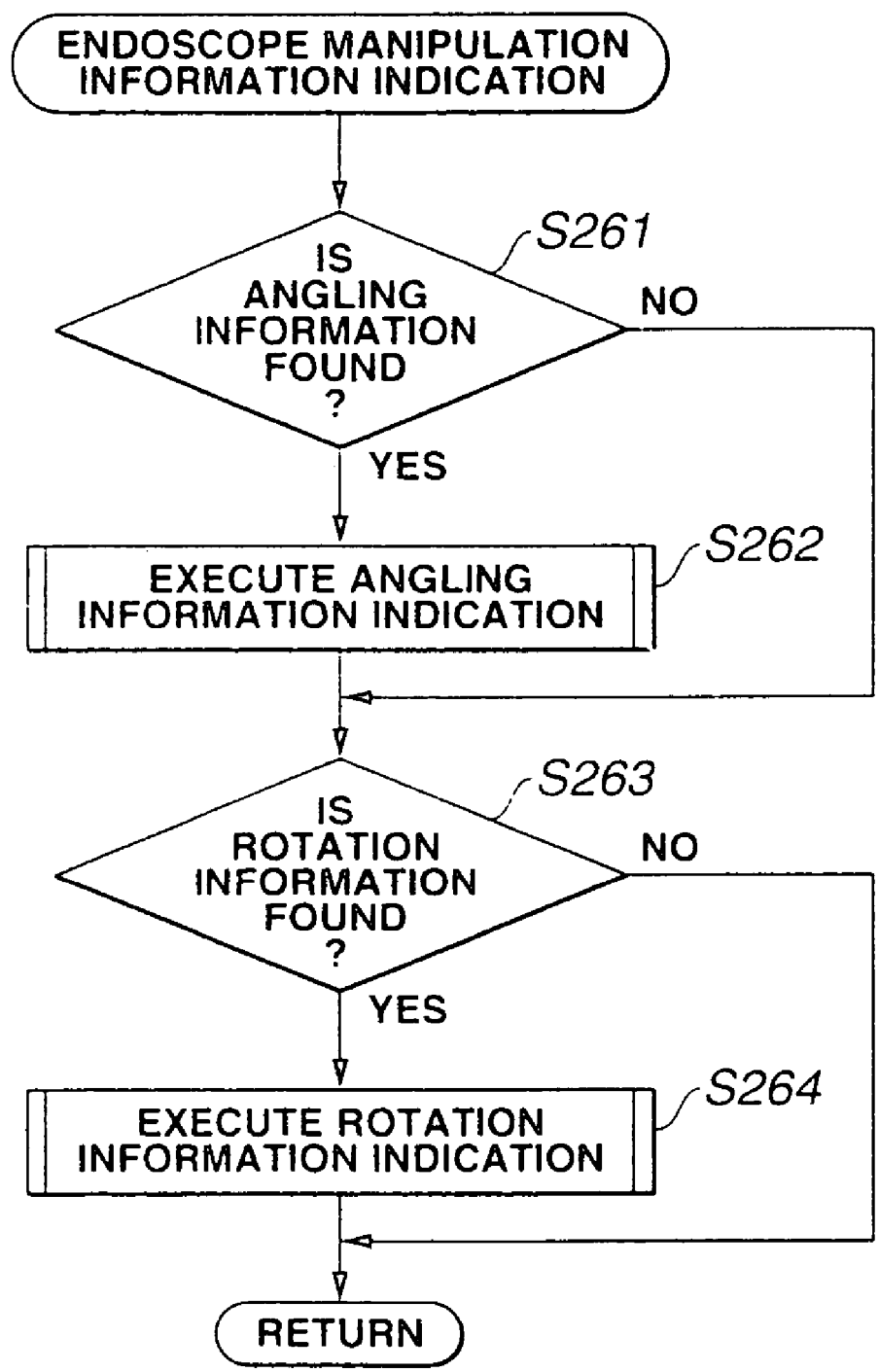

As described in FIG. 55, in the process for displaying endoscope manipulation information executed at step S215 in FIG. 52, it is judged at step S261 whether or not angling information is found. If angling information is found, the process proceeds to step S262, in which a process for displaying angling information is executed, and the process then proceeds to step S263. If no angling information is found, the process proceeds directly from S261 to step S263.

At step S263, it is judged whether or not rotation information is found. If rotation information is found, the process proceeds to step S264. A process for displaying rotation information is then executed, and the process for displaying endoscope manipulation information is terminated. In contrast, if no rotation information is found, the process for displaying endoscope manipulation information is terminated directly from step S263.

Figure 56:
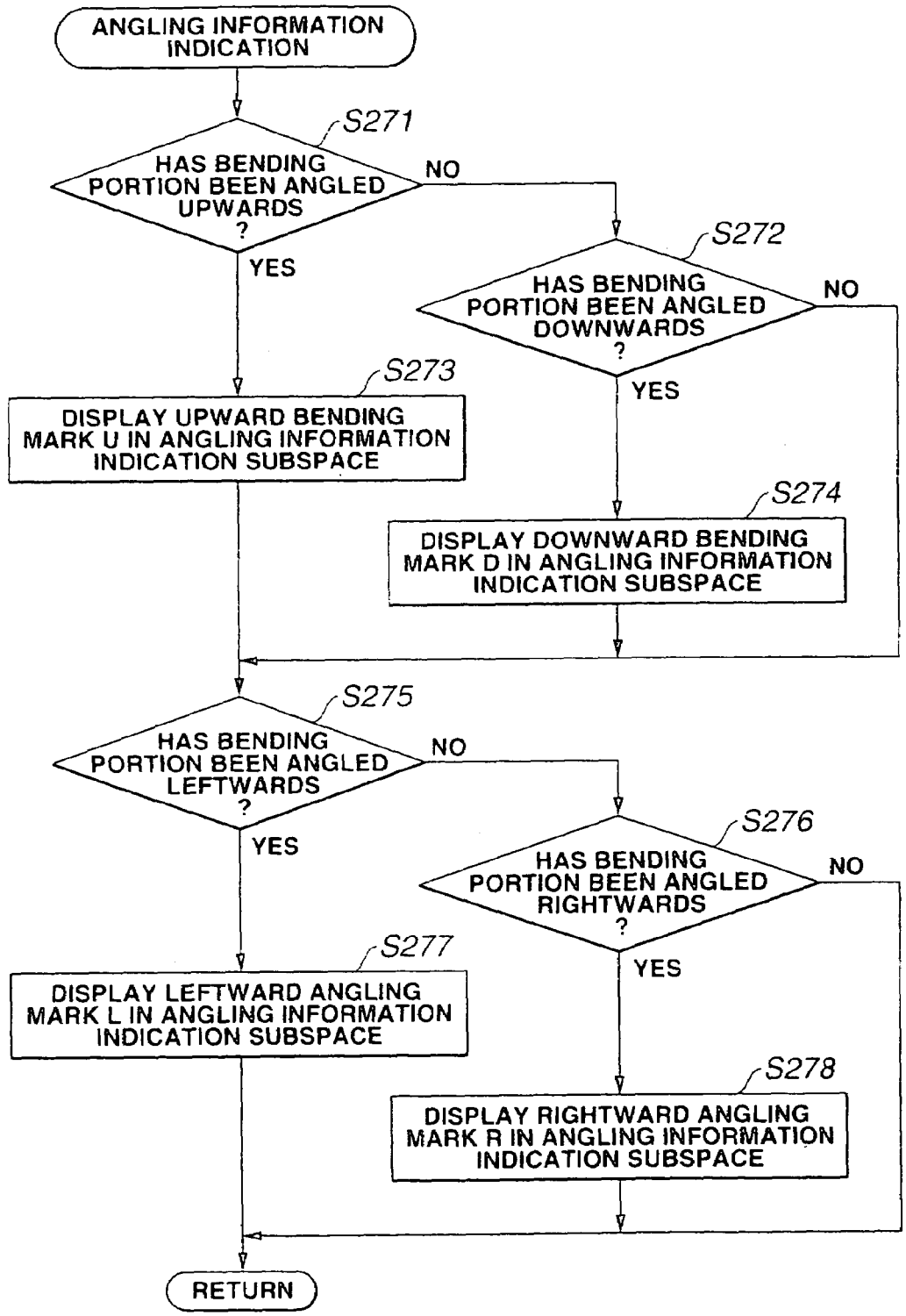

As described in FIG. 56, in the process for displaying angling information executed at step S262 in FIG. 55, first, it is judged at step S271 and step S272 whether or not the bending portion of the endoscope insertion unit has been angled vertically. If the bending portion has been angled upward, the process proceeds from step S271 to step S273, whereupon the upward angling mark U is displayed in the angling information indication subspace 263. The process then proceeds to step S275. If the bending portion has been angled downward, the process proceeds from step S271 through step S272 to step S274, whereupon the downward angling mark D is displayed in the angling information indication subspace 263. The process then proceeds to step S275. If the bending portion has not been angled vertically, the process proceeds from step S271 through step S272 to step S275.

At step S275, first, it is judged whether or not the bending portion has been angled leftward. If the bending portion has been angled leftward, the process proceeds to step S277, whereupon the leftward angling mark L is displayed in the angling information indication subspace 263. The process for displaying angling information is then terminated. In contrast, if the bending portion has not been angled leftward, the process proceeds to step S276. If the bending portion has been angled rightward, the process proceeds to step S278, whereupon the rightward angling mark R is displayed in the bending information indication subspace 263. The process for displaying angling information is then terminated. If the bending portion has not been angled laterally, nothing is carried out at step S275 or step S276 and the process for displaying angling information is then terminated.

Figure 57:
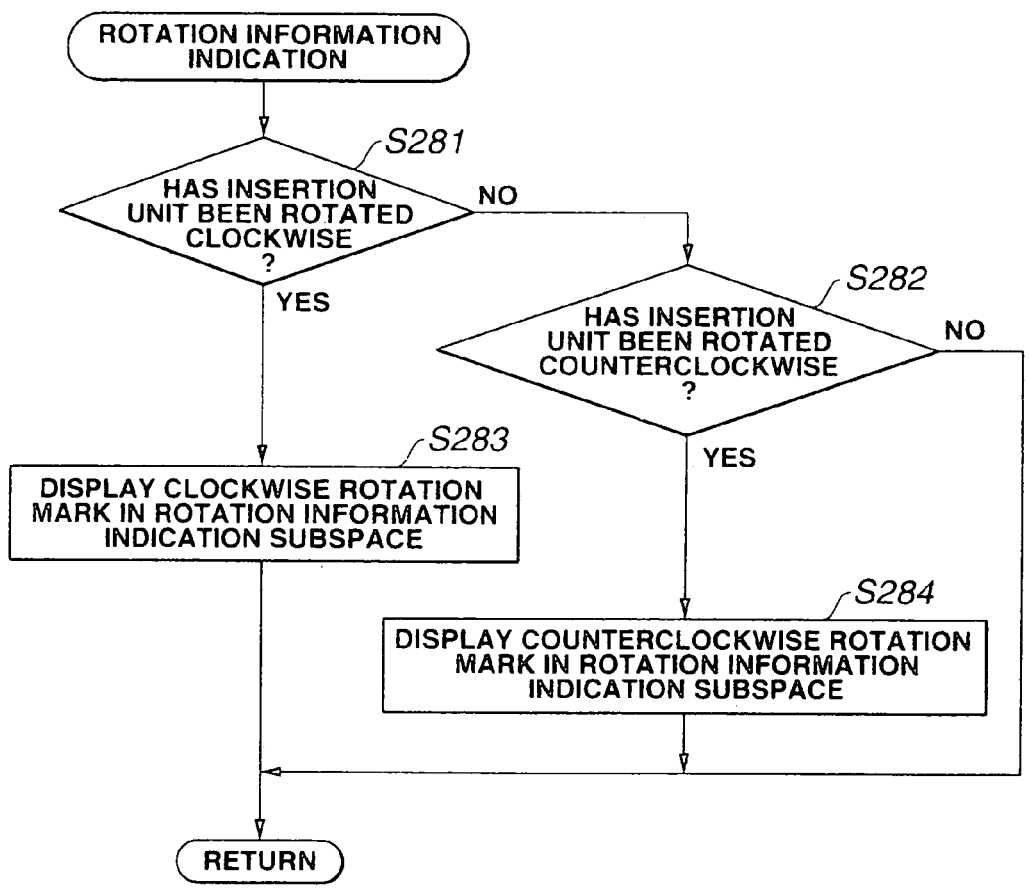

As described in FIG. 57, in the process for displaying rotation information executed at step S264 in FIG. 55, it is judged at step S281 and step S282 whether or not the insertion unit has been rotated. If the insertion unit has been rotated clockwise, the process proceeds from step S281 to step S283, whereupon the clockwise rotation mark is displayed in the rotation information subspace 264. The process for displaying rotation information is then terminated. In contrast, if the insertion unit has been rotated counterclockwise, the process proceeds from step S281 through step S282 to step S284, whereupon the counterclockwise rotation mark is displayed in the rotation information indication subspace 264. The process for displaying rotation information is then terminated. If the insertion unit has not been rotated, nothing is carried out at step S281 or step S282, and the process for displaying rotation information is terminated.

Figure 58:
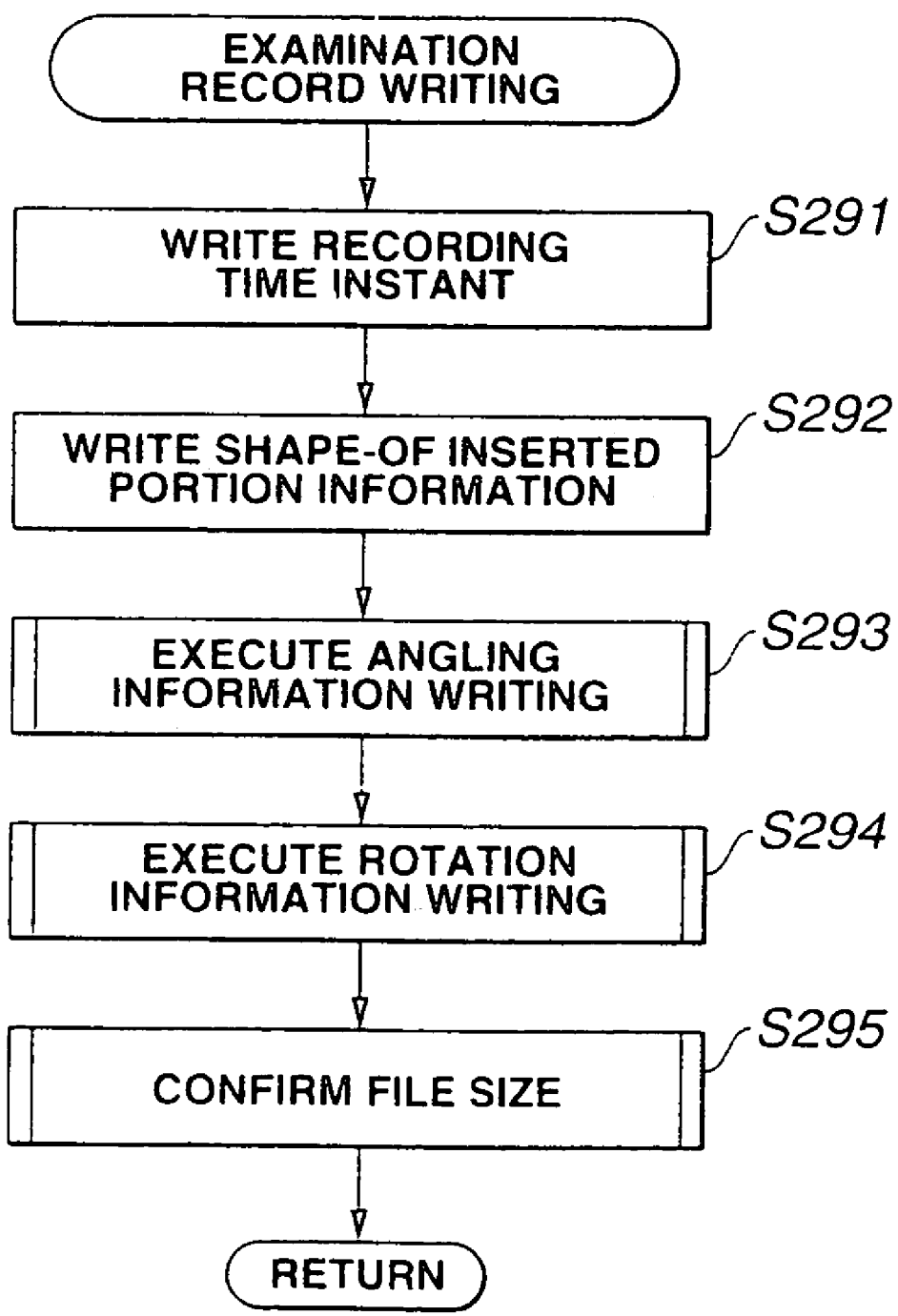

As described in FIG. 58, in the process for writing an examination record as executed at step S217 of FIG. 52, first, the instantaneous time of recording is written at step S291. Information regarding the shape of the inserted portion of the endoscope is written at step S292. Information regarding any angling information performed on the endoscope is written at step S293. Information regarding any rotation operation performed on the endoscope is written at step S294. A file size confirmation process to be described later is then executed at step S295, and then the process for writing an examination record is terminated.

Figure 59:
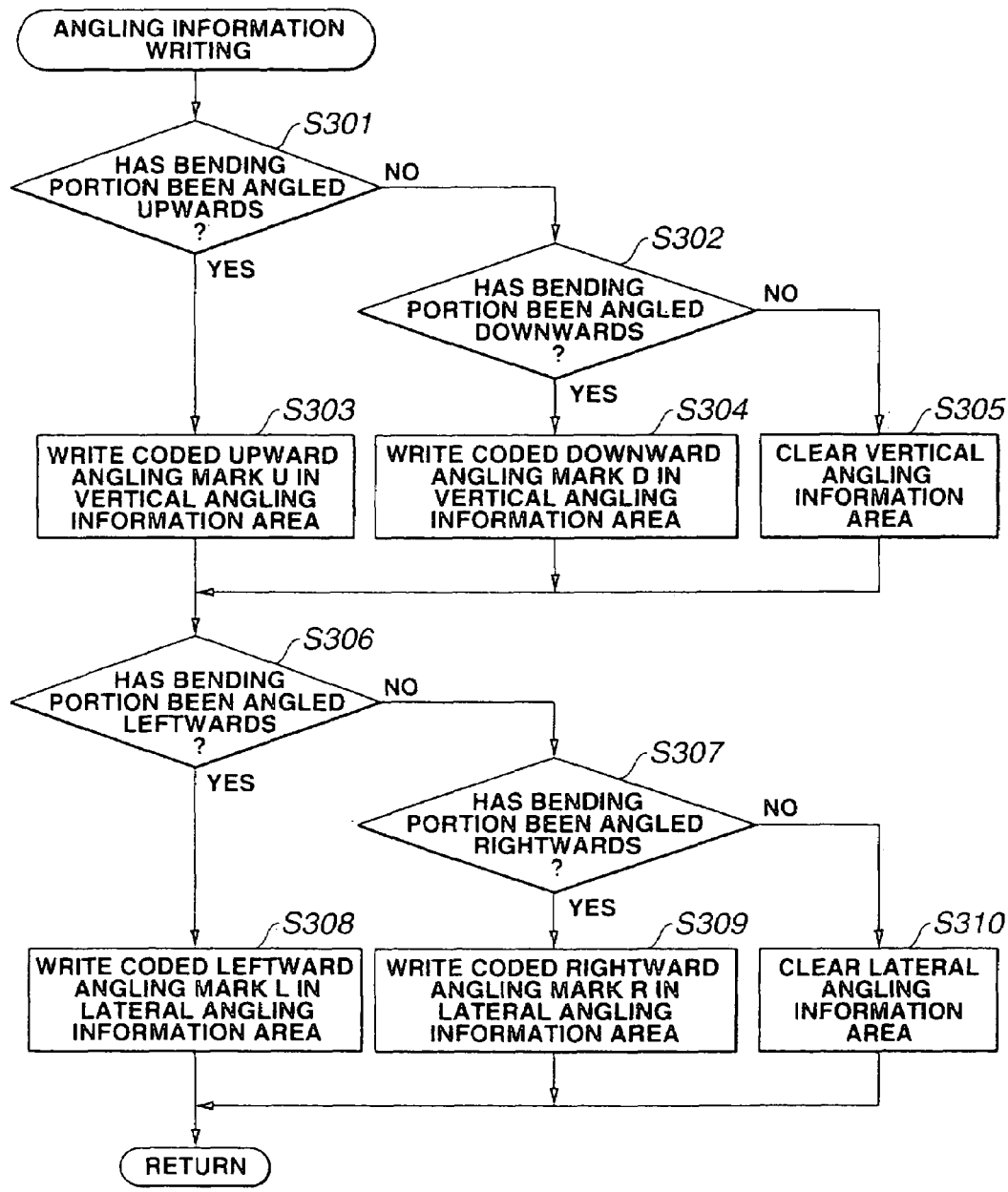

As described in FIG. 59, in the process for writing angling information as executed at step S293 in FIG. 58, first, it is judged at step S301 and step S302 whether or not the bending portion has been angled vertically. If the bending portion has been angled upward, the process proceeds from step S301 to step S303. A coded upward angling mark U is written in a vertical angling information subarea of the examination record. The process then proceeds to step S306. If the bending portion has been angled downward, the process proceeds from step S301 through step S302 to step S304. A coded downward angling mark D is written in the vertical angling information subarea of the examination record. The process then proceeds' to step S306. If the bending portion has not been angled vertically, the process proceeds from step S301 through step S302 to step S305. The vertical angling information subarea is cleared. The process then proceeds to step S306.

At step S306, it is judged whether or not the bending portion has been angled leftward. If the bending portion has been angled leftward, the process proceeds to step S308, whereupon a coded leftward angling mark L is written in a lateral angling information subarea in the examination record. The process for writing angling information is then terminated. In contrast, if the bending portion has not been angled leftward, the process proceeds to step S307, whereupon it is judged whether or not the bending portion has been angled rightward. If the bending portion has been angled rightward, the process proceeds to step S309, whereupon a coded rightward angling mark R is written in the lateral angling information subarea in the examination record. The process for writing angling information is then terminated. If it is judged at step S307 that the bending portion has not been angled rightward, the process proceeds to step S310. The lateral angling information subarea is cleared, and the process for writing angling information is terminated.

Figure 60:
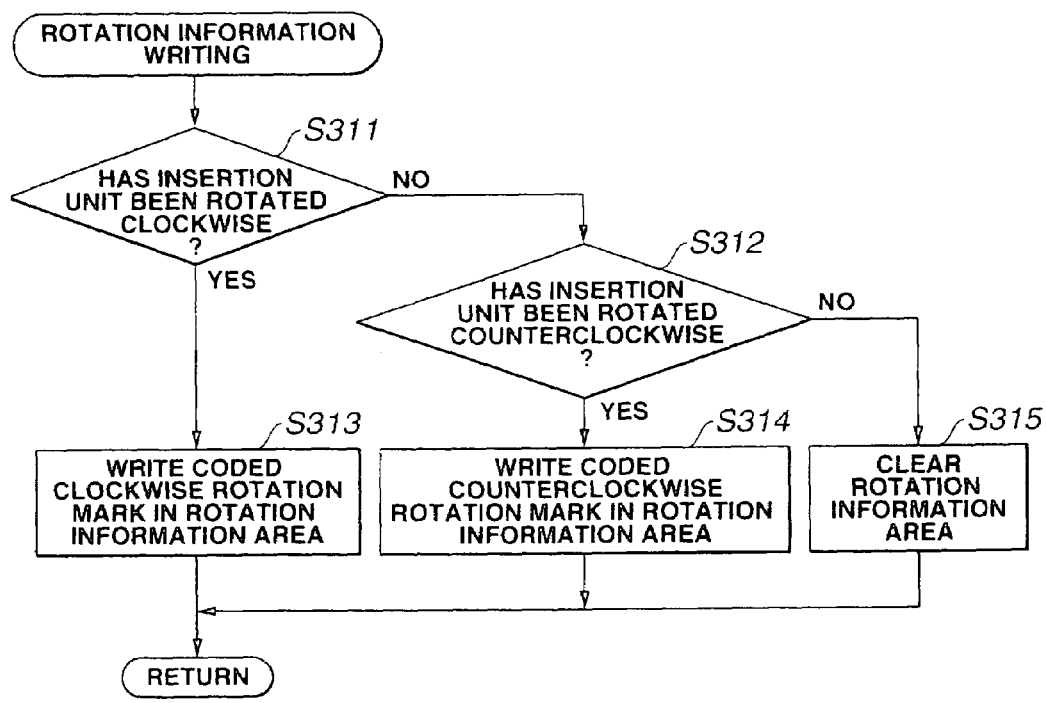

As described in FIG. 60, in the process for writing rotation information as executed at step S294 in FIG. 58, it is judged at step S311 and step S312 whether or not the insertion unit has been rotated. If it is judged at step S311 that the insertion unit has been rotated clockwise, the process proceeds to step S313, whereupon a coded clockwise rotation mark is written in a rotation information area of the examination record. The process for writing rotation information is then terminated. The process then proceeds from step S311 to step S312. If it is judged that the insertion unit has been rotated counterclockwise, the process proceeds to step S314, whereupon a coded counterclockwise rotation mark is written in the rotation information area of the examination record. The process for writing information is then terminated. If the insertion unit has, not been rotated, the process proceeds to step S115. The rotation information area is then cleared, and the process for writing angling information is terminated.

Figure 61:
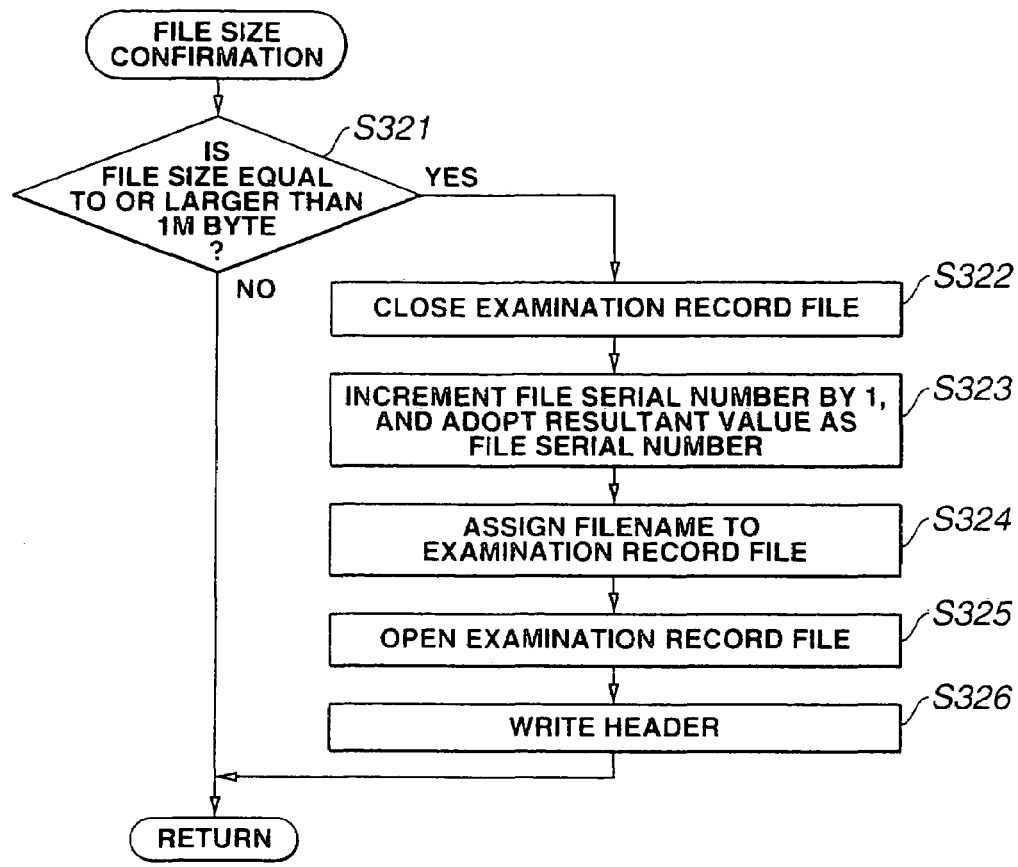

As described in FIG. 61, in the process for confirming the file size of an examination record as executed at step S295 in FIG. 58, first, the file size is checked at step S321. If the file size is equal to or larger than a predetermined size, for example, 1M byte, the file size confirmation process is terminated. In contrast, if the file size falls below the predetermined size, for example, 1M byte, the process proceeds to step S322.

At step S322, the examination record file 272 is closed. The file serial number is incremented by one at step S323. At step S324, a new filename is assigned to the examination record file 272 because the file serial number has been changed. The examination record file 272 having the new filename is created and opened at step S325. A header for the new file is written at step S326. The file size confirmation process is then terminated. In short, the file size confirmation process confines the size of the examination record file 272 to the predetermined size.

According to the present embodiment described above, the shape of an inserted portion of the endoscope is graphically indicated on the screen of the monitor. Endoscope manipulation information composed of angling information and rotation information is displayed in superimposition on the graphical indication of the shape of the inserted portion. As viewed on the monitor, therefore, the relationship between graphical indication of the shape of the inserted portion and a manipulation operation performed on the endoscope can be easily determined, to thereby enable the operator to discern the actual shape of the inserted portion of the endoscope. This contributes to an improvement in maneuvering and manipulating the endoscope.

Moreover, the detected shape-of-inserted portion information is recorded in an examination record file, and the endoscope manipulation information composed of angling information and rotation information is also recorded in the examination record file. An operator can thus reference the examination record at a later time to determine how the endoscope was manipulated during the endoscopic examination. Consequently, the knowledge gained regarding the endoscope manipulation during the endoscopic examination can be preserved.

Furthermore, a filename assigned to an examination record file contains a patient ID number, an examination serial number, and a file serial number. Once the filenames assigned to respective examination record files are referenced, even if the contents of the examination record files themselves are not checked, the presence or absence of a desired examination record can be checked using a patient ID number, an examination serial number, and a file serial number as search information.

An existing examination record can be retrieved based on the filename assigned to an examination record file. Existing examination records can therefore be retrieved quickly. Namely, the conditions for retrieval including a patient ID number need not be set prior to data retrieval. This leads to improvement of maneuverability.

Since a patient ID number, an examination serial number, and a file serial number are recorded in an examination record file, even if the filename assigned to an examination record file is rewritten by mistake, the filename can be restored.

Moreover, a patient ID number is expressed with a character string specifying the date of examination and a patient serial number assigned on the day of examination. Based on the patient ID number specified in a filename assigned to an examination record file or a patient ID number recorded in the examination record file, the patient serial number and the date the examination record file has been created can be easily determined.

Moreover, information composed of the date of examination, a patient serial number, and an examination serial number is specified in the filename assigned to the examination record file or is written into the examination record file. The date, the patient serial number, and the examination serial number for which the examination record file has been created can be easily determined.

The size of an examination record file is limited to a predetermined size, which will prove useful in copying an examination record file onto an external storage medium. It is therefore possible to reference the examination record file using the external storage medium in combination with another apparatus, or to back up the examination record file.

According to the present embodiment, on the assumption that the external storage medium is a flexible disk, when the file size reaches, for example, 1M byte, the addition of new records into the file is stopped. When any other external storage medium is used, a file size limit serving as a criterion for stopping the addition of new records to a file may be set based on the type of storage medium.

For helping to enter a patient ID number, a tentative patient ID number is displayed in the patient ID number entry field. When the tentative patient ID number is accepted as is, the necessity to enter a patient ID number is obviated. This will be found to be very user-friendly.

Figure 63:
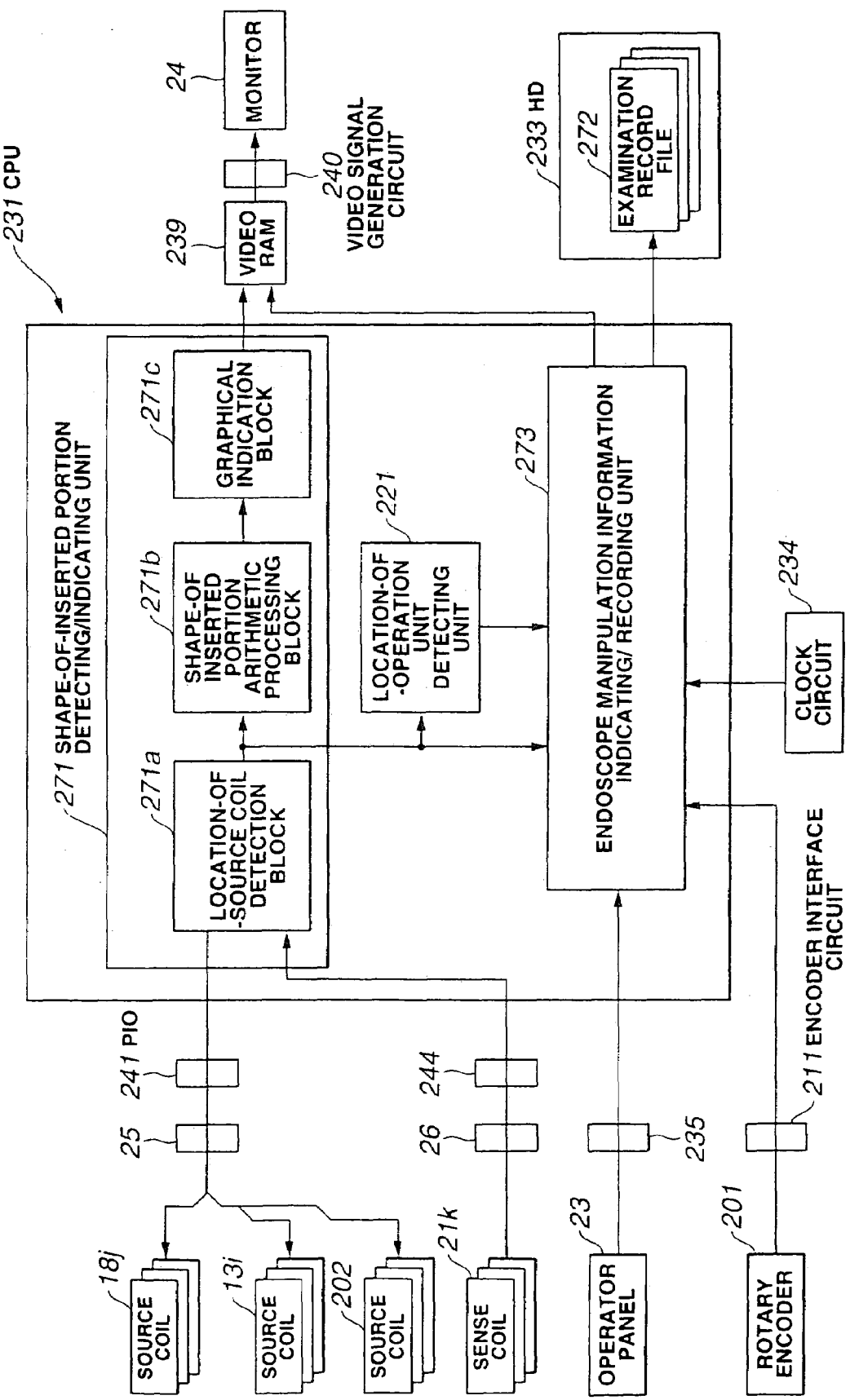

Referring to FIG. 62 and FIG. 63, the tenth embodiment of the present invention will now be described below.

As shown in FIG. 62, according to the present embodiment, an endoscope 6a is substituted for the endoscope 6 employed in the ninth embodiment (see FIG. 44), and a shape-of-endoscope detecting apparatus 3a is employed.

The endoscope 6a has the same functions and features as those of the endoscope 6 employed in the ninth embodiment. In addition, the endoscope 6a includes a rotary encoder 201 and, for example, three source coils 202. The rotary encoder 201 detects the magnitude of a turn by which the angling knob 225 is turned, and sends an electrical signal proportional to the magnitude of a turn to the shape-of-endoscope detecting apparatus 3a. The source coils 202 are incorporated in the operation unit 8 of the endoscope 6a and driven by the drive block 25 of the shape-of-endoscope detecting apparatus 3a.

The shape-of-endoscope detecting apparatus 3a has, in addition to the same hardware as the shape-of-endoscope detecting apparatus 3 employed in the ninth embodiment, an encoder interface circuit 211 for receiving a signal from the rotary encoder 201 and transferring it to a CPU 231.

As shown in FIG. 63, the CPU 231 has, in addition to the same capabilities as the CPU employed in the ninth embodiment, an operation unit locating unit 221. The operation unit locating unit uses the source coil location detection block 271a to acquire location information of the source coils 202 incorporated in the operation unit 8. Based on the location information of the source coils, rotation information concerning the operation unit 8 is detected and transferred to the endoscope manipulation information indicating/recording unit 273.

According to the present embodiment, the endoscope manipulation information indicating/recording unit 273 receives rotation information from the operation unit locating unit 221 instead of from the operator panel 23. Moreover, the endoscope manipulation information indicating/recording unit 273 receives angling information from the rotary encoder 201 instead of from the operator panel 23. The other components and operations are identical to those of the ninth embodiment. The same reference numerals are assigned to identical elements in the drawings, and the description of those elements is therefore omitted.

The foregoing present embodiment can provide the same advantages as the ninth embodiment. Moreover, according to the present embodiment, endoscope manipulation information composed of angling information and rotation information is acquired automatically instead of manually. Compared with the ninth embodiment, the maneuverability of the endoscope is improved greatly.

The present invention is not limited to the embodiments described above. For example, tilt angle sensors may be substituted for the source coils 202 incorporated in the operation unit 8 in order to acquire rotation information of the operation unit 8.

Moreover, for example, a rotary potentiometer or resolver may be substituted for the rotary encoder 201 for detecting the magnitude of a turn by which the angling knob 225 is turned.

Moreover, for example, the keyboard interface circuit 235 may be connected to the operator panel 23 using a PS/2 computer. Moreover, for example, a keyboard or a mouse may be substituted for the operator panel 23.

Marks to be displayed in the angling information indication subspace 263 are not limited to those shown in FIG. 46 and FIG. 47. Alternatively, arrows may be used. Also, marks to be displayed in the rotation information indication subspace 264 are not limited to those shown in FIG. 46 and FIG. 47. Alternatively, right-oriented and left-oriented arrows will do.

Referring to FIG. 64 to FIG. 76, the eleventh embodiment of the present invention will be described below.

Figure 64:
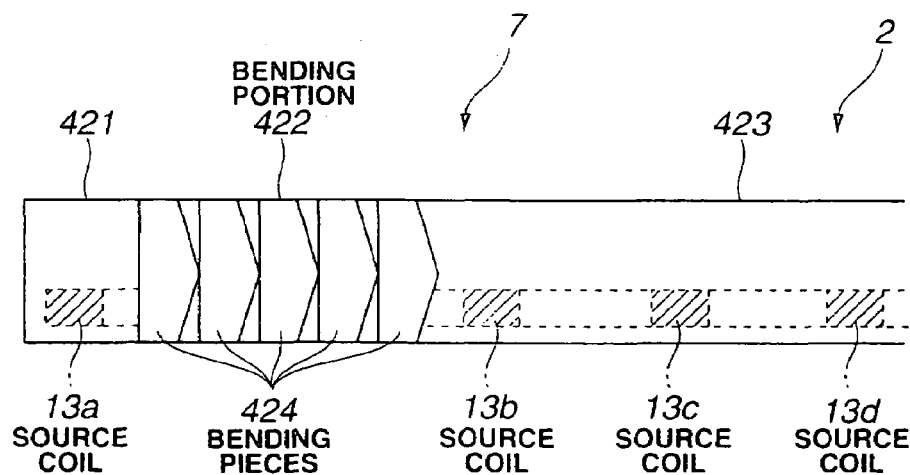

According to the present embodiment, the insertion unit 7 of the endoscope 6 included in the endoscope system 1 has, as shown in FIG. 64, a rigid distal part 421, a bending portion 422, and a soft flexible tube 423 arranged in that order from the distal end thereof. The bending portion 422 can be angled vertically and laterally.

The bending portion 422 has, for example, a plurality of metallic bending pieces 424 serially connected so that the bending pieces can rotate freely, and has a predetermined length. The source coils 13i are incorporated at predetermined positions in the insertion unit 7.

Among the plurality of source coils 13i, the distance between the first source coil 13a located at the distal end and the second source coil 13b is determined in consideration of the length of the bending portion 422 so that both the source coils 13a and 13b will not lie in the bending portion 422.

Eleven source coils of the second through twelfth source coils 13b to 131 are arranged at pre-set intervals so that they will be stowed in the flexible tube 423 of the insertion unit 7. In other words, when the first source coil 13a is located at a predetermined position in the distal part 421, the second source coil 13b is incorporated in the flexible tube 423 but not in the bending portion 422 composed of the bending pieces 424.

Therefore, magnetic fields induced by the source coils 13i are not disturbed by the metallic bending pieces 424. Moreover, a drawback with prior art endoscopes in which the source coils 13i abut the bending pieces 424 or other elements of the bending portion 422 can be overcome with the structure according to the present invention.

Even if the first sensor coil is incorporated not in the distal part 421 but in a similar part, the sensor coils may be arranged in the same manner as described above.

The CPU 231 reads digital data written in a two-port memory 244 over an internal bus in response to a control signal output from the control signal generation circuit (not shown, but ref. 39 in FIG. 3). A main memory 232 is used to sample frequencies exhibited by the digital data (fast Fourier transform (FFT)). Thus, frequencies corresponding to the frequencies of the driving signals applied to the source coils 131 and marker coils 18j are sampled and separated as magnetic field information. Digital data providing the magnetic field information is used to calculate coordinates in a three-dimensional space specifying the locations of the source coils 13i incorporated in the insertion unit 7 of the electronic endoscope 6 or of the marker coils 18j.

The calculated coordinates specifying the locations of the source coils 13i are used to estimate the inserted state of the insertion unit 7 of the electronic endoscope 6.

Graphical data expressing the shape of the insertion unit to be graphically indicated on the monitor 24 is produced and output to the video RAM 239.

Figure 65:
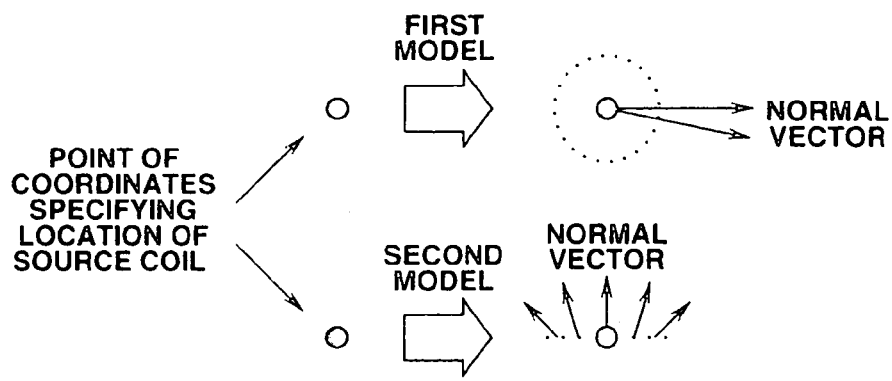

For producing the graphical data expressing the shape of an inserted portion of the insertion unit 7, for example, a three-dimensional model is produced according to an interpolation method using a cubic function curve fitting or natural spline approximation, a third-order B-spline interpolation method, or a second-order B-spline interpolation method. As shown in FIG. 65, the coordinates of points specifying the locations of the source coils are used to interpolate intermediate points. Vectors normal to models representing the calculated coordinates of two adjacent points are calculated. A three-dimensional model expressing the shape of an endoscope is thus constructed.

Figure 66:
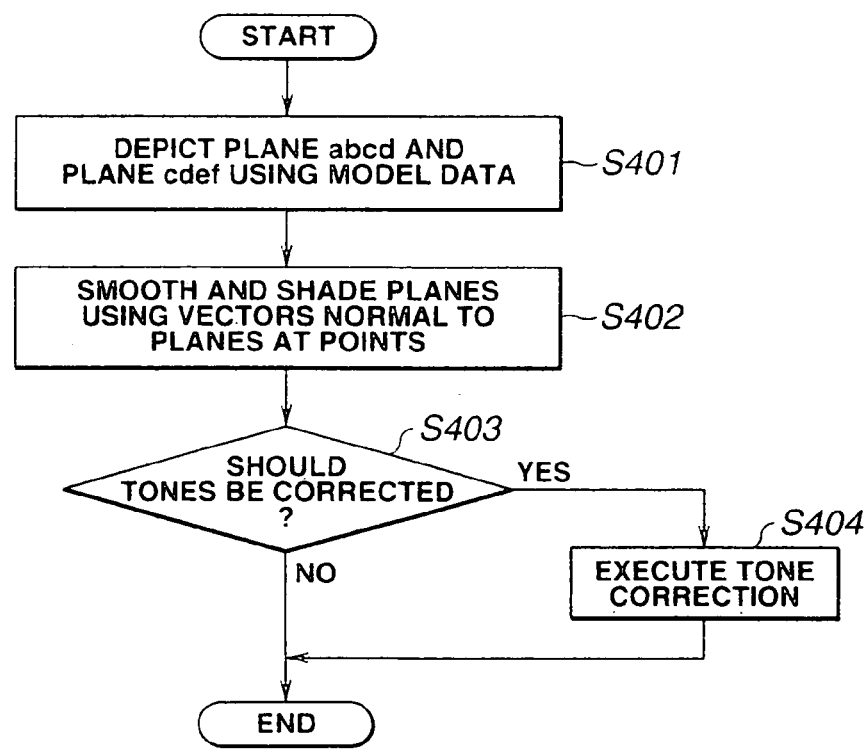
Figure 67:
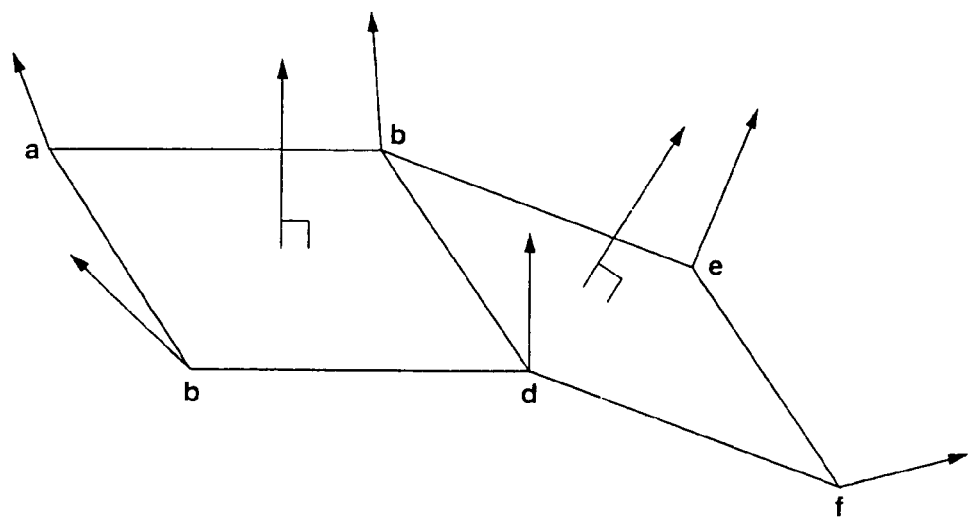

As described in FIG. 66, data representing the three-dimensional model expressing the shape of an inserted portion is used to depict a plane abcd and a plane cdef as shown in FIG. 67 at step S401. Vectors normal to each plane are used to smooth and shade the plane. Thus, three-dimensional graphical data representing the shape of the inserted portion is produced.

Assume that the screen of the monitor 24 is regarded as an XY plane and the depth direction thereof is regarded as the direction of the Z axis. It is judged at step S403 whether or not the tones of an image to be displayed should be corrected using a gray scale in order to improve the appearance of depth in the displayed image to achieve a sense of three-dimensionality upon viewing the image. If it is determined that the tones should be corrected, the process proceeds to step S4. Tone correction is then executed, and the process is terminated.

Figure 68:
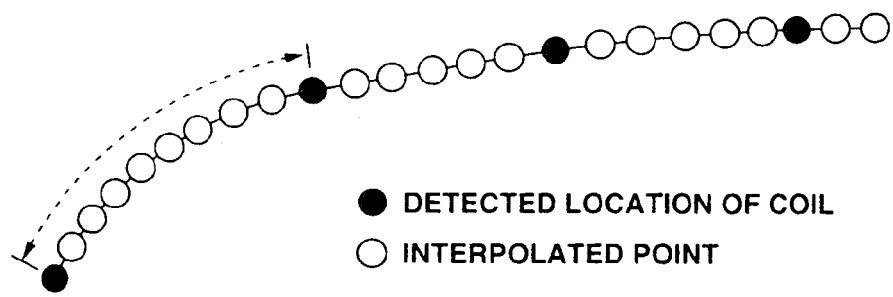

Incidentally, the distance between the first source coil 13a and second source coil 13b, and the distance between adjacent ones of the second through twelfth source coils 13b to 13l are set to predetermined values. Therefore, the coordinates of a plurality of points located between the coordinates of points specifying the locations of the source coils is interpolated based on the distances and the coordinates specifying the locations of the source coils. Thus, a model curve such as that shown in FIG. 68 is constructed in order to depict the shape of the inserted portion of the endoscope.

Additionally, coordinates specifying the locations of the marker coils 18*j* are calculated. Thus, graphical data representing the markers 17*a*, 17*b*, and 17*c* is produced and output to the video RAM 239.

Data stored in the video RAM 239 is read by the video signal generation circuit 240, converted into an analog video signal, and output to the monitor 24.

When the analog video signal is input to the monitor 24, a graphical image expressing the inserted state of the insertion unit 7 and graphical elements 412 indicating the locations of the markers 17*a*, 17*b*, and 17*c* are displayed on the screen 24*a* of the monitor 24.

Since the graphical elements 412 representing the markers are displayed on the screen 24*a* together with the graphical image expressing the shape of an inserted portion, the positional relationship between the insertion unit 7 and the relevant region in the body cavity of a patient can be easily discerned.

In particular, the marker 17*c* placed near the anus serves as an important index based on which it can be judged whether or what of the insertion unit 7 lies inside the body of the patient 5. Another marker may be prepared and placed on an operator's hand, whereby the position of the operator's hand may be indicated on the screen 24*a* of the monitor 24.

If it is judged at step S403 that the color tones of the displayed graphical indication of the endoscope do not need to be corrected, the process is terminated without executing the tone correction process. A method according to which the CPU 231 estimates coordinates in a three-dimensional space specifying the locations of the source coils 13*i* is described in Japanese Patent Application No. 10-69075, filed previously by the present applicant. The same method is preferably used for estimation of coordinates in the present embodiment. Therefore, the description of the method for estimating coordinate locations in the present invention is omitted herein.

Furthermore, a keyboard 23 used to instruct processing of the graphical image expressing the shape of an inserted portion displayed on the display screen 24*a* is connected to a keyboard interface. A thickness-of-inserted portion change signal or an anus cut mode signal that will be described later is transmitted in response to an entry made at the keyboard 13.

Now, a description will be provided for the signal to change the displayed thickness of the shape of the inserted endoscope portion and anus cut mode signal.

First, the thickness-of-inserted portion change signal will be described.

Figure 69A:
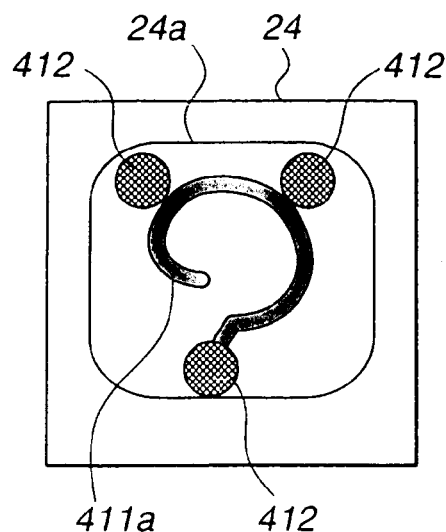
FIG. 69A to FIG. 69C are explanatory diagrams showing a difference in thickness among a plurality of graphical images, which express the shape of an inserted portion and are displayed on the display screen according to a thickness-of-inserted portion change signal.
Figure 69B:
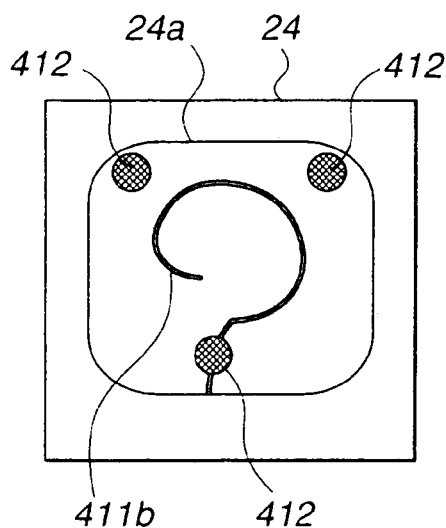
Figure 69C:
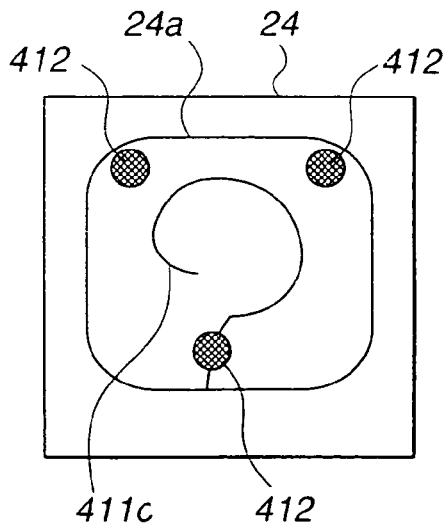
Figure 76:
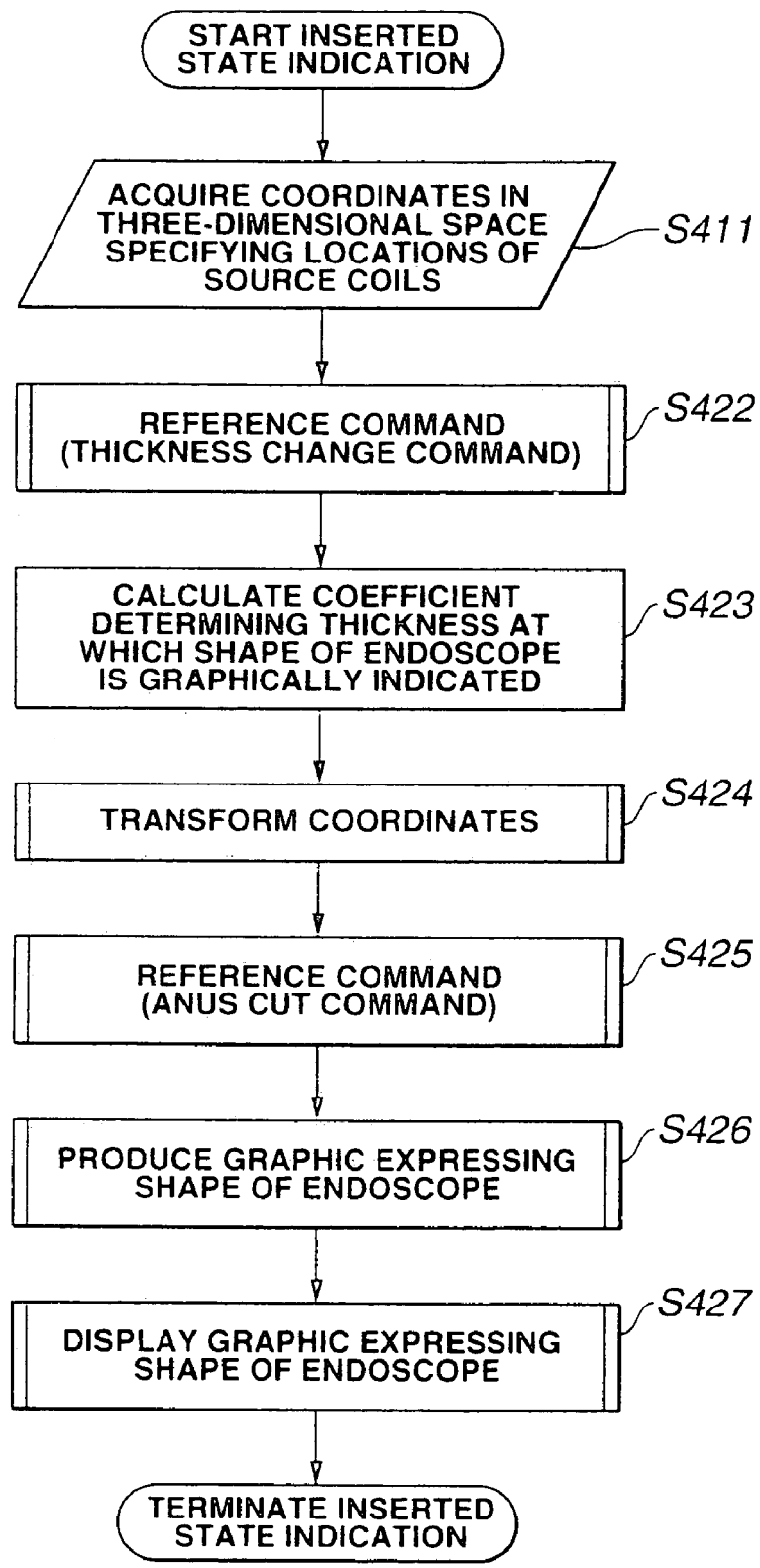

The graphical image expressing the shape of an inserted portion of an endoscope is displayed on the screen 24*a* while being enlarged or reduced based on a calculated thickness at which the shape of the insertion unit 7 is graphically indicated, and the size of the display window presented on the screen 24*a*. The thickness-of-inserted portion change signal is used to vary the thickness (width) of the graphical image expressing the shape of an inserted portion and displayed on the screen 24*a*. When an operator gives an instruction via, for example, the keyboard 13, the thickness portion of the graphical image expressing the shape of an inserted portion can be varied in stepwise increments. Specifically, the graphical image is changed to graphical images 411*a*, 411*b*, and 411*c* that are mutually different in thickness as shown in FIG. 69A, 69B, and 69C. Incidentally, changes in the thickness may be achieved continuously (smoothly) instead of in increments.

Figure 70A:
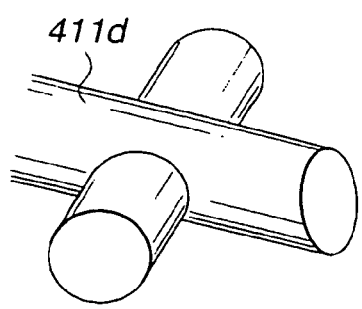
FIG. 70A and FIG. 70B are explanatory diagrams for describing the relationship between the thickness of a graphical image expressing the shape of an inserted portion and precision in observation.
Figure 70B:
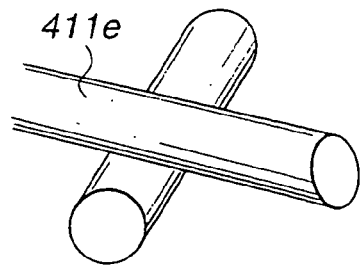

Consequently, the graphical image expressing the shape of an inserted portion of an endoscope can be changed to any of the graphical images 411*a*, 411*b*, and 411*c* that has as large a thickness as appropriate for the existing configuration of the endoscope. For example, when the insertion unit is twisted during examination, if the displayed thickness is too large, one part of the twisted portion may be graphically indicated as if it were, as appears in the graphical image 411*d* shown in FIG. 70A, merged into the other part thereof. In this case, the thickness-of-inserted portion change signal is used to change the thickness of the graphical image expressing the shape of the inserted portion. Consequently, a graphical image 411*e* in which it is possible to, as shown in FIG. 70B, readily discern the positional relationship between the parts of the twisted portion is displayed instead of the graphical image 411*d*.

The thickness of a graphical image expressing the shape of an inserted portion is calculated in the CPU 231 according to, for example, the following expression:

Thickness=(0.75+0.25*X*)*r* where r denotes the radius and X denotes the magnification used for adjustment.

Next, the anus cut mode signal will be described.

The anus cut mode signal is used to instruct that a graphical image expressing the shape of only the intracavitary portion of the insertion unit of an endoscope is to be displayed on the screen.

As shown in FIG. 71A, a graphical image 411*f* displayed within a window on the display screen 24 expresses the shape of a portion of the insertion unit lying within the three markers 17*a*, 17*b*, and 17*c* and extending outside beyond the marker 17*c* placed near the patient's anus. The markers are represented with the graphical elements 412. The graphical image 411*f* is changed to a graphical image 411*g* expressing the shape of only the portion of the insertion unit lying within the three markers as shown in FIG. 71B. In other words, the portion of the graphical image 411*f* that would appear beyond the graphical image 412 that is displayed on the dashed line in FIG. 71B and represents the marker 17*c* placed near the patient's anus is not displayed.

In another arrangement, as shown in FIG. 71C, the shape of the portion of the insertion unit 7 extending from a planar area A, which is indicated with the dashed line in the figure and defined to coincide with the position of the patient's anus, in the direction of arrow B is not graphically indicated. In other words, the portion of the insertion unit 7 not inserted into a body cavity of a patient lying down on the examination table 7 is not graphically indicated.

As mentioned above, the anus cut mode, in which the graphical image 411*g* expressing the shape of only the intracavitary portion of the insertion unit 7 is displayed, has the drawback described below. When the distal part of the insertion unit 7 is directed towards the anus during the course of insertion, it is hard to distinguish the distal position of the insertion unit 7 from the rear (proximal) position of the inserted portion thereof near the anus when viewing the graphical image 411 expressing the shape of the inserted portion and displayed on the screen 24*a* as illustrated in FIG. 72.

The present embodiment may therefore include a feature to help distinguish the distal position of the insertion unit 7 from the rear position of the inserted portion thereof near the anus when viewing the screen 24a irrespective of the direction in which the insertion unit 7 is inserted. Specifically, a graphical image 411h displayed on the screen 24a as shown in FIG. 73A has a colored portion 414 serving as an identifier for helping to identify the distal position of the insertion unit. A graphical image 411i displayed on the screen 24a as shown in FIG. 73B has a rounded portion 415 serving as an identifier for helping to identify the distal position of the insertion unit. Consequently, the distal position of the insertion unit and the rear (proximal) position of the inserted portion thereof near the patient's anus are readily distinguished from each other.

At this time, the colored portion for helping to identify the distal position of the insertion unit is produced by the tone correction process. The rounded portion shown in FIG. 73B is produced by the process performed for detecting the shape of an endoscope and graphically indicating the detected shape using a model.

To facilitate distinguishing the distal position of the insertion unit from the rear (proximal) position of the inserted portion thereof near the patient's anus, a cavity wall mark 416 serving as an identifier of a cavity wall located near the patient's anus may be used instead of the colored portion 414 or rounded portion 415. That is, a graphical image 411j expressing the shape of an inserted portion with the cavity wall mark 416 superimposed thereon may be displayed on the screen 24a. Thus, the distal position of the insertion unit and the rear position of the inserted portion thereof near the patient's anus can be distinguished from each other.

Moreover, as shown in FIG. 75, a graphical image 411k that combines the graphical image 411h shown in FIG. 73A, the graphical image 411i shown in FIG. 73B, and the graphical image 411j shown in FIG. 74 may be displayed on the screen 24a. In this case, the distal position of the insertion unit and the rear (proximal) position of the inserted portion thereof near the patient's anus are explicitly distinguished from each other. As described in FIG. 76, in the process to produce the graphical indication of the shape of an inserted portion, first, coordinates in a three-dimensional space are acquired using magnetic fields induced by the source coils at step S411. A thickness change signal issued using the keyboard is referenced at step S412. A coefficient determining the thickness at which the shape of an inserted portion is graphically indicated is calculated based on the referenced signal at step S413. The process then proceeds to step S414, at which the coordinates acquired at step S411 are transformed into those in the coordinate system defined on the display screen. An anus cut mode signal issued using the keyboard is referenced at step S415. The process then proceeds to step S416. A graphical image expressing the shape of the inserted portion of the insertion unit is produced based on the results of steps S413, S414, and S415. The graphical image is then displayed at step S417.

None of the plurality of source coils incorporated in the insertion unit is incorporated in the bending portion having the plurality of serially connected bending pieces. Even when an operator angles the bending portion, the magnetic fields 20 induced by the source coils will not be disturbed by the bending pieces. Highly precise coordinates specifying the locations of the source coils are therefore acquired. A graphical image expressing the shape of the insertion unit is therefore produced with high precision.

Moreover, since none of the source coils is incorporated in the bending portion, a drawback in prior art endoscopes in which when the bending portion is angled, at least one of the source coils abuts against at least one of the bending pieces or any other structural element of the bending portion can be overcome.

Furthermore, when the anus cut mode signal is issued from an input device. An identifier for helping to identify at least one of the distal position of the insertion unit or the rear (proximal) position of the inserted portion thereof near the patient's anus is depicted together with a graphical image expressing the portion of the insertion unit lying inside the patient's body. It can be recognized upon viewing of the screen which of the positions indicated in the graphical image is the distal position of the insertion unit.

The thickness-of-inserted portion change signal is issued using the input device. The thickness of the graphical image expressing the shape of the inserted portion of the insertion unit and displayed on the screen can be changed to an operator-desired thickness. An operator can therefore proceed with work with the scheduled examination or medical procedure with the graphical image displayed in the most appropriate or preferred manner. Moreover, even when the insertion unit is twisted, the positional relationship between the twisted portion and the other portion thereof can be determined reliably. This leads to a drastic improvement in the performance of the endoscope and the observation thereof on a monitor.

According to the present embodiment, the endoscope has a plurality of source coils incorporated therein so as to provide a shape detection function. The number of source coils incorporated in the endoscope may be any number and may be freely increased or decreased.

Moreover, a probe having a plurality of source coils incorporated therein as mentioned previously above may be passed through the treatment instrument passage channel formed in an endoscope instead of using a shape detection endoscope having the source coils incorporated therein. Thus, the shape of the insertion unit may be graphically indicated on the screen of the monitor according to the aforesaid embodiments.

According to the present invention, it is apparent that a wide range of different embodiments can be constructed based on the preferred embodiments of the invention described herein without a departure from the spirit or scope of the invention. The present invention is limited by the appended claims but is not restricted by any of the specific embodiments discussed herein.

What is claimed is:

1. A shape of endoscope detecting apparatus comprising:
a shape detecting means for detecting the shape of a portion of an insertion unit of an endoscope inserted into a subject, and producing graphic data expressing the shape thereof
a first marker means for marking a location on the subject at which the endoscope is inserted;
a first location information of marker acquiring means for acquiring first location information of said first marker means; and
a display control means for graphically indicating the graphic shape of data produced by the shape detecting means, the display control means being configured to graphically indicate on a display means the shape of the intracavitary portion of the insertion unit obtained by subjecting the graphic shape data produced by the shape detecting means to coordinate processing with the first location information of the first marker as a reference, wherein said location information is a first point of coordinates in a predetermined coordinate system, and further comprising:
a second marker means independent of said first marker means and movable to any location on the subject;
a second location information of marker acquiring means for acquiring location information of said second marker means as a second point of coordinates contained in the coordinate system;
a point of coordinates shifting means for shifting the first point of coordinates acquired by said first location information of marker acquiring means with respect to the second point of coordinates acquired by said second location information of marker acquiring means; and
a display control means for graphically indicating on said display means the location information of said first marker means according to the first point of coordinates shifted by said point of coordinates shifting means.

2. A shape of endoscope detecting apparatus comprising:
a shape detecting means for detecting the shape of a portion of an insertion unit of an endoscope inserted into a subject, and producing graphic data expressing the shape thereof;
a first marker means for marking a location on the subject at which the endoscope is inserted;
a first location information of marker acquiring means for acquiring first location information of said first marker means; and
a display control means for graphically indicating the graphic shape of data produced by the shape detecting means, the display control means being configured to graphically indicate on a display means the shape of the intracavitary portion of the insertion unit obtained by subjecting the graphic shape data produced by the shape detecting means to coordinate processing with the first location information of the first marker as a reference,
wherein location information of said first marker means is a first point of coordinates contained in a predetermined coordinate system, and farther comprising:
a second marker means independent of said first marker means and movable to any location on the subject;
a second location information of marker acquiring means for acquiring location information of said second marker means as a second point of coordinates contained in the coordinate system;
a point of coordinates shifting means for shifting the first point of coordinates acquired by said first location information of marker acquiring means and points of coordinates defining the shape of an inserted portion of the insertion unit with respect to the second point of coordinates acquired by said second location information of marker acquiring means; and,
a display control means to process coordinates for graphically indicating on said display means the location information of said first marker means and the shape of the inserted portion according to the first point of coordinates and the points of coordinates defining the shape of the inserted portion which are shifted by said point of coordinates shifting means.

3. A shape of endoscope detecting apparatus comprising:
a shape detecting means for detecting the shape of a portion of an insertion unit of an endoscope inserted into a subject, and producing graphic data expressing the shape thereof;
a first marker means for marking a location on the subject at which the endoscope is inserted;
a first location information of marker acquiring means for acquiring first location information of said first marker means; and
a display control means for graphically indicating the graphic shape of data produced by the shape detecting means, the display control means being configured to graphically indicate on a display means the shape of the intracavitary portion of the insertion unit obtained by subjecting the graphic shape data produced by the shape detecting means to coordinate processing with the first location information of the first marker as a reference,
wherein said location information is a first point of coordinates in a predetermined coordinate system, and further comprising:
a second marker means independent of said first marker means and movable to any location on the subject;
a second location information of marker acquiring means for acquiring location information of said second marker means as a second point of coordinates contained in the coordinate system when the insertion unit of the endoscope has just been inserted into the subject;
a point of coordinates shifting means for shifting the first point of coordinates acquired by said first location information of marker acquiring means with respect to the second point of coordinates acquired by said second location information of marker acquiring means; and,
a display control means to process coordinates for graphically indicating on said display means the location information of said first marker means according to the first point of coordinates shifted by said point of coordinates shifting means.

4. A shape of endoscope detecting apparatus comprising:
a shape detecting means for detecting the shape of a portion of an insertion unit of an endoscope inserted into a subject, and producing graphic data expressing the shape of the portion of the insertion unit;
an endoscope manipulation information acquiring means for acquiring manipulation information representing manipulations performed on the endoscope inserted into the subject;
a marker means for marking a location on the subject at which the endoscope is inserted; a location information of marker acquiring means for acquiring location coordinates information of said marker means;
a display control means for processing graphic data coordinates for graphically indicating on a display means the shape of the inserted portion detected by said shape detecting means, wherein the graphic data coordinates processing using as a reference the location coordinates information of said marker means acquired by said location information of marker acquiring means; and
a superimposing means for superimposing on said display means the manipulation information acquired by said endoscope manipulation information acquiring means on the shape of the inserted portion graphically indicated by said display control means.

5. A shape of endoscope detecting apparatus according to claim 4, wherein said superimposing means superimposes an absolute scale on the shape of the inserted portion graphically indicated on said display means.

6. A shape of endoscope detecting apparatus according to claim 4, wherein said superimposing means superimposes the length of the portion of the insertion unit of the endoscope inserted in to the subject, the length of the portion being detected by a length of inserted portion detecting means, on the shape of the inserted portion graphically indicated on said display means.

7. A shape of endoscope detecting method comprising the steps of:
placing a first marker near a first location of a subject through which an endoscope is inserted;
acquiring first location coordinates of said first marker;
detecting the shape of a portion of an insertion unit of the endoscope inserted into the subject;
producing graphic data coordinates expressing the shape of the portion of the insertion unit;
processing the graphic data coordinates using the first location coordinates of said first marker as a reference; and
graphically indicating on a display means the shape of the inserted portion detected at said shape of inserted portion detecting step,
further comprising the steps of:
acquiring second location coordinates of a second marker, the second marker being independent of said first marker and movable to any location on the subject;
shifting the first location coordinates acquired at said first location coordinates of said first marker acquiring step with respect to the second location coordinates acquired at said second location coordinates of said second marker acquiring step; and
extending display control to process coordinates for graphically indicating the first location coordinates of said first marker shifted at said first location coordinates shifting step.

8. A shape of endoscope detecting method comprising the steps of:
placing a first marker near a first location of a subject through which an endoscope is inserted;
acquiring first location coordinates of said first marker;
detecting the shape of a portion of an insertion unit of the endoscope inserted into the subject;
producing graphic data coordinates expressing the shape of the portion of the insertion unit;
processing the graphic data coordinates using the first location coordinates of said first marker as a reference; and
graphically indicating on a display means the shape of the inserted portion detected at said shape of inserted portion detecting step,
further comprising the steps of:
acquiring second location coordinates of a second marker, the second marker being independent of said first marker and movable to any location on the subject;
shifting the first location coordinates acquired at said first location coordinates of the first marker acquiring step and the graphic data coordinates defining the shape of an inserted portion of the insertion unit with respect to the second location coordinates acquired at said second location coordinates of marker acquiring step; and
extending display control to process coordinates for graphically indicating on said display means the first location coordinates of said first marker and the shape of the inserted portion according to the first location coordinates and the graphic data coordinates defining the shape of the inserted portion which are shifted at said shifting step.

9. A shape of endoscope detecting method comprising the steps of:
placing a first marker near a first location of a subject through which an endoscope is inserted;
acquiring first location coordinates of said first marker;
detecting the shape of a portion of an insertion unit of the endoscope inserted into the subject;
producing graphic data coordinates expressing the shape of the portion of the insertion unit;
processing the graphic data coordinates using the first location coordinates of said first marker as a reference; and
graphically indicating on a display means the shape of the inserted portion detected at said shape of inserted portion detecting step,
further comprising the steps of:
acquiring second location coordinates of a second marker, the second marker being independent of said first marker and movable to any location on the subject, when the insertion unit of the endoscope has just been inserted into the subject;
shifting the first coordinates acquired at said first location coordinates of the first marker acquiring step with respect to the second location coordinates acquired at said second location coordinates of the second marker acquiring step; and
extending display control to process graphic data coordinates for graphically indicating on said display means the first location coordinates of said first marker shifted at said shifting step.

10. A shape of endoscope detecting method comprising the steps of:
placing a predetermined marker near a location of a subject through which an insertion unit of an endoscope is inserted into a subject;
acquiring location coordinates information of said marker;
detecting the shape of the portion of the insertion unit of the endoscope inserted into the subject;
producing graphic data expressing the shape of the portion the insertion unit;
acquiring manipulation information representing manipulations performed on the endoscope inserted into the subject;
extending display control to process graphic data coordinates for graphically indicating on a display the shape of the inserted portion; and
superimposing the manipulation information acquired by said endoscope manipulation information acquiring step on the shape of the inserted portion graphically indicated on said display means at said display control step.

11. A shape of endoscope detecting method according to claim 10, further comprising a step of superimposing an absolute scale on the shape of the inserted portion of the endoscope graphically indicated on said display means.

12. A shape of endoscope detecting method according to claim 10, further comprising:
a step of detecting the length of the portion of the insertion unit of the endoscope inserted into the subject; and
a step of superimposing the length of the inserted portion detected at said length of inserted portion detecting step on the shape of the inserted portion of the endoscope graphically indicated on said display means.

* * * * *